(12) United States Patent
Kelly et al.

(10) Patent No.: US 11,857,793 B2
(45) Date of Patent: Jan. 2, 2024

(54) MANAGING STORAGE OF SENSED INFORMATION

(71) Applicant: Medtronic, Inc., Minneapolis, MN (US)

(72) Inventors: Kevin J. Kelly, Shoreview, MN (US); Henrique Weh, Charlotte, NC (US)

(73) Assignee: Medtronic, Inc., Minneapolis, MN (US)

( * ) Notice: Subject to any disclaimer, the term of this patent is extended or adjusted under 35 U.S.C. 154(b) by 210 days.

(21) Appl. No.: 17/343,201

(22) Filed: Jun. 9, 2021

(65) Prior Publication Data

US 2021/0387003 A1 Dec. 16, 2021

Related U.S. Application Data

(60) Provisional application No. 63/037,406, filed on Jun. 10, 2020.

(51) Int. Cl.
*A61N 1/36* (2006.01)
*A61B 5/24* (2021.01)
(Continued)

(52) U.S. Cl.
CPC ........ *A61N 1/36135* (2013.01); *A61B 5/1116* (2013.01); *A61B 5/24* (2021.01);
(Continued)

(58) Field of Classification Search
CPC ............ A61N 1/36135; A61N 1/36178; A61N 1/36062; A61N 1/36139; A61N 1/3605;
(Continued)

(56) References Cited

U.S. PATENT DOCUMENTS 5,603,726 A 2/1997 Schulman et al.
5,800,465 A 9/1998 Thompson et al.
(Continued)

FOREIGN PATENT DOCUMENTS

CN 105792745 A 7/2016
EP 0613390 A1 9/1994
(Continued)

OTHER PUBLICATIONS

"St. Jude's Prodigy Neurostimulator with Burst Technology," Medgadget, Mar. 20, 2014, 4 pp.
(Continued)

*Primary Examiner* — Paula J Stice
(74) *Attorney, Agent, or Firm* — Shumaker & Sieffert, P.A.

(57) ABSTRACT

This disclosure is directed to devices, systems, and techniques for managing storing sensed information. In some examples, a system includes a memory and processing circuitry. The processing circuitry may be configured to receive evoked compound action potential (ECAP) information, wherein the ECAP information comprises information from a plurality of evoked compound action potential (ECAP) signals, receive a trigger signal requesting long-term storage of at least a portion of the ECAP information in the memory, and responsive to receiving the trigger signal, store the at least portion of the ECAP information in the memory.

30 Claims, 15 Drawing Sheets

(51) Int. Cl.
*A61B 5/11* (2006.01)
*G16H 40/63* (2018.01)

(52) U.S. Cl.
CPC ......... *A61N 1/36178* (2013.01); *G16H 40/63* (2018.01); *A61B 2560/0475* (2013.01); *A61B 2562/0219* (2013.01)

(58) Field of Classification Search
CPC ............ A61N 1/36128; A61N 1/36132; A61N 1/371; A61N 1/3702; A61N 1/37247; A61B 5/1116; A61B 5/24; A61B 2560/0475; A61B 2562/0219
See application file for complete search history.

(56) References Cited

U.S. PATENT DOCUMENTS

| | | | |
|---|---|---|---|
| 5,908,392 | A | 6/1999 | Wilson et al. |
| 6,157,861 | A | 12/2000 | Faltys et al. |
| 6,205,360 | B1 | 3/2001 | Carter |
| 6,289,247 | B1 | 9/2001 | Faltys et al. |
| 6,314,325 | B1 | 11/2001 | Fitz |
| 6,421,566 | B1 | 7/2002 | Holsheimer |
| 6,505,078 | B1 | 1/2003 | King et al. |
| 6,675,046 | B2 | 1/2004 | Holsheimer |
| 6,850,802 | B2 | 2/2005 | Holsheimer |
| 6,988,006 | B2 | 1/2006 | King et al. |
| 7,076,292 | B2 | 7/2006 | Forsberg |
| 7,206,640 | B1 | 4/2007 | Overstreet |
| 7,333,858 | B2 | 2/2008 | Killian et al. |
| 7,577,480 | B2 | 8/2009 | Zeijlemaker |
| 7,616,999 | B2 | 11/2009 | Overstreet et al. |
| 7,657,318 | B2 | 2/2010 | King et al. |
| 7,689,289 | B2 | 3/2010 | King |
| 7,742,810 | B2 | 6/2010 | Moffitt et al. |
| 7,792,583 | B2 | 9/2010 | Miesel et al. |
| 8,036,747 | B2 | 10/2011 | Thacker et al. |
| 8,090,446 | B2 | 1/2012 | Fowler et al. |
| 8,504,150 | B2 | 8/2013 | Skelton |
| 8,515,549 | B2 | 8/2013 | Panken et al. |
| 8,620,441 | B2 | 12/2013 | Greenberg et al. |
| 8,676,329 | B2 | 3/2014 | Wacnik et al. |
| 8,694,108 | B2 | 4/2014 | Alataris et al. |
| 8,708,934 | B2 | 4/2014 | Skelton et al. |
| 8,712,533 | B2 | 4/2014 | Alataris et al. |
| 8,712,534 | B2 | 4/2014 | Wei |
| 8,751,009 | B2 | 6/2014 | Wacnik |
| 8,897,888 | B2 | 11/2014 | Parker et al. |
| 8,918,177 | B2 | 12/2014 | Gauthier |
| 8,923,984 | B2 | 12/2014 | Parker et al. |
| 8,958,885 | B2 | 2/2015 | Panken et al. |
| 9,002,460 | B2 | 4/2015 | Parker |
| 9,072,910 | B2 | 7/2015 | Parker et al. |
| 9,084,900 | B2 | 7/2015 | Hershey et al. |
| 9,089,714 | B2 | 7/2015 | Robinson |
| 9,089,715 | B2 | 7/2015 | Parker et al. |
| 9,138,582 | B2 | 9/2015 | Doan et al. |
| 9,155,892 | B2 | 10/2015 | Parker et al. |
| 9,283,373 | B2 | 3/2016 | Parker et al. |
| 9,302,112 | B2 | 4/2016 | Bornzin et al. |
| 9,339,655 | B2 | 5/2016 | Carbunaru |
| 9,364,667 | B1 | 6/2016 | Dinsmoor et al. |
| 9,381,356 | B2 | 7/2016 | Parker et al. |
| 9,386,934 | B2 | 7/2016 | Parker et al. |
| 9,387,325 | B1 | 7/2016 | Min et al. |
| 9,511,231 | B1 | 12/2016 | Kent et al. |
| 9,553,148 | B2 | 1/2017 | Xie et al. |
| 9,566,439 | B2 | 2/2017 | Single et al. |
| 9,597,507 | B2 | 3/2017 | Johanek et al. |
| 9,700,713 | B2 | 7/2017 | Robinson et al. |
| 9,872,990 | B2 | 1/2018 | Parker et al. |
| 9,993,646 | B2 | 6/2018 | Parramon et al. |
| 10,183,168 | B2 | 1/2019 | Baru et al. |
| 10,327,654 | B2 | 6/2019 | Strahl et al. |
| 10,569,088 | B2 | 2/2020 | Dinsmoor et al. |
| 10,933,242 | B2 | 3/2021 | Torgerson |
| 2004/0267333 | A1 | 12/2004 | Kronberg |
| 2008/0033508 | A1* | 2/2008 | Frei ......... A61B 5/369 607/62 |
| 2008/0058651 | A1* | 3/2008 | Shen ............ A61B 5/0031 607/9 |
| 2008/0221640 | A1 | 9/2008 | Overstreet et al. |
| 2008/0300655 | A1* | 12/2008 | Cholette ......... A61N 1/36135 607/60 |
| 2011/0054570 | A1 | 3/2011 | Lane |
| 2011/0071589 | A1 | 3/2011 | Starkebaum et al. |
| 2011/0077712 | A1 | 3/2011 | Killian |
| 2011/0125223 | A1 | 5/2011 | Carbunaru et al. |
| 2012/0155188 | A1 | 6/2012 | Buettner et al. |
| 2012/0265028 | A1* | 10/2012 | Hughes ............ A61B 5/1117 600/301 |
| 2013/0085406 | A1* | 4/2013 | Gunderson ....... A61N 1/37247 600/518 |
| 2013/0208390 | A1 | 8/2013 | Singh et al. |
| 2013/0268021 | A1 | 10/2013 | Moffitt |
| 2013/0289664 | A1 | 10/2013 | Johanek |
| 2013/0289683 | A1 | 10/2013 | Parker et al. |
| 2014/0005753 | A1 | 1/2014 | Carbunaru |
| 2014/0025146 | A1 | 1/2014 | Alataris et al. |
| 2014/0031896 | A1 | 1/2014 | Alataris et al. |
| 2014/0031905 | A1 | 1/2014 | Irazoqui et al. |
| 2014/0074189 | A1 | 3/2014 | Moffitt |
| 2014/0142656 | A1 | 5/2014 | Alataris et al. |
| 2014/0142673 | A1 | 5/2014 | Alataris et al. |
| 2014/0194772 | A1 | 7/2014 | Single et al. |
| 2014/0236042 | A1 | 8/2014 | Parker et al. |
| 2014/0236257 | A1 | 8/2014 | Parker et al. |
| 2014/0243924 | A1 | 8/2014 | Zhu et al. |
| 2014/0243926 | A1 | 8/2014 | Carcieri et al. |
| 2014/0243931 | A1 | 8/2014 | Parker et al. |
| 2014/0277282 | A1 | 9/2014 | Jaax |
| 2014/0288577 | A1 | 9/2014 | Robinson et al. |
| 2014/0293737 | A1 | 10/2014 | Parker et al. |
| 2014/0296936 | A1 | 10/2014 | Alataris et al. |
| 2014/0324143 | A1 | 10/2014 | Robinson et al. |
| 2014/0371813 | A1 | 12/2014 | King et al. |
| 2014/0378941 | A1 | 12/2014 | Su et al. |
| 2014/0379043 | A1 | 12/2014 | Howard |
| 2015/0005842 | A1 | 1/2015 | Lee et al. |
| 2015/0012068 | A1 | 1/2015 | Bradley et al. |
| 2015/0032181 | A1 | 1/2015 | Baynham et al. |
| 2015/0057729 | A1 | 2/2015 | Parker et al. |
| 2015/0127062 | A1 | 5/2015 | Holley et al. |
| 2015/0173636 | A1 | 6/2015 | Mokelke et al. |
| 2015/0179177 | A1 | 6/2015 | Nagao |
| 2015/0282725 | A1 | 10/2015 | Single |
| 2015/0313487 | A1 | 11/2015 | Single et al. |
| 2015/0360031 | A1 | 12/2015 | Bornzin et al. |
| 2015/0374999 | A1 | 12/2015 | Parker et al. |
| 2016/0082252 | A1 | 3/2016 | Hershey et al. |
| 2016/0121124 | A1 | 5/2016 | Johanek et al. |
| 2016/0129272 | A1 | 5/2016 | Hou et al. |
| 2016/0136420 | A1 | 5/2016 | Brink et al. |
| 2016/0157769 | A1 | 6/2016 | Min et al. |
| 2016/0158550 | A1 | 6/2016 | Hou et al. |
| 2016/0166164 | A1 | 6/2016 | Obradovic et al. |
| 2016/0175594 | A1 | 6/2016 | Min et al. |
| 2016/0206883 | A1 | 7/2016 | Bornzin et al. |
| 2016/0287126 | A1 | 10/2016 | Parker et al. |
| 2016/0287182 | A1 | 10/2016 | Single |
| 2016/0339251 | A1 | 11/2016 | Kent et al. |
| 2016/0346534 | A1 | 12/2016 | Isaacson et al. |
| 2016/0361542 | A1 | 12/2016 | Kaula et al. |
| 2017/0001017 | A9 | 1/2017 | Parker et al. |
| 2017/0049345 | A1 | 2/2017 | Single |
| 2017/0071490 | A1 | 3/2017 | Parker et al. |
| 2017/0135624 | A1 | 5/2017 | Parker |
| 2017/0173332 | A1 | 6/2017 | Overstreet |
| 2017/0209695 | A1 | 7/2017 | Solomon |
| 2017/0216587 | A1 | 8/2017 | Parker |
| 2017/0216602 | A1 | 8/2017 | Waataja et al. |
| 2017/0296823 | A1 | 10/2017 | Hershey et al. |
| 2017/0361101 | A1 | 12/2017 | Single |
| 2017/0361103 | A1 | 12/2017 | Hadjiyski |

(56) References Cited

U.S. PATENT DOCUMENTS

| | | | |
|---|---|---|---|
| 2018/0056073 | A1 | 3/2018 | Torgerson |
| 2018/0078769 | A1 | 3/2018 | Dinsmoor et al. |
| 2018/0110464 | A1* | 4/2018 | Annoni .................. A61B 5/021 |
| 2018/0110987 | A1 | 4/2018 | Parker |
| 2018/0117335 | A1 | 5/2018 | Parker et al. |
| 2018/0126169 | A1* | 5/2018 | Hou ................... A61N 1/36139 |
| 2018/0132760 | A1 | 5/2018 | Parker |
| 2018/0140842 | A1* | 5/2018 | Ó Laighin ............ A61B 5/1116 |
| 2019/0099601 | A1 | 4/2019 | Torgerson |
| 2019/0105496 | A1 | 4/2019 | Min et al. |
| 2019/0168000 | A1 | 6/2019 | Laird-Wah |
| 2019/0209844 | A1 | 7/2019 | Esteller et al. |
| 2019/0388692 | A1 | 12/2019 | Dinsmoor et al. |
| 2019/0388695 | A1 | 12/2019 | Dinsmoor et al. |
| 2020/0155023 | A1* | 5/2020 | Lashghari .............. A61B 5/364 |
| 2020/0171312 | A1 | 6/2020 | Dinsmoor et al. |
| 2020/0171313 | A1 | 6/2020 | Dinsmoor et al. |
| 2021/0101007 | A1 | 4/2021 | Hamner et al. |
| 2021/0121699 | A1 | 4/2021 | Dinsmoor et al. |
| 2021/0187298 | A1 | 6/2021 | Dinsmoor et al. |

FOREIGN PATENT DOCUMENTS

| | | |
|---|---|---|
| EP | 2396072 B1 | 3/2013 |
| EP | 3013413 A1 | 5/2016 |
| EP | 3024540 B1 | 10/2018 |
| JP | 2018513714 A1 | 5/2018 |
| WO | 9405371 | 3/1994 |
| WO | 2002009808 A1 | 2/2002 |
| WO | 2010058178 A1 | 5/2010 |
| WO | 2012155188 A1 | 11/2012 |
| WO | 2014/210373 A1 | 12/2014 |
| WO | 2015070281 A1 | 5/2015 |
| WO | 2015143509 A1 | 10/2015 |
| WO | 2015179177 A1 | 11/2015 |
| WO | 2015179281 A2 | 11/2015 |
| WO | 2016011512 A1 | 1/2016 |
| WO | 2016090420 A1 | 6/2016 |
| WO | 2016090436 A1 | 6/2016 |
| WO | 2016191808 A1 | 12/2016 |
| WO | 2017100866 A1 | 6/2017 |
| WO | 2017106503 A1 | 6/2017 |
| WO | 2017173493 A1 | 10/2017 |
| WO | 2017184238 A1 | 10/2017 |
| WO | 2017219096 A1 | 12/2017 |
| WO | 2018/080754 A1 | 5/2018 |
| WO | 2018080753 A1 | 5/2018 |
| WO | 2018080754 A1 | 5/2018 |
| WO | 2018106813 A1 | 6/2018 |
| WO | 2019178634 A1 | 9/2019 |
| WO | 2019204884 A1 | 10/2019 |
| WO | 2019231794 A1 | 12/2019 |

OTHER PUBLICATIONS

Abejon MD, "Back Pain Coverage with Spinal Cord Stimulation: A Different Treatment for Each Patient," International Neuromodulation Society, 567, Jun. 10, 2015, Abstract Only, 1 pp.

Abeloos MD, "High Density Stimulation as an Alternative to Uncomfortable Cervical Tonic Spinal Cord Stimulation: Case Report," International Neuromodulation Society 12th World Congress, Jun. 11-15, 2015, Abstract Only, 1 pp.

Breel et al., "High Density Stimulation: A Novel Programming Paradigm for the treatment of chronic pain," International Neuromodulation Society (INS) 12th World Congress; Jun. 9, 2015, Abstract Only, 1 pp.

Crosby et al., "Modulation of Activity and Conduction in Single Dorsal Column Axons by Kilohertz-Frequency Spinal Cord Stimulation," American Physiological Society, published online Oct. 19, 2016, 27 pp.

Cuellar MD PhD, et al., "Effect of High-Frequency Alternating Current on Spinal Afferent Nociceptive Transmission," Neuromodulation: Technology at the Neural Interface, vol. 16, No. 4, Jul.-Aug. 2013, pp. 318-327.

Cui et al., "Effect of Spinal Cord Stimulation on Tactile Hypersensitivity in Mononeuropathic Rats is Potentiated by Simultaneous GABA. Sub B. and Adenosine Receptor Activation," Neuroscience Letters 247, Apr. 1998, pp. 183-186.

Cui et al., "Spinal Cord Stimulation Attenuates Augmented Dorsal Horn Release of Excitatory Amino Acids in Mononeuropathy via a GABAergic Mechanism," Pain 73, Oct. 1997, pp. 87-95.

De Ridder et al., "Burst Spinal Cord Stimulation for Limb and Back Pain," World Neurosurgery, vol. 80, No. 5, Nov. 2013, pp. 642-649, e641.

De Ridder MD PhD et al., "Burst Spinal Cord Stimulation: Toward Paresthesia-Free Pain Suppression," Neurosurgery, vol. 66, No. 5, May 2010, pp. 986-990.

Downey, "Asynchronous Neuromuscular Electrical Stimulation," University of Florida, 2015, accessed on Jul. 18, 2016, 107 pp.

Duyvendak MD et al., "High Density Stimulation: a Novel Programming Paradigm for the Treatment of Chronic Back and Leg Pain," Abstracts, International Neuromodulation Society 12th World Congress: Jun. 11-15, 2015, 1 pp.

Gao et al., "Effects of Spinal Cord Stimulation with "Standard Clinical" and Higher Frequencies on Peripheral Blood Flow in Rats," Brain Research, available online Dec. 3, 2009, pp. 53-61.

Grider DO/PhD et al., "High Frequency (1000 Hz) Stimulation Using Commercially Available Implantable Pulse Generator," North American Neuromodulation Society, Dec. 2013, Abstract Only, 2 pp.

Guan MD PhD et al., "Spinal Cord Stimulation-Induced Analgesia: Electrical Stimulation of Dorsal Column and Dorsal Roots Attenuates Dorsal Horn Neuronal Excitability in Neuropathic Rats," Anesthesiology, vol. 113, No. 6, Dec. 2010, pp. 1392-1405.

Guan, "Spinal Cord Stimulation: Neurophysiological and Neurochemical Mechanisms of Action" Current Pain and Headache Reports, Mar. 8, 2012, pp. 217-225.

Holsheimer, "Computer Modelling of Spinal Cord Stimulation and its Contribution to Therapeutic Efficacy," Spinal Cord, Aug. 1998, pp. 531-540.

Hubscher et al., "Convergence and Cross Talk in Urogenital Neural Circuitries," Journal of Neurophysiology, vol. 110, Aug. 7, 2013, 9 pp.

Hunt et al. "The Molecular Dynamics of Pain Control," Nature Reviews Neuroscience, vol. 2, Feb. 2001, pp. 83-91.

Kemler MD et al., "Spinal Cord Stimulation in Patients with Chronic Reflex Sympathetic Dystrophy," New England Journal of Medicine, vol. 343, No. 9, Aug. 31, 2000, pp. 618-624.

Kilgore PhD et al., "Reversible Nerve Conduction Block Using Kilohertz Frequency Alternating Current," Neuromodulation, Aug. 2013, pp. 242-255.

Kumar et al., "Spinal Cord Stimulation Versus Conventional Medical Management for Neuropathic Pain: a Multicentre Randomised Controlled Trial in Patients with Failed Back Surgery Syndrome," Pain, vol. 132, Jul. 2007, 179-188.

Likar et al., "High Density Spinal Cord Stimulation: a Multi-Center Experience," Abstracts, International Neuromodulation Society 12th World Congress, Jun. 11-15, 2015, 1 pp.

Maeda et al., "Increased c-fos Immunoreactivity in the Spinal Cord and Brain Following Spinal Cord Stimulation is Frequency-Dependent," Brain Research, Mar. 9, 2009, pp. 40-50.

Maeda et al., "Low Frequencies, But Not High Frequencies of Bi-Polar Spinal Cord Stimulation Reduce Cutaneous and Muscle Hyperalgesia Induced by Nerve Injury," Pain, vol. 138, No. 1, Feb. 2008, pp. 143-152.

Maggi et al., "Effect of Urethane Anesthesia on the Micturition Reflex in Capsaicin~Treated Rats," Journal of the Autonomic Nervous System, vol. 30, No. 3, Jan. 1990, pp. 247-251.

North MD et al., "Clinical Outcomes of 1 kHz Subperception Spinal Cord Stimulation (SCS): Results of a Prospective Randomized Controlled Crossover Trial," Abstracts, International Neuromodulation Society, Jun. 2015, 1 pp.

(56) References Cited

OTHER PUBLICATIONS

North MD et al., "Spinal Cord Stimulation Versus Repeated Lumbosacral Spine Surgery for Chronic Pain: a Randomized, Controlled Trial," Neurosurgery, vol. 56, No. 1, Jan. 2005 pp. 98-106: discussion 106-107.
Ranck Jr. et al., "Which Elements are Excited in Electrical Stimulation of Mammalian Central Nervous System: a Review," Brain Research, vol. 98, No. 3, Nov. 21, 1975, pp. 417-440.
Replogle MD. et al., "Case Series Comparing Moderate (1000 Hz) Versus Conventional Frequency Stimulation During Spinal Cord Stimulator Trials," North American Neuromodulation Society, 2014 (Applicant points out in accordance with MPEP 609.04(a) that the 2014 year of publication is sufficiently earlier than the effective U.S. filing date of the present application, and any foreign priority date that the particular month of publication is not in issue), 1 pp.
Sato et al., "Spinal Cord Stimulation Reduces Hypersensitivity Through Activation of Opioid Receptors in a Frequency-Dependent Manner," European Journal of Pain, vol. 17, No. 4, Apr. 2013, pp. 551-561, first published Oct. 5, 2012.
Schu MD, PhD. et al., "A Prospective, Randomised, Double-Blind, Placebo-Controlled Study to Examine the Effectiveness of Burst Spinal Cord Stimulation Patterns for the Treatment of Failed Back Surgery Syndrome," Neuromodulation, vol. 17, No. 5, Apr. 2014, pp. 443-450.
Shechter MD et al., "Conventional and Kilohertz-Frequency Spinal Cord Stimulation Produces Intensity-and Frequency-Dependent Inhibition of Mechnical Hypersensitivity in a Rat Model of Neuropathic Pain," Anesthesiology, vol. 119, No. 2, Aug. 2013, pp. 422-432.
Sluka, et al., "High-Frequency, But Not Low-Frequency, Transcutaneous Electrical Nerve Stimulation Reduces Aspartate and Glutamate Release in the Spinal Cord Dorsal Horn," Journal of Neurochemistry, vol. 95, No. 6, Oct. 17, 2005, pp. 1794-1801.
Smith et al., "Successful Use of High-Frequency Spinal Cord Stimulation Following Traditional Treatment Failure," Stereotactic and Functional Neurosurgery, vol. 93, No. 3, Apr. 1, 2015, pp. 190-193.
Snellings et al., "Effects of Stimulation Site and Stimulation Parameters on Bladder Inhibition by Electrical Nerve Stimulation," BJU International, Jul. 2012, pp. 136-143, first published Jan. 19, 2012.
Song MD Phd. et al., "Efficacy of Kilohertz-Frequency and Conventional Spinal Cord Stimulation in Rat Models of Different Pain Conditions," Neuromodulation, vol. 17, No. 3, Jan. 2014, pp. 226-234.
Sweet MD et al., "High Frequency vs. Burst Stimulation Patterns for Dorsal Column Stimulation: The Importance of Charge," American Association of Neurological Surgeons, Abstract, Apr. 4, 2014, 2 pp.
Walter et al., "Inhibiting the Hyperreflexic Bladder with Electrical Stimulation in a Spinal Animal Model," Neurourology and Urodynamics, vol. 12, No. 2,1993 (Applicant points out in accordance with MPEP 609.04(a) that the 1993 year of publication is sufficiently earlier than the effective U.S. filing date of the present application, and any foreign priority date that the particular month of publication is not in issue) pp. 241-253.
Wille MD et al., "Altering Conventional to High Density Spinal Cord Stimulation: An Energy Dose-Response Relationship in Neuropathic Pain Therapy," Neuromodulation 2016, Aug. 2016, 9 pp.
Woock et al., "Activation and Inhibition of the Micturition Reflex by Penile Afferents in the Cat," American Journal of Physiology—Regulatory, Intergregrative and Comparative Physiology, published Apr. 23, 2008, pp. R1880-R1889.
Youn et al., "The Effect of High Frequency Stimulation on Sensory Thresholds in Chronic Pain Patients," North American Neuromodulation Society, 2014 (Applicant points out in accordance with MPEP 609.04(a) that the 2014 year of publication is sufficiently earlier than the effective U.S. filing date of the present application, and any foreign priority date that the particular month of publication is not in issue) 1 pp.
U.S. Appl. No. 17/065,383, by Medtronic, Inc. (Inventors: Dinsmoor et al.), filed Oct. 7, 2020.
U.S. Appl. No. 17/065,282, by Medtronic, Inc. (Inventors: Dinsmoor et al.), filed Oct. 7, 2020.
Agnesi et al., "Local Glutamate Release in the Rat Ventral Lateral Thalamus Evoked by High-Frequency Stimulation," Journal of Neural Engineering, vol. 7, No. 2, Apr. 2010, 20 pp.
Vallejo et al., "Effects of Phase Polarity and Charge Balance Spinal Cord Stimulation on Behavior and Gene Expression in a Rat Model of Neuropathic Pain," Neuromodulation: Technology at the Neural Interface, vol. 23, No. 1, Apr. 2019, 10 pp.
Youn et al., "The Effect of High-Frequency Stimulation on Sensory Thresholds in Chronic Pain Patients," Stereotactic and Functional Neurosurgery, Oct. 8, 2015, pp. 355-359.
U.S. Appl. No. 17/183,997, filed Feb. 24, 2021, by Bourget et al.
U.S. Appl. No. 17/184,196, filed Feb. 24, 2021, by Bourget et al.
U.S. Appl. No. 16/721,528, filed Dec. 19, 2019, naming inventors Dinsmoor et al.
U.S. Appl. No. 16/721,576, filed Dec. 19, 2019, naming inventors Dinsmoor et al.
U.S. Appl. No. 17/065,383, filed Oct. 7, 2020, naming inventors Dinsmoor et al.
Laird-Wah, "Improving Spinal Cord Stimulation Model-Based Approaches to Evoked Response Telemetry," Aug. 2015, 273 pp.
Shariati et al., "Evaluating Spinal Cord Stimulation incorporating feedback control using Evoked Compound Action Potential," Saluda Medical, Dec. 2, 2014, 1 pp.
International Search Report and Written Opinion of International Application No. PCT/US2021/036815, dated Sep. 9, 2021, 14 pp.
International Preliminary Report on Patentability from International Application No. PCT/US2021/036815 dated Dec. 22, 2022, 11 pp.

\* cited by examiner

MANAGING STORAGE OF SENSED INFORMATION

This application claims the benefit of U.S. Provisional Patent Application No. 63/037,406, filed Jun. 10, 2020, the entire content of which is incorporated herein by reference.

TECHNICAL FIELD

This disclosure generally relates to medical devices, and more specifically, information collected by medical devices.

BACKGROUND

Medical devices may be external or implanted and may be used to deliver electrical stimulation therapy to patients via various tissue sites to treat a variety of symptoms or conditions such as chronic pain, tremor, Parkinson's disease, epilepsy, urinary or fecal incontinence, sexual dysfunction, obesity, or gastroparesis. A medical device may deliver electrical stimulation therapy via one or more leads that include electrodes located proximate to target locations associated with the brain, the spinal cord, pelvic nerves, peripheral nerves, or the gastrointestinal tract of a patient. Stimulation proximate the spinal cord, proximate the sacral nerve, within the brain, and proximate peripheral nerves are often referred to as spinal cord stimulation (SCS), sacral neuromodulation (SNM), deep brain stimulation (DBS), and peripheral nerve stimulation (PNS), respectively.

An evoked compound action potential (ECAP) is synchronous firing of a population of neurons which occurs in response to the application of a stimulus including, in some cases, an electrical stimulus by a medical device. The ECAP may be detectable as being a separate event from the stimulus itself, and the ECAP may reveal characteristics of the effect of the stimulus on the nerve fibers. Electrical stimulation may be delivered to a patient by the medical device in a train of electrical pulses, and parameters of the electrical pulses may include a frequency, an amplitude, a pulse width, and a pulse shape. The parameters of the electrical pulses may be altered in response to sensory input, such as ECAPs sensed in response to the train of electrical pulses. Such alterations may affect the patient's perception of the electrical pulses, or lack thereof.

SUMMARY

In general, the disclosure is directed to devices, systems, and techniques for managing storage of sensed information. An implantable medical device (IMD) may sense a variety of information related to a patient. For example, an IMD may sense a plurality of evoked compound action potential (ECAP) signals. These ECAP signals are physiological signals that are elicited in response to the delivery of an electrical stimulus (e.g., a stimulation pulse). The IMD may monitor one or more characteristics of the ECAP signals and adjust electrical stimulation based on the one or more characteristics. In some examples, more information regarding the ECAP signals may be useful for further investigation into patient activity, patient symptom and/or patient disease progression, or efficacy of electrical stimulation therapy.

The IMD, or other device, may store ECAP information in a memory in response to receiving a trigger signal that requests long-term storage of at least a portion of the ECAP information. This ECAP information may include multiple characteristics and/or a waveform representative of the sensed ECAP signals. In addition, or alternatively, the IMD may increase the rate at which the IMD senses ECAP signals. The IMD may also store a marker indicating the timing of the trigger signal with respect to the stored ECAP information. The trigger signal may be a user input indicating a patient event, a characteristic of an ECAP signal exceeding a threshold, a user requested change to one or more stimulation parameters that define electrical stimulation, or any other type of event.

In some examples, a system includes a memory and processing circuitry configured to receive evoked compound action potential (ECAP) information, wherein the ECAP information comprises information from a plurality of evoked compound action potential (ECAP) signals, receive a trigger signal requesting long-term storage of at least a portion of the ECAP information in the memory, and responsive to receiving the trigger signal, store the at least portion of the ECAP information in the memory In some examples, a method includes receiving, by processing circuitry, evoked compound action potential (ECAP) information, wherein the ECAP information comprises information from a plurality of evoked compound action potential (ECAP) signals, receiving, by the processing circuitry, a trigger signal requesting long-term storage of at least a portion of the ECAP information in a memory, and responsive to receiving the trigger signal, storing, by the processing circuitry, the at least portion of the ECAP information in the memory.

In some examples, a computer-readable medium includes instructions that, when executed by a processor, causes the processor to receive evoked compound action potential (ECAP) information, wherein the ECAP information comprises information from a plurality of evoked compound action potential (ECAP) signals, receive a trigger signal requesting long-term storage of at least a portion of the ECAP information in a memory, and responsive to receiving the trigger signal, store the at least portion of the ECAP information in the memory.

The summary is intended to provide an overview of the subject matter described in this disclosure. It is not intended to provide an exclusive or exhaustive explanation of the systems, device, and methods described in detail within the accompanying drawings and description below. Further details of one or more examples of this disclosure are set forth in the accompanying drawings and in the description below. Other features, objects, and advantages will be apparent from the description and drawings, and from the claims.

BRIEF DESCRIPTION OF DRAWINGS

Like reference characters denote like elements throughout the description and figures.

DETAILED DESCRIPTION

Figure 1:
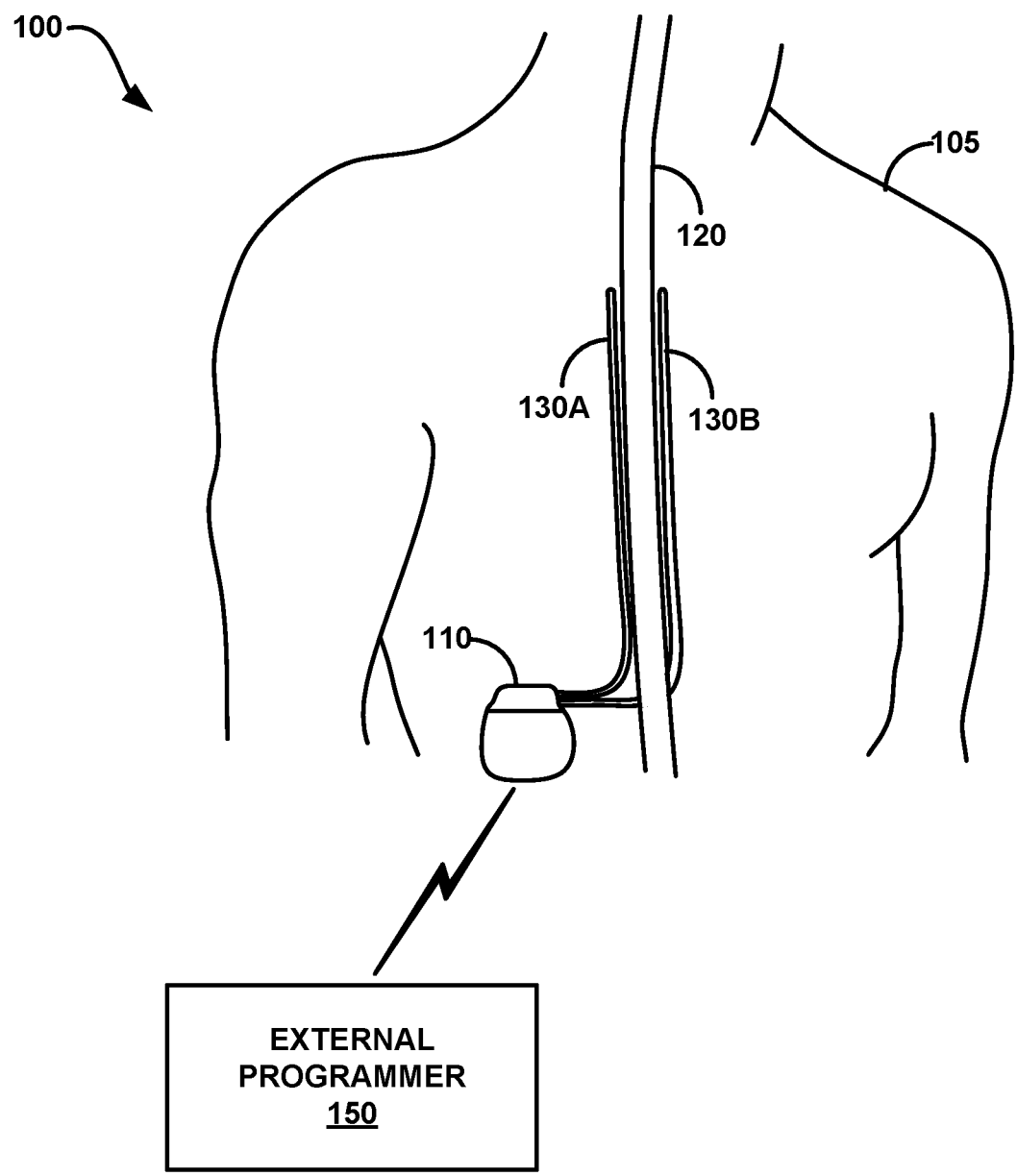
FIG. 1 is a conceptual diagram illustrating an example system that includes an implantable medical device (IMD) configured to deliver spinal cord stimulation (SCS) therapy and an external programmer, in accordance with one or more techniques of this disclosure.

The disclosure describes examples of medical devices, systems, and techniques for managing the storage of sensed information, such as ECAP information. Electrical stimulation therapy is typically delivered to a target tissue (e.g., one or more nerves or muscle) of a patient via two or more electrodes. Parameters that define the electrical stimulation therapy (e.g., electrode combination, voltage or current amplitude, pulse width, pulse frequency, duty cycle, etc.) are selected by a clinician and/or the patient to provide relief from various symptoms, such as pain, muscle disorders, etc.

However, as the patient moves, the distance between the electrodes and the target tissues changes. Posture changes or patient activity can cause electrodes to move closer or farther from target nerves. Lead migration over time may also change this distance between electrodes and target tissue. In some examples, a patient event may include transient patient conditions such as coughing, sneezing, laughing, Valsalva maneuvers, leg lifting, cervical motions, or deep breathing that may temporarily cause the stimulation electrodes of the medical device to move closer to the target tissue of the patient. When the electrodes are closer to the nerves, the patient's perception of electrical stimulation therapy may change.

Since neural recruitment is a function of stimulation intensity and distance between the target tissue and the electrodes, movement of the electrode closer to the target tissue may result in increased perception by the patient (e.g., possible uncomfortable, undesired, or painful sensations), and movement of the electrode further from the target tissue may result in decreased efficacy of the therapy for the patient. For example, if stimulation is held consistent and the stimulation electrodes are moved closer to the target tissue, the patient may perceive the stimulation as more intense, uncomfortable, or even painful. Conversely, consistent stimulation while electrodes are moved farther from target tissue may result in the patient perceiving less intense stimulation which may reduce the therapeutic effect for the patient. Discomfort or pain caused by patient events that include transient patient conditions may be referred to herein as "transient overstimulation." Therefore, in some examples, it may be beneficial to adjust stimulation parameters in response to patent movement or other conditions that can cause transient overstimulation.

An ECAP may be evoked by a stimulation pulse delivered to nerve fibers of the patient. After being evoked, the ECAP may propagate down the nerve fibers away from the initial stimulus. Sensing circuitry of the medical device may, in some cases, detect this ECAP as an ECAP signal. Characteristics of the detected ECAP signal may indicate the distance between electrodes and target tissue is changing. For example, a sharp increase in ECAP amplitude over a short period of time (e.g., less than one second) may indicate that the distance between the electrodes and the target tissue is decreasing due to a transient patient action such as a cough. A gradual increase in ECAP amplitude over a longer period of time (e.g., days, weeks, or months) may indicate that the distance between the electrodes and the target tissue is decreasing due to long-term lead migration after the medical device is implanted. It may be beneficial to adjust one or more therapy parameter values in order to prevent the patient from experiencing uncomfortable sensations due to one or both of short-term movement of the electrodes relative to the target tissue and long-term movement of the electrodes relative to the target tissue.

In order to facilitate the sensing of ECAPs, in some examples, the medical device can deliver pulses as part of a therapy (e.g., informed pulses) and also deliver a plurality of control pulses that are designed to elicit detectable ECAPs when the informed pulses do not elicit detectable ECAPs. For example, the control pulse duration may be shorter than the informed pulse to reduce or eliminate the signal artifact that is caused by the informed pulse and prevents or limited detection of the ECAP received at a sensing electrodes). In particular embodiments, the control pulse is short enough that the pulse ends prior to the arrival of all, or most, of the ECAP at the sensing electrode(s). In this manner, the medical device may interleave the plurality of control pulses with at least some informed pulses of the plurality of informed pulses. For example, the medical device may deliver informed pulses for a period of time before delivering a control pulse and sensing the corresponding ECAP (if any). The medical device can then resume delivery of the informed pulses for another period of time. In some examples, a pulse duration of the control pulses is less than a pulse duration of the informed pulses and the pulse duration of the control pulses is short enough so that the medical device can sense an individual ECAP for each control pulse. In some examples, the control pulses may provide or contribute to the therapy perceived by the patient.

In some examples, the medical device can use a characteristic value that represents the sensed ECAP signal to adjust one or more parameter values that defines electrical stimulation. The characteristic value may be an amplitude value, slope of one or more peaks, area under one or more peaks of the ECAP signal, or any other value that characterizes the magnitude of the sensed ECAP signal. Although the medical device may use the characteristic value of the ECAP signal, the medical device may not store the characteristics of the respective ECAP signals or the ECAP signals themselves. Continuous storage of this ECAP information may be impractical due to limited memory capacity for data within the medical device and/or increased power consumption requires to continually process and store the ECAP information. In addition, this large amount of ECAP information may be too large for a clinician to review for pertinent information related to the patient.

As described herein, devices, systems, and techniques may be configured to manage storage of sensed information. The IMD may monitor one or more characteristics of the ECAP signals over time, and the IMD may, or may not, adjust one or more parameters that at least partially define electrical stimulation. In either case, the IMD may selectively store information representative of the sensed ECAP signals. This information may be useful for further investigation into patient activity, monitoring patient symptom and/or patient disease progression, or determining efficacy of electrical stimulation therapy over time, as some examples.

The ECAP information representing the sensed ECAP signals may include one or more various types of information. For example, the ECAP information may include one or more characteristics indicative of the magnitude of respective ECAP signals. These characteristics may be an amplitude between two peaks in the ECAP signal, an area under one or more peaks of the ECAP signal, a steepness of one or more slopes of the ECAP signal, or other such aspects of the ECAP signal. In addition, or alternatively, the ECAP information may include a waveform representative of the sensed ECAP signals.

The IMD, or another device separate from the IMD, may store the ECAP information in a memory in response to receiving a trigger signal that requests long-term storage of at least a portion of the ECAP information. This memory may be a long-term memory that is different from a temporary memory that stores the ECAP information only for a short period of time. For example, the temporary memory may be a first-in-first-out (FIFO) memory or other rolling memory that only stores the ECAP information for a predetermined period of time or a predetermined amount of data. In addition, or alternatively, to storing the IMD information permanently (e.g., until the ECAP information can be transmitted to another device) the IMD may adjust other ECAP related collection functions, such as increase a sample rate of the ECAP signals and/or increase the rate at which the IMD senses ECAP signals.

In some example, the IMD may store a marker (e.g., a timestamp) indicating the timing of the trigger signal with respect to the stored ECAP information. In this manner, the ECAP information may be analyzed with respect to the timing of an event associated with the trigger signal. The trigger signal may be a user input indicating a patient event, a characteristic of an ECAP signal exceeding a threshold, a user requested change to one or more stimulation parameters that define electrical stimulation, or any other type of event.

The devices, systems, and techniques described herein may provide one or more advantages. For example, storing ECAP information in response to receiving a trigger signal may enable the storage of high fidelity ECAP information that would not be able to be otherwise stored continuously. A marker associated with the trigger signal being stored with the ECAP information may also enable the analysis of the ECAP information with respect to the event that elicited the trigger signal. In addition, storing and/or capturing higher fidelity ECAP information (e.g., information from more frequently sensed ECAP signals) in response to the trigger signal may enable improved analysis capabilities for the system while conserving battery power when such higher fidelity ECAP information is not needed for therapy and/or later analysis. In some examples, the system may store this higher fidelity ECAP information as part of a trial stimulation period in which the clinician and patient can evaluate whether or not electrical stimulation can provide effective treatment of the patient's conditions.

In some examples, the IMD may deliver stimulation that includes pulses (e.g., control pulses) that contribute to therapy and also elicit detectable ECAP signals. In other examples, the IMD may deliver the stimulation pulses to include control pulses and informed pulses. Nerve impulses detectable as the ECAP signal travel quickly along the nerve fiber after the delivered stimulation pulse first depolarizes the nerve. Therefore, if the stimulation pulse delivered by first electrodes has a pulse width that is too long, different electrodes configured to sense the ECAP will sense the stimulation pulse itself as an artifact that obscures the lower amplitude ECAP signal. However, the ECAP signal loses fidelity as the electrical potentials propagate from the electrical stimulus because different nerve fibers propagate electrical potentials at different speeds. Therefore, sensing the ECAP at a far distance from the stimulating electrodes may avoid the artifact caused by a stimulation pulse with a long pulse width, but the ECAP signal may lose fidelity needed to detect changes to the ECAP signal that occur when the electrode to target tissue distance changes. In other words, the system may not be able to identify, at any distance from the stimulation electrodes, ECAPs from stimulation pulses configured to provide a therapy to the patient. Therefore, the IMD may employ control pulses configured to elicit detectable ECAPs and informed pulses that may contribute to therapeutic effects for the patient by may not elicit detectable ECAPs.

In these examples, a IMD is configured to deliver a plurality of informed pulses configured to provide a therapy to the patient and a plurality of control pulses that may or may not contribute to therapy. At least some of the control pulses may elicit a detectable ECAP signal without the primary purpose of providing a therapy to the patient. The control pulses may be interleaved with the delivery of the informed pulses. For example, the medical device may alternate the delivery of informed pulses with control pulses such that a control pulse is delivered, and an ECAP signal is sensed, between consecutive informed pulses. In some examples, multiple control pulses are delivered, and respective ECAP signals sensed, between the delivery of consecutive informed pulses. In some examples, multiple informed pulses will be delivered between consecutive control pulses. In any case, the informed pulses may be delivered according to a predetermined pulse frequency selected so that the informed pulses can produce a therapeutic result for the patient. One or more control pulses are then delivered, and the respective ECAP signals sensed, within one or more time windows between consecutive informed pulses delivered according to the predetermined pulse frequency. In this manner, a medical device can deliver informed pulses from the medical device uninterrupted while ECAP signals are sensed from control pulses delivered during times at which the informed pulses are not being delivered. In other examples described herein, ECAP signals are sensed by the medical device in response to the informed pulses delivered by the medical device, and control pulses are not used to elicit ECAPs.

Although electrical stimulation is generally described herein in the form of electrical stimulation pulses, electrical stimulation may be delivered in non-pulse form in other examples. For example, electrical stimulation may be delivered as a signal having various waveform shapes, frequencies, and amplitudes. Therefore, electrical stimulation in the form of a non-pulse signal may be a continuous signal than may have a sinusoidal waveform or other continuous waveform.

FIG. 1 is a conceptual diagram illustrating an example system 100 that includes an implantable medical device (IMD) 110 configured to deliver spinal cord stimulation (SCS) therapy, processing circuitry 140, and an external programmer 150, in accordance with one or more techniques of this disclosure. Although the techniques described in this disclosure are generally applicable to a variety of medical devices including external devices and IMDs, application of such techniques to IMDs and, more particularly, implantable electrical stimulators (e.g., neurostimulators) will be described for purposes of illustration. More particularly, the disclosure will refer to an implantable SCS system for purposes of illustration, but without limitation as to other types of medical devices or other therapeutic applications of medical devices.

As shown in FIG. 1, system 100 includes an IMD 110, leads 130A and 130B, and external programmer 150 shown in conjunction with a patient 105, who is ordinarily a human patient. In the example of FIG. 1, IMD 110 is an implantable electrical stimulator that is configured to generate and deliver electrical stimulation therapy to patient 105 via one or more electrodes of electrodes of leads 130A and/or 130B (collectively, "leads 130"), e.g., for relief of chronic pain or other symptoms. In other examples, IMD 110 may be coupled to a single lead carrying multiple electrodes or more than two leads each carrying multiple electrodes. As a part of delivering stimulation pulses of the electrical stimulation therapy, IMD 110 may be configured to generate and deliver control pulses configured to elicit ECAP signals. The control pulses may provide therapy in some examples. In other examples, IMD 110 may deliver informed pulses that contribute to the therapy for the patient, but which do not elicit detectable ECAPs. 1 MB 110 may be a chronic electrical stimulator that remains implanted within patient 105 for weeks, months, or even years. In other examples, IMD 110 may be a temporary, or trial, stimulator used to screen or evaluate the efficacy of electrical stimulation for chronic therapy. In one example, IMD 110 is implanted within patient 105, while in another example, IMD 110 is an external device coupled to percutaneously implanted leads. In some examples, IMD 110 uses one or more leads, while in other examples, IMD 110 is leadless.

IMD 110 may be constructed of any polymer, metal, or composite material sufficient to house the components of IMD 110 (e.g., components illustrated in FIG. 2) within patient 105. In this example, IMD 110 may be constructed with a biocompatible housing, such as titanium or stainless steel, or a polymeric material such as silicone, polyurethane, or a liquid crystal polymer, and surgically implanted at a site in patient 105 near the pelvis, abdomen, or buttocks. In other examples, IMD 110 may be implanted within other suitable sites within patient 105, which may depend, for example, on the target site within patient 105 for the delivery of electrical stimulation therapy. The outer housing of IMD 110 may be configured to provide a hermetic seal for components, such as a rechargeable or non-rechargeable power source. In addition, in some examples, the outer housing of 1 MB 110 is selected from a material that facilitates receiving energy to charge the rechargeable power source.

Electrical stimulation energy, which may be constant current or constant voltage-based pulses, for example, is delivered from IMD 110 to one or more target tissue sites of patient 105 via one or more electrodes (not shown) of implantable leads 130. In the example of FIG. 1, leads 130 carry electrodes that are placed adjacent to the target tissue of spinal cord 120. One or more of the electrodes may be disposed at a distal tip of a lead 130 and/or at other positions at intermediate points along the lead. Leads 130 may be implanted and coupled to 1 MB 110. The electrodes may transfer electrical stimulation generated by an electrical stimulation generator in 1 MB 110 to tissue of patient 105. Although leads 130 may each be a single lead, lead 130 may include a lead extension or other segments that may aid in implantation or positioning of lead 130. In some other examples, IMD 110 may be a leadless stimulator with one or more arrays of electrodes arranged on a housing of the stimulator rather than leads that extend from the housing. In addition, in some other examples, system 100 may include one lead or more than two leads, each coupled to IMD 110 and directed to similar or different target tissue sites.

The electrodes of leads 130 may be electrode pads on a paddle lead, circular (e.g., ring) electrodes surrounding the body of the lead, conformable electrodes, cuff electrodes, segmented electrodes (e.g., electrodes disposed at different circumferential positions around the lead instead of a continuous ring electrode), any combination thereof (e.g., ring electrodes and segmented electrodes) or any other type of electrodes capable of forming unipolar, bipolar or multipolar electrode combinations for therapy. Ring electrodes arranged at different axial positions at the distal ends of lead 130 will be described for purposes of illustration.

The deployment of electrodes via leads 130 is described for purposes of illustration, but arrays of electrodes may be deployed in different ways. For example, a housing associated with a leadless stimulator may carry arrays of electrodes, e.g., rows and/or columns (or other patterns), to which shifting operations may be applied. Such electrodes may be arranged as surface electrodes, ring electrodes, or protrusions. As a further alternative, electrode arrays may be formed by rows and/or columns of electrodes on one or more paddle leads. In some examples, electrode arrays include electrode segments, which are arranged at respective positions around a periphery of a lead, e.g., arranged in the form of one or more segmented rings around a circumference of a cylindrical lead. In other examples, one or more of leads 130 are linear leads having 8 ring electrodes along the axial length of the lead. In another example, the electrodes are segmented rings arranged in a linear fashion along the axial length of the lead and at the periphery of the lead.

The stimulation parameter of a therapy stimulation program that defines the stimulation pulses of electrical stimulation therapy by IMD 110 through the electrodes of leads 130 may include information identifying which electrodes have been selected for delivery of stimulation according to a stimulation program, the polarities of the selected electrodes, i.e., the electrode combination for the program, and voltage or current amplitude, pulse frequency, pulse width, pulse shape of stimulation delivered by the electrodes. These stimulation parameters of stimulation pulses (e.g., control pulses and/or informed pulses) are typically predetermined parameter values determined prior to delivery of the stimulation pulses (e.g., set according to a stimulation program). However, in some examples, system 100 changes one or more parameter values automatically based on one or more factors or based on user input.

An ECAP test stimulation program may define stimulation parameter values that define control pulses delivered by IMD 110 through at least some of the electrodes of leads 130. These stimulation parameter values may include information identifying which electrodes have been selected for delivery of control pulses, the polarities of the selected electrodes, i.e., the electrode combination for the program, and voltage or current amplitude, pulse frequency, pulse width, and pulse shape of stimulation delivered by the electrodes. The stimulation signals (e.g., one or more stimulation pulses or a continuous stimulation waveform) defined by the parameters of each ECAP test stimulation program are configured to evoke a compound action potential from nerves. In some examples, the ECAP test stimulation program defines when the control pulses are to be delivered to the patient based on the frequency and/or pulse width of the informed pulses when informed pulse are also delivered. In some examples, the stimulation defined by each ECAP test stimulation program are not intended to provide or contribute to therapy for the patient. In other examples, the stimulation defined by each ECAP test stimulation program may contribute to therapy when the control pulses elicit detectable ECAP signals and contribute to therapy. In this manner, the ECAP test stimulation program may define stimulation parameters the same or similar to the stimulation parameters of therapy stimulation programs.

Although FIG. 1 is directed to SCS therapy, e.g., used to treat pain, in other examples system 100 may be configured to treat any other condition that may benefit from electrical stimulation therapy. For example, system 100 may be used to treat tremor, Parkinson's disease, epilepsy, a pelvic floor disorder (e.g., urinary incontinence or other bladder dysfunction, fecal incontinence, pelvic pain, bowel dysfunction, or sexual dysfunction), obesity, gastroparesis, or psychiatric disorders (e.g., depression, mania, obsessive compulsive disorder, anxiety disorders, and the like). In this manner, system 100 may be configured to provide therapy taking the form of deep brain stimulation (DBS), peripheral nerve stimulation (PNS), peripheral nerve field stimulation (PNFS), cortical stimulation (CS), pelvic floor stimulation, gastrointestinal stimulation, or any other stimulation therapy capable of treating a condition of patient 105.

In some examples, lead 130 includes one or more sensors configured to allow IMD 110 to monitor one or more parameters of patient 105, such as patient activity, pressure, temperature, or other characteristics. The one or more sensors may be provided in addition to, or in place of, therapy delivery by lead 130.

IMD 110 is configured to deliver electrical stimulation therapy to patient 105 via selected combinations of electrodes carried by one or both of leads 130, alone or in combination with an electrode carried by or defined by an outer housing of IMD 110. The target tissue for the electrical stimulation therapy may be any tissue affected by electrical stimulation, which may be in the form of electrical stimulation pulses or continuous waveforms. In some examples, the target tissue includes nerves, smooth muscle or skeletal muscle. In the example illustrated by FIG. 1, the target tissue is tissue proximate spinal cord 120, such as within an intrathecal space or epidural space of spinal cord 120, or, in some examples, adjacent nerves that branch off spinal cord 120. Leads 130 may be introduced into spinal cord 120 in via any suitable region, such as the thoracic, cervical or lumbar regions. Stimulation of spinal cord 120 may, for example, prevent pain signals from traveling through spinal cord 120 and to the brain of patient 105. Patient 105 may perceive the interruption of pain signals as a reduction in pain and, therefore, efficacious therapy results. In other examples, stimulation of spinal cord 120 may produce paresthesia which may be reduce the perception of pain by patient 105, and thus, provide efficacious therapy results.

IMD 110 generates and delivers electrical stimulation therapy to a target stimulation site within patient 105 via the electrodes of leads 130 to patient 105 according to one or more therapy stimulation programs. A therapy stimulation program defines values for one or more parameters that define an aspect of the therapy delivered by IMD 110 according to that program. For example, a therapy stimulation program that controls delivery of stimulation by IMD 110 in the form of pulses may define values for voltage or current pulse amplitude, pulse width, and pulse rate (e.g., pulse frequency) for stimulation pulses delivered by IMD 110 according to that program.

In some examples where ECAP signals cannot be detected from the types of pulses intended to be delivered to provide therapy to the patient, control pulses and informed pulses may be delivered. For example, IMD 110 is configured to deliver control stimulation to patient 105 via a combination of electrodes of leads 130, alone or in combination with an electrode carried by or defined by an outer housing of IMD 110. The tissue targeted by the control stimulation may be the same tissue targeted by the electrical stimulation therapy, but IMD 110 may deliver control stimulation pulses via the same, at least some of the same, or different electrodes. Since control stimulation pulses are delivered in an interleaved manner with informed pulses, a clinician and/or user may select any desired electrode combination for informed pulses. Like the electrical stimulation therapy, the control stimulation may be in the form of electrical stimulation pulses or continuous waveforms. In one example, each control stimulation pulse may include a balanced, bi-phasic square pulse that employs an active recharge phase. However, in other examples, the control stimulation pulses may include a monophasic pulse followed by a passive recharge phase. In other examples, a control pulse may include an imbalanced bi-phasic portion and a passive recharge portion. Although not necessary, a bi-phasic control pulse may include an interphase interval between the positive and negative phase to promote propagation of the nerve impulse in response to the first phase of the bi-phasic pulse. The control stimulation may be delivered without interrupting the delivery of the electrical stimulation informed pulses, such as during the window between consecutive informed pulses. The control pulses may elicit an ECAP signal from the tissue, and IMD 110 may sense the ECAP signal via two or more electrodes on leads 130. In cases where the control stimulation pulses are applied to spinal cord 120, the signal may be sensed by IMD 110 from spinal cord 120.

IMD 110 may deliver control stimulation to a target stimulation site within patient 105 via the electrodes of leads 130 according to one or more ECAP test stimulation programs. The one or more ECAP test stimulation programs may be stored in a storage device of IMD 110. Each ECAP test program of the one or more ECAP test stimulation programs includes values for one or more parameters that define an aspect of the control stimulation delivered by IMD 110 according to that program, such as current or voltage amplitude, pulse width, pulse frequency, electrode combination, and, in some examples timing based on informed pulses to be delivered to patient 105. In some examples, IMD 110 delivers control stimulation to patient 105 according to multiple ECAP test stimulation programs.

A user, such as a clinician or patient 105, may interact with a user interface of an external programmer 150 to program IMD 110. Programming of IMD 110 may refer generally to the generation and transfer of commands, programs, or other information to control the operation of IMD 110. In this manner, IMD 110 may receive the transferred commands and programs from external programmer 150 to control electrical stimulation therapy (e.g., informed pulses) and control stimulation (e.g., control pulses). For example, external programmer 150 may transmit therapy stimulation programs, ECAP test stimulation programs, stimulation parameter adjustments, therapy stimulation program selections, ECAP test program selections, user input, or other information to control the operation of IMD 110, e.g., by wireless telemetry or wired connection. As described herein, stimulation delivered to the patient may include control pulses, and, in some examples, stimulation may include control pulses and informed pulses.

In some cases, external programmer 150 may be characterized as a physician or clinician programmer if it is primarily intended for use by a physician or clinician. In other cases, external programmer 150 may be characterized as a patient programmer if it is primarily intended for use by a patient. A patient programmer may be generally accessible to patient 105 and, in many cases, may be a portable device that may accompany patient 105 throughout the patient's daily routine. For example, a patient programmer may receive input from patient 105 when the patient wishes to terminate or change electrical stimulation therapy. In general, a physician or clinician programmer may support selection and generation of programs by a clinician for use by IMD 110, whereas a patient programmer may support adjustment and selection of such programs by a patient during ordinary use. In other examples, external programmer 150 may include, or be part of, an external charging device that recharges a power source of IMD 110. In this manner, a user may program and charge IMD 110 using one device, or multiple devices.

As described herein, information may be transmitted between external programmer 150 and IMD 110. Therefore, IMD 110 and external programmer 150 may communicate via wireless communication using any techniques known in the art. Examples of communication techniques may include, for example, radiofrequency (RF) telemetry and inductive coupling, but other techniques are also contemplated. In some examples, external programmer 150 includes a communication head that may be placed proximate to the patient's body near the IMD 110 implant site to improve the quality or security of communication between IMD 110 and external programmer 150. Communication between external programmer 150 and IMD 110 may occur during power transmission or separate from power transmission.

In some examples, IMD 110, in response to commands from external programmer 150, delivers electrical stimulation therapy according to a plurality of therapy stimulation programs to a target tissue site of the spinal cord 120 of patient 105 via electrodes (not depicted) on leads 130. In some examples, IMD 110 modifies therapy stimulation programs as therapy needs of patient 105 evolve over time. For example, the modification of the therapy stimulation programs may cause the adjustment of at least one parameter of the plurality of informed pulses. When patient 105 receives the same therapy for an extended period, the efficacy of the therapy may be reduced. In some cases, parameters of the plurality of informed pulses may be automatically updated.

Efficacy of electrical stimulation therapy may be indicated by one or more characteristics (e.g. an amplitude of or between one or more peaks or an area under the curve of one or more peaks) of an action potential that is evoked by a stimulation pulse delivered by IMD 110 (i.e., a characteristic of the ECAP signal). Electrical stimulation therapy delivery by leads 130 of IMD 110 may cause neurons within the target tissue to evoke a compound action potential that travels up and down the target tissue, eventually arriving at sensing electrodes of IMD 110. Furthermore, control stimulation may also elicit at least one ECAP, and ECAPs responsive to control stimulation may also be a surrogate for the effectiveness of the therapy. The amount of action potentials (e.g., number of neurons propagating action potential signals) that are evoked may be based on the various parameters of electrical stimulation pulses such as amplitude, pulse width, frequency, pulse shape (e.g., slew rate at the beginning and/or end of the pulse), etc. The slew rate may define the rate of change of the voltage and/or current amplitude of the pulse at the beginning and/or end of each pulse or each phase within the pulse. For example, a very high slew rate indicates a steep or even near vertical edge of the pulse, and a low slew rate indicates a longer ramp up (or ramp down) in the amplitude of the pulse. In some examples, these parameters contribute to an intensity of the electrical stimulation. In addition, a characteristic of the ECAP signal (e.g., an amplitude) may change based on the distance between the stimulation electrodes and the nerves subject to the electrical field produced by the delivered control stimulation pulses.

In one example, each therapy pulse may have a pulse width greater than approximately 300 µs, such as between approximately 300 µs and 1000 µs (i.e., 1 millisecond) in some examples. At these pulse widths, IMD 110 may not sufficiently detect an ECAP signal because the therapy pulse is also detected as an artifact that obscures the ECAP signal. If ECAPs are not adequately recorded, then ECAPs arriving at IMD 110 cannot be compared to the target ECAP characteristic (e.g. a target ECAP amplitude), and electrical therapy stimulation cannot be altered according to responsive ECAPs. When informed pulses have these longer pulse widths, IMD 110 may deliver control stimulation in the form of control pulses. The control pulses may have pulse widths of less than approximately 300 µs, such as a bi-phasic pulse with each phase having a duration of approximately 100 µs. Since the control pulses may have shorter pulse widths than the informed pulses, the ECAP signal may be sensed and identified following each control pulse and used to inform IMD 110 about any changes that should be made to the informed pulses (and control pulses in some examples). In general, the term "pulse width" refers to the collective duration of every phase, and interphase interval when appropriate, of a single pulse. A single pulse includes a single phase in some examples (i.e., a monophasic pulse) or two or more phases in other examples (e.g., a bi-phasic pulse or a tri-phasic pulse). The pulse width defines a period of time beginning with a start time of a first phase of the pulse and concluding with an end time of a last phase of the pulse (e.g., a biphasic pulse having a positive phase lasting 100 µs, a negative phase lasting 100 µs, and an interphase interval lasting 30 µs defines a pulse width of 230 µs). In another example, a control pulse may include a positive phase lasting 90 µs, a negative phase lasting 90 µs, and an interphase interval lasting 30 µs to define a pulse width of 210 µs In another example, a control pulse may include a positive phase lasting 120 µs, a negative phase lasting 120 µs, and an interphase interval lasting 30 µs to define a pulse width of 270 µs.

During delivery of control stimulation pulses defined by one or more ECAP test stimulation programs, IMD 110, via two or more electrodes interposed on leads 130, senses electrical potentials of tissue of the spinal cord 120 of patient 105 to measure the electrical activity of the tissue. IMD 110 senses ECAPs from the target tissue of patient 105, e.g., with electrodes on one or more leads 130 and associated sense circuitry. In some examples, IMD 110 receives a signal indicative of the ECAP from one or more sensors, e.g., one or more electrodes and circuitry, internal or external to patient 105. Such an example signal may include a signal indicating an ECAP of the tissue of patient 105. Examples of the one or more sensors include one or more sensors configured to measure a compound action potential of patient 105, or a physiological effect indicative of a compound action potential. For example, to measure a physiological effect indicative of a compound action potential, the one or more sensors may be an accelerometer, a pressure sensor, a bending sensor, a sensor configured to detect a posture of patient 105, or a sensor configured to detect a respiratory function of patient 105. In this manner, although the ECAP may be indicative of a posture change or other patient action, other sensors may also detect similar posture changes or movements using modalities separate from the ECAP. However, in other examples, external programmer 150 receives a signal indicating a compound action potential in the target tissue of patient 105 and transmits a notification to IMD 110.

The control stimulation parameters and the target ECAP characteristic values may be initially set at the clinic but may be set and/or adjusted at home by patient 105. Once the target ECAP characteristic values are set, the example techniques allow for automatic adjustment of therapy pulse parameters to maintain consistent volume of neural activation and consistent perception of therapy for the patient when the electrode-to-neuron distance changes. The ability to change the stimulation parameter values may also allow the therapy to have long term efficacy, with the ability to keep the intensity of the stimulation (e.g., as indicated by the ECAP) consistent by comparing the measured ECAP values to the target ECAP characteristic value. IMD 110 may perform these changes without intervention by a physician or patient 105.

In some examples, the system changes the target ECAP characteristic value over a period of time. The system may be programmed to change the target ECAP characteristic in order to adjust the intensity of informed pulses to provide varying sensations to the patient (e.g., increase or decrease the volume of neural activation). In one example, a system may be programmed to oscillate a target ECAP characteristic value between a maximum target ECAP characteristic value and a minimum target ECAP characteristic value at a predetermined frequency to provide a sensation to the patient that may be perceived as a wave or other sensation that may provide therapeutic relief for the patient. The maximum target ECAP characteristic value, the minimum target ECAP characteristic value, and the predetermined frequency may be stored in the storage device of IMD 110 and may be updated in response to a signal from external programmer 150 (e.g., a user request to change the values stored in the storage device of IMD 110). In other examples, the target ECAP characteristic value may be programed to steadily increase or steadily decrease to a baseline target ECAP characteristic value over a period of time. In other examples, external programmer 150 may program the target ECAP characteristic value to automatically change over time according to other predetermined functions or patterns. In other words, the target ECAP characteristic value may be programmed to change incrementally by a predetermined amount or predetermined percentage, the predetermined amount or percentage being selected according to a predetermined function (e.g., sinusoid function, ramp function, exponential function, logarithmic function, or the like). Increments in which the target ECAP characteristic value is changed may be changed for every certain number of pulses or a certain unit of time. Although the system may change the target ECAP characteristic value, received ECAP signals may still be used by the system to adjust one or more parameter values of the informed pulses and/or control pulses in order to meet the target ECAP characteristic value.

In some examples, IMD 110 includes stimulation generation circuitry configured to deliver electrical stimulation therapy to a patient, where the electrical stimulation therapy includes a plurality of informed pulses. Additionally, the stimulation generation circuitry of IMD 110 may be configured to deliver a plurality of control pulses, where the plurality of control pulses is interleaved with at least some informed pulses of the plurality of informed pulses. In some examples, IMD 110 includes sensing circuitry configured to detect a plurality of ECAPs, where the sensing circuitry is configured to detect each ECAP of the plurality of ECAPs after a control pulse of the plurality of control pulses and prior to a subsequent therapy pulse of the plurality of informed pulses. Even though the plurality of ECAPs may be received by IMD 110 based on IMD 110 delivering the plurality of control pulses (e.g., the plurality of control pulses may evoke the plurality of ECAPs received by IMD 110), the plurality of ECAPs may indicate an efficacy of the plurality of informed pulses. In other words, although the plurality of ECAPs might, in some cases, not be evoked by the plurality of informed pulses themselves, the plurality of ECAPs may still reveal one or more properties of the plurality of informed pulses or one or more effects of the plurality of informed pulses on patient 105. In some examples, the plurality of informed pulses are delivered by IMD 110 at above a perception threshold, where patient 105 is able to perceive the plurality of informed pulses delivered at above the perception threshold. In other examples, the plurality of informed pulses are delivered by IMD 110 at below a perception threshold, where the patient 105 not able to perceive the plurality of informed pulses delivered at below the perception threshold.

IMD 110 may include processing circuitry which, in some examples, is configured to process the plurality of ECAPs received by the sensing circuitry of IMD 110. For example, the processing circuitry of IMD 110 is configured to determine if a parameter of a first ECAP is greater than a threshold parameter value. The processing circuitry may monitor a characteristic value of each ECAP of the plurality of ECAPs and the first ECAP may be the first ECAP of the plurality of ECAPs recorded by IMD 110 that exceeds the threshold characteristic value. In some examples, the characteristic monitored by IMD 110 may be an ECAP amplitude. The ECAP amplitude may, in some examples, be given by a voltage difference between an N1 ECAP peak and a P2 ECAP peak. More description related to the N1 ECAP peak, the N2 ECAP peak, and other ECAP peaks may be found below in the FIG. 4 description. In other examples, IMD 110 may monitor another characteristic or more than one characteristic of the plurality of ECAPs, such as current amplitude, slope, slew rate, ECAP frequency, ECAP duration, or any combination thereof. In some examples where the characteristic includes an ECAP amplitude, the threshold ECAP characteristic value may be selected from a range of approximately 5 microvolts (µV) to approximately 30 µV. These characteristics may be stored as ECAP information in a temporary memory and may, in response to receiving a trigger signal, be stored by IMD 110 in a long-term memory for later analysis and/or transmission to another device.

If the processing circuitry of IMD 110 determines that the characteristic of the first ECAP is greater than the threshold ECAP characteristic value, the processing circuitry may decrement (or reduce) a parameter of a set of informed pulses delivered by the stimulation generation circuitry after the first ECAP. In some examples, in order to decrement the parameter of the set of informed pulses, IMD 110 may decrease a current amplitude of each therapy pulse of each consecutive therapy pulse of the set of informed pulses by a current amplitude value. In other examples, in order to decrement the parameter of the set of informed pulses, IMD 110 may decrease a magnitude of a parameter (e.g., voltage) other than current. Since the plurality of ECAPs may indicate some effects of the therapy delivered by IMD 110 on patient 105, IMD 110 may decrement the parameter of the set of informed pulses in order to improve the therapy delivered to patient 105. In some cases, ECAPs received by IMD 110 exceeding the threshold ECAP characteristic value may indicate to IMD 110 that one or more of leads 130 have moved closer to the target tissue (e.g., spinal cord 120) of patient 105. In these cases, if therapy delivered to spinal cord 120 is maintained at present levels, patient 105 may experience transient overstimulation since the distance between leads 130 and the target tissue of patient 105 is a factor in determining the effects of electrical stimulation therapy on patient 105. Consequently, decrementing the first set of informed pulses based on determining that the first ECAP exceeds the threshold ECAP characteristic value may prevent patient 105 from experiencing transient overstimulation due to the electrical stimulation therapy delivered by IMD 110.

After determining that the first ECAP exceeds the threshold ECAP characteristic value, the processing circuitry of IMD 110 may continue to monitor the plurality of ECAPs detected by the sensing circuitry. In some examples, the processing circuitry of IMD 110 may identify a second ECAP which occurs after the first ECAP, where a characteristic of the second ECAP is less than the threshold ECAP characteristic value. The second ECAP may, in some cases, be a leading ECAP occurring after the first ECAP which includes a characteristic value less than the threshold ECAP characteristic value. In other words, each ECAP occurring between the first ECAP and the second ECAP may include a characteristic value greater than or equal to the threshold ECAP characteristic value. In this manner, since IMD 110 may decrement the informed pulses delivered to patient 105 between the first ECAP and the second ECAP, decreasing a risk that patient 105 experiences transient overstimulation during a period of time extending between the reception of the first ECAP and the reception of the second ECAP. Based on the characteristic of the second ECAP being less than the threshold ECAP characteristic value, the processing circuitry of IMD 110 may increment a parameter of a second set of informed pulses delivered by the stimulation generation circuitry after the second ECAP.

As described herein, system 100 may include a memory and processing circuitry. For example, IMD 110 and/or external programmer 150 may include some or all of the processing circuitry configured to perform various functions. System 100 may be configured to receive ECAP information, wherein the ECAP information comprises information from a plurality of ECAP signals, receive a trigger signal requesting long-term storage of at least a portion of the ECAP information in the memory, and responsive to receiving the trigger signal, store the at least portion of the ECAP information in the memory. Stimulation generation circuitry of IMD 110 may be configured to deliver electrical stimulation to a patient, wherein the electrical stimulation therapy comprises a plurality of stimulation pulses, and sensing circuitry of IMD 110 or another device may be configured to sense the plurality of ECAP signals. The sensing circuitry may be configured to sense each ECAP signal of the plurality of ECAP signals elicited by a respective stimulation pulse of the plurality of stimulation pulses, and the processing circuitry may be configured to receive the ECAP signals from the sensing circuitry as the ECAP information.

The ECAP information may include at least one characteristic value representing respective ECAP signals of the plurality of ECAP signals. The characteristic value may be at least one of an amplitude value, a slope value, or an area under peak value indicative of a respective ECAP signal. Since the ECAP signal represents the action potential from a plurality of nerves, where a stronger ECAP signal indicates activation of a greater number of nerves, the characteristic value may similarly be indicative of the number of activated nerves from the delivery of a stimulation pulse. In addition, or alternatively, the ECAP information may include a plurality of waveforms representing respective ECAP signals of the plurality of ECAP signals. This waveform may be analog or a digitized representation of an analog waveform of each ECAP signal. In this manner, the waveform being stored may represent the sensed ECAP signal from tissue over time as opposed to a value calculated from the waveform (such as an amplitude between two peaks of the ECAP waveform). In this manner, the ECAP information may include any type of information or data representing one or more sensed ECAP signals. Storing waveform information may be a higher fidelity type of information when compared to other characteristic values representing the ECAP signal.

System 100 may take different actions in response to receiving a trigger signal that requests long-term storage of at least a portion of the ECAP information. For example, system 100 may initially store received ECAP information in a temporary memory. In response to receiving the trigger signal, system 100 may store the ECAP information initially stored in the temporary memory in a long-term memory. System 100 may thus transfer the ECAP information to the long-term memory. In this manner, the temporary memory may act like a buffer so that system 100 can store, if needed, ECAP information received prior to the trigger signal in the long-term memory. In some examples, system 100 may be configured to delete the ECAP information stored in the temporary memory in response to a predetermined period of time elapsing. The predetermined period of time may be selected to be between a fraction of a second (e.g., one millisecond or one microsecond) and several hours, for example. In one example, the predetermined period of time may be between 20 seconds and 5 minutes. In other words, the temporary memory may have a buffer length from approximately 20 seconds to 5 minutes. For example, the buffer length may be 30 seconds or 60 seconds. In another example, the buffer may be less than or equal to two minutes. Other buffer lengths shorter or longer may be used in other examples. This time may elapse prior to receiving the trigger signal. System 100 may thus delete ECAP information from the temporary memory when not needed. These types of temporary memories may be similar to a first-in-first-out type of memory or buffer.

In other some examples, system 100 may be configured to, responsive to receiving the trigger signal, control the sensing circuitry to increase a rate at which the sensing circuitry senses subsequent ECAP signals and store subsequent ECAP information comprising the subsequent ECAP signals in the memory. In this manner, system 100 may also increase the rate at which the stimulation generation circuitry generates stimulation pulses from which the increased rate of ECAP signals are sensed because typically one ECAP signal is sensed from one respective stimulation pulse. By increasing the rate of ECAP signal detection, system 100 may increase the fidelity of ECAP information in response to receiving the trigger signal.

The trigger signal may take any number of forms. For example, the trigger signal may include a request from an external device (e.g., external programmer 150 such as a patient programmer or clinician programmer) to store the ECAP information. A user may interact with the external device and request that the external device transmit a request to IMD 110 to store the ECAP information for long-term storage. In this manner, IMD 110 may receive the trigger signal from the external device. In other examples, IMD 110 may receive a user request directly from the user, such as a housing tap in which the patient taps the housing of IMD 110 through the skin of the patient. IMD 110 may include one or more accelerometers or other motion detection or presence detection devices configured to detect tapping on the housing. Therefore, IMD 110 may be configured to receive or detect the housing tap by receiving accelerometer data from an accelerometer within the housing of IMD 110 and determining that the accelerometer data indicates the user tapped IMD 110. IMD 110 may employ a specific tapping algorithm to differentiate the tap from other movements or motions. For example, IMD 110 may need to detect a specific pattern of tapping, number of taps, magnitude of one or more tapes, or any other type of housing tap that would be different from other routine bumps and movements to IMD 110.

In other examples, the trigger signal includes an indication that a characteristic of one ECAP signal of the plurality of ECAP signals exceeds a threshold. The threshold may indicate that a particular movement of patient 105 (e.g., coughing, sneezing, laughing, bending over, etc.) may have caused an undesirable sensation from stimulation, where further analysis of the ECAP signals may be desired. In some examples, the trigger signal may include an indication that a user changed one or more stimulation parameter values defining electrical stimulation deliverable to a patient. User changing of a stimulation parameter may indicate ineffective therapy and/or undesirable sensations felt by patient 105, so ECAP information related to such an event may be beneficial for further analysis into what may have caused the patient to change the stimulation parameter value.

In some examples, system 100 may select specific portions of ECAP information according to the trigger signal. For example, in response to receiving the trigger signal, system 100 may select the at least portion of the ECAP information representative of one or more ECAP signals of the plurality of ECAP signals sensed between an initial time and a final time. The initial time may occur at a first period of time prior to receiving the trigger signal, and the final time may occur at a second period of time after receiving the trigger signal. In this manner, system 100 may store, in the long-term memory, ECAP information recorded and received prior to the trigger event and ECAP information following the trigger event. The resulting stored ECAP information may include information representative of ECAP signals sensed before and after the event which caused the trigger signal to be generated. In this manner, the system may enable capture of ECAP information leading up to an identified trigger signal. For a user, this may result in the patient being able to record ECAP information that was captured prior to feeling a sensation that causes the patient to desire to store the ECAP information and/or prior to the patient being able to provide the input request to the programmer. Additionally, the process prevents the system or user from being able to anticipate which ECAP information may be relevant prior to some event occurring.

In some examples, system 100 may move ECAP information stored in the temporary memory before receiving the trigger signal into the long-term memory and then store ECAP information received after the trigger signal directly into the long-term memory. In other examples, system 100 may store all received ECAP information in the temporary memory first and then move that ECAP information representative of ECAP signals sensed between the initial time and the final time to the long-term memory. In some examples, system 100 may add a marker representative of the trigger signal to the at least portion of the ECAP information stored in the memory. The marker may indicate a time of the trigger signal with respect to sensed ECAP signals of the ECAP information. In addition, or alternatively, the marker may include information identifying the type of event (e.g., a user request, an above-threshold ECAP characteristic value, etc.) that caused the trigger signal. In this manner, system 100 may be configured to, or enable a user to, sort trigger signals or associated data based on the time that the trigger signal occurred (e.g., trigger signals within a time period of a specified time or within a specified time range). In some examples, system 100 may be configured to store data based on the type of trigger signal that caused the data to be stored (e.g., provide data associated with a user or system specified type of trigger signal).

In some examples, IMD 110 may analyze the ECAP information stored in long-term memory. In other examples, IMD 110 may include communication circuitry configured to transmit the stored ECAP information to an external device, such as programmer 150. IMD 110 may transmit any ECAP information stored in long-term memory during a communication session with the external device or at the request of the external device. The external device, such as programmer 150, may include a display such that the external device is configured to present, via the display, one or more representations of the stored ECAP information. For example, the external device may display graphs of the waveforms from the ECAP information over time, characteristic values over time, markers associated with the trigger signals, or any other such representations of the ECAP information.

Figure 2:
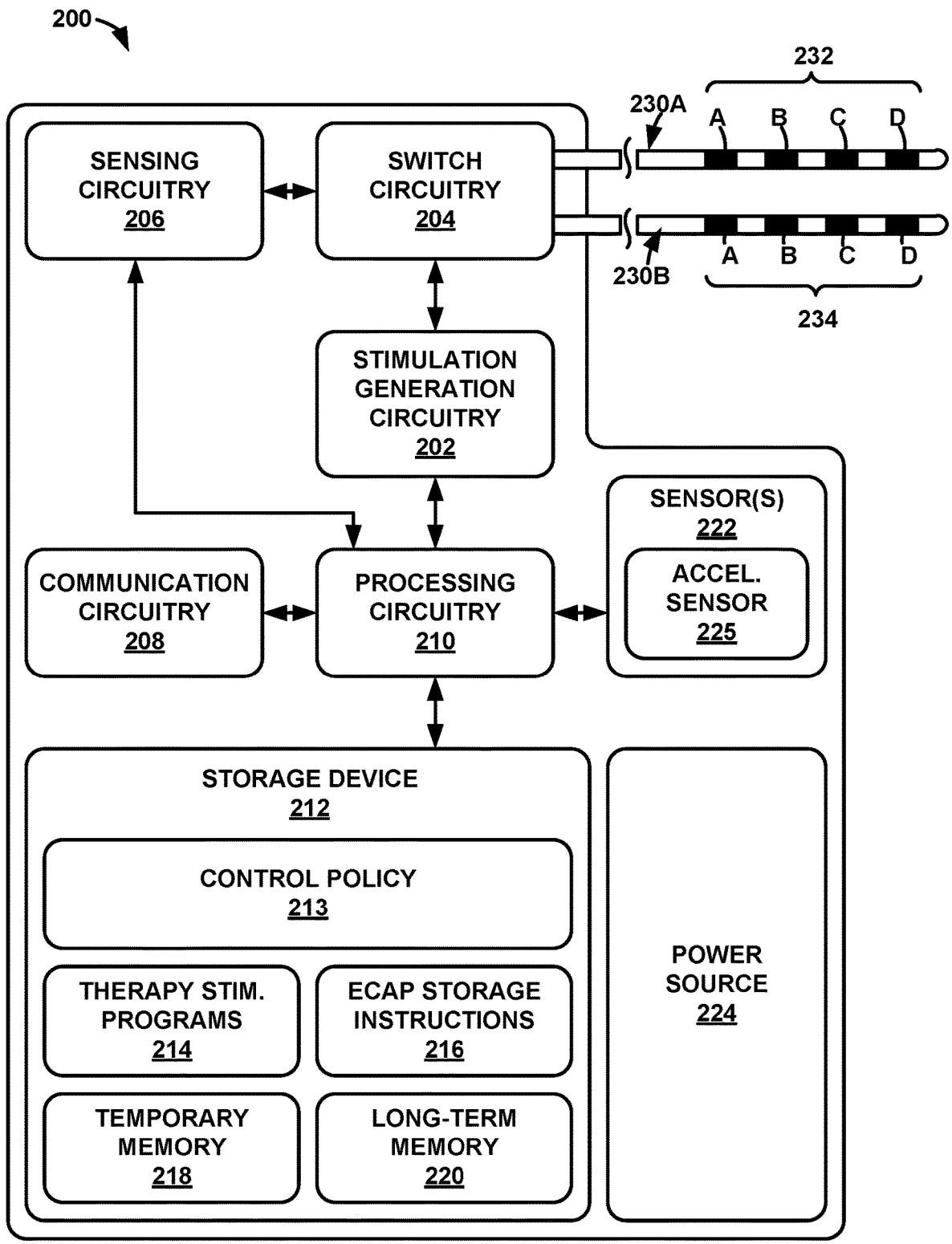
FIG. 2 is a block diagram illustrating an example configuration of components of an IMD, in accordance with one or more techniques of this disclosure.

FIG. 2 is a block diagram illustrating an example configuration of components of IMD 200, in accordance with one or more techniques of this disclosure. IMD 200 may be an example of IMD 110 of FIG. 1. In the example shown in FIG. 2, IMD 200 includes stimulation generation circuitry 202, switch circuitry 204, sensing circuitry 206, communication circuitry 208, processing circuitry 210, storage device 212, sensor(s) 222, and power source 224.

In the example shown in FIG. 2, storage device 212 stores therapy stimulation programs 214 and ECAP storage instructions 216 in separate memories within storage device 212 or separate areas within storage device 212. Storage device 212 also includes temporary memory 218 (e.g., a rolling buffer) and long-term memory 220, which may be on the same or physically separate memories. Each stored therapy stimulation program of therapy stimulation programs 214 defines values for a set of electrical stimulation parameters (e.g., a stimulation parameter set), such as a stimulation electrode combination, electrode polarity, current or voltage amplitude, pulse width, pulse rate, and pulse shape. The ECAP storage instructions 216 include instructions regarding receiving and storing ECAP information, such as how long ECAP information is stored, when to store ECAP information in temporary memory 218, when to store ECAP information in long-term memory 220, when to change ECAP sensing rates, or any other aspects related to the sensing and storage of ECAP information. Temporary memory 218 may include a rolling buffer (e.g., first-in-first-out) memory that stores all ECAP information received from sensing circuitry 206. Long-term memory 220 may include the ECAP information that processing circuitry 210 has selected, based on criteria such as when a trigger signal is received, for long-term storage and/or eventual transmission to another device (e.g., programmer 150).

Accordingly, in some examples, stimulation generation circuitry 202 generates electrical stimulation signals in accordance with the electrical stimulation parameters noted above. Other ranges of stimulation parameter values may also be useful and may depend on the target stimulation site within patient 105. While stimulation pulses are described, stimulation signals may be of any form, such as continuous-time signals (e.g., sine waves) or the like. Switch circuitry 204 may include one or more switch arrays, one or more multiplexers, one or more switches (e.g., a switch matrix or other collection of switches), or other electrical circuitry configured to direct stimulation signals from stimulation generation circuitry 202 to one or more of electrodes 232, 234, or directed sensed signals from one or more of electrodes 232, 234 to sensing circuitry 206. In other examples, stimulation generation circuitry 202 and/or sensing circuitry 206 may include sensing circuitry to direct signals to and/or from one or more of electrodes 232, 234, which may or may not also include switch circuitry 204.

Sensing circuitry 206 monitors signals from any combination of electrodes 232, 234. In some examples, sensing circuitry 206 includes one or more amplifiers, filters, and analog-to-digital converters. Sensing circuitry 206 may be used to sense physiological signals, such as ECAPs. In some examples, sensing circuitry 206 detects ECAPs from a particular combination of electrodes 232, 234. In some cases, the particular combination of electrodes for sensing ECAPs includes different electrodes than a set of electrodes 232, 234 used to deliver stimulation pulses. Alternatively, in other cases, the particular combination of electrodes used for sensing ECAPs includes at least one of the same electrodes as a set of electrodes used to deliver stimulation pulses to patient 105. Sensing circuitry 206 may provide signals to an analog-to-digital converter, for conversion into a digital signal for processing, analysis, storage, or output by processing circuitry 210.

Communication circuitry 208 supports wireless communication between IMD 200 and an external programmer (not shown in FIG. 2) or another computing device under the control of processing circuitry 210. Processing circuitry 210 of IMD 200 may receive, as updates to programs, values for various stimulation parameters such as amplitude and electrode combination, from the external programmer via communication circuitry 208. Updates to the therapy stimulation programs 214 and ECAP test stimulation programs 216 may be stored within storage device 212. Communication circuitry 208 in IMD 200, as well as telemetry circuits in other devices and systems described herein, such as the external programmer, may accomplish communication by radiofrequency (RF) communication techniques. In addition, communication circuitry 208 may communicate with an external medical device programmer (not shown in FIG. 2) via proximal inductive interaction of IMD 200 with the external programmer. The external programmer may be one example of external programmer 150 of FIG. 1. Accordingly, communication circuitry 208 may send information to the external programmer on a continuous basis, at periodic intervals, or upon request from IMD 110 or the external programmer.

Processing circuitry 210 may include any one or more of a microprocessor, a controller, a digital signal processor (DSP), an application specific integrated circuit (ASIC), a field-programmable gate array (FPGA), discrete logic circuitry, or any other processing circuitry configured to provide the functions attributed to processing circuitry 210 herein may be embodied as firmware, hardware, software or any combination thereof. Processing circuitry 210 controls stimulation generation circuitry 202 to generate stimulation signals according to therapy stimulation programs 214 and ECAP test stimulation programs 216 stored in storage device 212 to apply stimulation parameter values specified by one or more of programs, such as amplitude, pulse width, pulse rate, and pulse shape of each of the stimulation signals.

In the example shown in FIG. 2, the set of electrodes 232 includes electrodes 232A, 232B, 232C, and 232D, and the set of electrodes 234 includes electrodes 234A, 234B, 234C, and 234D. In other examples, a single lead may include all eight electrodes 232 and 234 along a single axial length of the lead. Processing circuitry 210 also controls stimulation generation circuitry 202 to generate and apply the stimulation signals to selected combinations of electrodes 232, 234. In some examples, stimulation generation circuitry 202 includes a switch circuit (instead of, or in addition to, switch circuitry 204) that may couple stimulation signals to selected conductors within leads 230, which, in turn, deliver the stimulation signals across selected electrodes 232, 234. Such a switch circuit may be a switch array, switch matrix, multiplexer, or any other type of switching circuit configured to selectively couple stimulation energy to selected electrodes 232, 234 and to selectively sense bioelectrical neural signals of a spinal cord of the patient (not shown in FIG. 2) with selected electrodes 232, 234.

In other examples, however, stimulation generation circuitry 202 does not include a switch circuit and switch circuitry 204 does not interface between stimulation generation circuitry 202 and electrodes 232, 234. In these examples, stimulation generation circuitry 202 includes a plurality of pairs of voltage sources, current sources, voltage sinks, or current sinks connected to each of electrodes 232, 234 such that each pair of electrodes has a unique signal circuit. In other words, in these examples, each of electrodes 232, 234 is independently controlled via its own signal circuit (e.g., via a combination of a regulated voltage source and sink or regulated current source and sink), as opposed to switching signals between electrodes 232, 234.

Electrodes 232, 234 on respective leads 230 may be constructed of a variety of different designs. For example, one or both of leads 230 may include one or more electrodes at each longitudinal location along the length of the lead, such as one electrode at different perimeter locations around the perimeter of the lead at each of the locations A, B, C, and D. In one example, the electrodes may be electrically coupled to stimulation generation circuitry 202, e.g., via switch circuitry 204 and/or switching circuitry of the stimulation generation circuitry 202, via respective wires that are straight or coiled within the housing of the lead and run to a connector at the proximal end of the lead. In another example, each of the electrodes of the lead may be electrodes deposited on a thin film. The thin film may include an electrically conductive trace for each electrode that runs the length of the thin film to a proximal end connector. The thin film may then be wrapped (e.g., a helical wrap) around an internal member to form the lead 230. These and other constructions may be used to create a lead with a complex electrode geometry.

Although sensing circuitry 206 is incorporated into a common housing with stimulation generation circuitry 202 and processing circuitry 210 in FIG. 2, in other examples, sensing circuitry 206 may be in a separate housing from IMD 200 and may communicate with processing circuitry 210 via wired or wireless communication techniques.

In some examples, one or more of electrodes 232 and 234 are suitable for sensing the ECAPs. For instance, electrodes 232 and 234 may sense the voltage amplitude of a portion of the ECAP signals, where the sensed voltage amplitude is a characteristic the ECAP signal.

Storage device 212 may be configured to store information within IMD 200 during operation. Storage device 212 may include a computer-readable storage medium or computer-readable storage device. In some examples, storage device 212 includes one or more of a short-term memory (e.g., temporary memory 218) or a long-term memory (e.g., long-term memory 220). Storage device 212 may include, for example, random access memories (RAM), dynamic random access memories (DRAM), static random access memories (SRAM), ferroelectric random access memories (FRAM), magnetic discs, optical discs, flash memories, or forms of electrically programmable memories (EPROM) or electrically erasable and programmable memories (EEPROM). In some examples, storage device 212 is used to store data indicative of instructions for execution by processing circuitry 210. As discussed above, storage device 212 is configured to store therapy stimulation programs 214 and ECAP storage instructions 216.

In some examples, stimulation generation circuitry 202 may be configured to deliver electrical stimulation therapy to patient 105. The electrical stimulation therapy may, in some cases, include a plurality of informed pulses. Additionally, stimulation generation circuitry 202 may be configured to deliver a plurality of control pulses, where the plurality of control pulses is interleaved with at least some informed pulses of the plurality of informed pulses. Stimulation generation circuitry may deliver the plurality of informed pulses and the plurality of control pulses to target tissue (e.g., spinal cord 120) of patient 105 via electrodes 232, 234 of leads 230. By delivering such informed pulses and control pulses, stimulation generation circuitry 202 may evoke responsive ECAPs in the target tissue, the responsive ECAPs propagating through the target tissue before arriving back at electrodes 232, 234. In some examples, a different combination of electrodes 232, 234 may sense responsive ECAPs than a combination of electrodes 232, 234 that delivers informed pulses and a combination of electrodes 232, 234 that delivers control pulses. Sensing circuitry 206 may be configured to detect the responsive ECAPs via electrodes 232, 234 and leads 230. In other examples, stimulation generation circuitry 202 may be configured to deliver a plurality of control pulses, without any informed pulses, when control pulses also provide therapeutic effect for the patient.

Processing circuitry 210 may, in some cases, direct sensing circuitry 206 to continuously monitor for ECAPs. In other cases, processing circuitry 210 may direct sensing circuitry 206 to may monitor for ECAPs based on signals from sensor(s) 222. For example, processing circuitry 210 may activate sensing circuitry 206 based on an activity level of patient 105 exceeding an activity level threshold (e.g., an accelerometer signal of acceleration sensor 225 rises above a threshold). Activating and deactivating sensing circuitry 206 may, in some examples, extend a battery life of power source 224. In other examples, processing circuitry 210 may determine and store acceleration data derived from acceleration sensor 225 that represents posture states and/or activity of the patient. Processing circuitry 210 may correlate the acceleration data with the ECAP information for temporary storage or long-term storage in response to receiving the trigger signal herein. In this manner, the acceleration data may represent posture states and/or activity of the patient that corresponds to the same time at which the ECAP information was collected for the patient. The acceleration data and the ECAP information may thus be temporally aligned to represent aspects of the patient at the same time. In addition, processing circuitry 210 may store a time stamp or other indicating data along with the ECAP information and/or the acceleration data in order to temporally align the ECAP information and acceleration data and/or other events in time. The combination of ECAP information and acceleration data may help a clinician or patient to identify movements that result in uncomfortable stimulation or ineffective therapy.

In some examples, processing circuitry 210 determines if a characteristic of a first ECAP is greater than a threshold ECAP characteristic value. The threshold ECAP characteristic value may be stored in storage device 212. In some examples, the characteristic of the first ECAP is a voltage amplitude of the first ECAP. In some such examples, the threshold ECAP characteristic value is selected from a range of approximately 10 microvolts (μV) to approximately 20 μV. In other examples, processing circuitry 210 determines if another characteristic (e.g., ECAP current amplitude, ECAP slew rate, area underneath the ECAP, ECAP slope, or ECAP duration) of the first ECAP is greater than the threshold ECAP characteristic value.

If processing circuitry 210 determines that the characteristic of the first ECAP is greater than the threshold ECAP characteristic value, processing circuitry 210 is configured to activate a decrement mode, altering at least one parameter of each therapy pulse of a set of informed pulses delivered by IMD 200 after the first ECAP is sensed by sensing circuitry 206. Additionally, while the decrement mode is activated, processing circuitry 210 may change at least one parameter of each control pulse of a set of control pulses delivered by IMD 200 after the first ECAP is sensed by sensing circuitry 206. In some examples, the at least one parameter of the informed pulses and the at least one parameter of the control pulses adjusted by processing circuitry 210 during the decrement mode includes a stimulation current amplitude. In some such examples, during the decrement mode, processing circuitry 210 decreases an electrical current amplitude of each consecutive stimulation pulse (e.g., each therapy pulse and each control pulse) delivered by IMD 200. In other examples, the at least one parameter of the stimulation pulses adjusted by processing circuitry 210 during the decrement mode include any combination of electrical current amplitude, electrical voltage amplitude, slew rate, pulse shape, pulse frequency, or pulse duration.

In the example illustrated by FIG. 2, the decrement mode is stored in storage device 212 as a part of control policy 213. The decrement mode may include a list of instructions which enable processing circuitry 210 to adjust parameters of stimulation pulses according to a function. In some examples, when the decrement mode is activated, processing circuitry 210 decreases a parameter (e.g., an electrical current) of each consecutive therapy pulse and each consecutive control pulse according to a linear function. In other examples, when the decrement mode is activated, processing circuitry 210 decreases a parameter (e.g., an electrical current) of each consecutive therapy pulse and each consecutive control pulse according to an exponential function, a logarithmic function, or a piecewise function. While the decrement mode is activated, sensing circuitry 206 may continue to monitor responsive ECAPs. In turn, sensing circuitry 206 may detect ECAPs responsive to control pulses delivered by IMD 200.

Throughout the decrement mode, processing circuitry may monitor ECAPs responsive to stimulation pulses. Processing circuitry 210 may determine if a characteristic of a second ECAP is less than the threshold ECAP characteristic value. The second ECAP may, in some cases, be the leading ECAP occurring after the first ECAP which is less than the threshold ECAP characteristic value. In other words, each ECAP recorded by sensing circuitry 206 between the first ECAP and the second ECAP is greater than or equal to the threshold ECAP characteristic value. Based on the characteristic of the second ECAP being less than the threshold ECAP characteristic value, processing circuitry 210 may deactivate the decrement mode and activate an increment mode, thus altering at least one parameter of each therapy pulse of a set of informed pulses delivered by IMD 200 after the second ECAP is sensed by sensing circuitry 206. Additionally, while the increment mode is activated, processing circuitry 210 may change at least one parameter of each control pulse of a set of control pulses delivered by IMD 200 after the second ECAP is sensed by sensing circuitry 206.

In some examples, the at least one parameter of the informed pulses and the at least one parameter of the control pulses adjusted by processing circuitry 210 during the increment mode includes a stimulation current amplitude. In some such examples, during the increment mode, processing circuitry 210 increases an electrical current amplitude of each consecutive stimulation pulse (e.g., each therapy pulse and each control pulse) delivered by IMD 200. In other examples, the at least one parameter of the stimulation pulses adjusted by processing circuitry 210 during the increment mode include any combination of electrical current amplitude, electrical voltage amplitude, slew rate, pulse shape, pulse frequency, or pulse duration.

In the example illustrated by FIG. 2, the increment mode is stored in storage device 212 as a part of control policy 213. The increment mode may include a list of instructions which enable processing circuitry 210 to adjust parameters of stimulation pulses according to a function. In some examples, when the increment mode is activated, processing circuitry 210 increases a parameter (e.g., an electrical current) of each consecutive therapy pulse and each consecutive control pulse according to a linear function. In other examples, when the increment mode is activated, processing circuitry 210 increases a parameter (e.g., an electrical current) of each consecutive therapy pulse and each consecutive control pulse according to a non-linear function, such as an exponential function, a logarithmic function, or a piecewise function. While the increment mode is activated, sensing circuitry 206 may continue to monitor responsive ECAPs. In turn, sensing circuitry 206 may detect ECAPs responsive to control pulses delivered by IMD 200.

Processing circuitry 210 may complete the increment mode such that the one or more parameters of the stimulation pulses return to baseline parameter values of stimulation pulses delivered before processing circuitry 210 activates the decrement mode (e.g., before sensing circuitry 206 detects the first ECAP). By first decrementing and subsequently incrementing stimulation pulses in response to ECAPs exceeding a threshold ECAP characteristic value, processing circuitry 210 may prevent patient 105 from experiencing transient overstimulation or decrease a severity of transient overstimulation experienced by patient 105.

Although, in some examples, sensing circuitry 206 senses ECAPs which occur in response to control pulses delivered according to ECAP test stimulation programs 216, in other examples, sensing circuitry 206 senses ECAPs which occur in response to informed pulses delivered according to therapy stimulation programs 214. The techniques of this disclosure may enable IMD 200 to toggle the decrement mode and the increment mode using any combination of ECAPs corresponding to informed pulses and ECAPs corresponding to control pulses.

Sensor(s) 222 may include one or more sensing elements that sense values of a respective patient parameter. As described, electrodes 232 and 234 may be the electrodes that sense the characteristic value of the ECAP. Sensor(s) 222 may include one or more accelerometers (such as acceleration sensor 225), optical sensors, chemical sensors, temperature sensors, pressure sensors, or any other types of sensors. Sensor(s) 222 may output patient parameter values that may be used as feedback to control delivery of therapy. For example, sensor(s) 222 may indicate patient activity, and processing circuitry 210 may increase the frequency of control pulses and ECAP sensing in response to detecting increased patient activity. In one example, processing circuitry 210 may initiate control pulses and corresponding ECAP sensing in response to a signal from sensor(s) 222 indicating that patient activity has exceeded an activity threshold. Conversely, processing circuitry 210 may decrease the frequency of control pulses and ECAP sensing in response to detecting decreased patient activity. For example, in response to sensor(s) 222 no longer indicating that the sensed patient activity exceeds a threshold, processing circuitry 210 may suspend or stop delivery of control pulses and ECAP sensing. In this manner, processing circuitry 210 may dynamically deliver control pulses and sense ECAP signals based on patient activity to reduce power consumption of the system when the electrode-to-neuron distance is not likely to change and increase system response to ECAP changes when electrode-to-neuron distance is likely to change. IMD 200 may include additional sensors within the housing of IMD 200 and/or coupled via one of leads 130 or other leads. In addition, IMD 200 may receive sensor signals wirelessly from remote sensors via communication circuitry 208, for example. In some examples, one or more of these remote sensors may be external to patient (e.g., carried on the external surface of the skin, attached to clothing, or otherwise positioned external to patient 105). In some examples, signals from sensor(s) 222 indicate a position or body state (e.g., sleeping, awake, sitting, standing, or the like), and processing circuitry 210 may select target ECAP characteristic values according to the indicated position or body state.

Power source 224 is configured to deliver operating power to the components of IMD 200. Power source 224 may include a battery and a power generation circuit to produce the operating power. In some examples, the battery is rechargeable to allow extended operation. In some examples, recharging is accomplished through proximal inductive interaction between an external charger and an inductive charging coil within IMD 200. Power source 224 may include any one or more of a plurality of different battery types, such as nickel cadmium batteries and lithium ion batteries.

Figure 3:
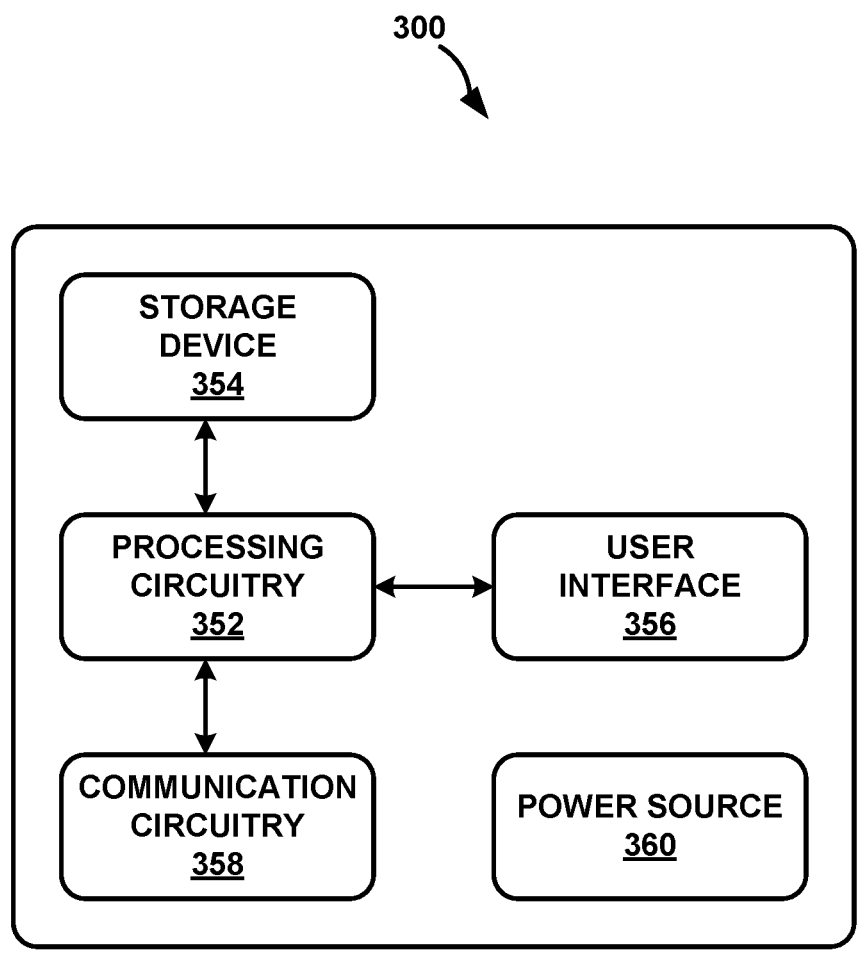
FIG. 3 is a block diagram illustrating an example configuration of components of an external programmer, in accordance with one or more techniques of this disclosure.

FIG. 3 is a block diagram illustrating an example configuration of components of external programmer 300, in accordance with one or more techniques of this disclosure. External programmer 300 may be an example of external programmer 150 of FIG. 1. Although external programmer 300 may generally be described as a hand-held device, external programmer 300 may be a larger portable device or a more stationary device. In addition, in other examples, external programmer 300 may be included as part of an external charging device or include the functionality of an external charging device. As illustrated in FIG. 3, external programmer 300 may include processing circuitry 352, storage device 354, user interface 356, communication circuitry 358, and power source 360. Storage device 354 may store instructions that, when executed by processing circuitry 352, cause processing circuitry 352 and external programmer 300 to provide the functionality ascribed to external programmer 300 throughout this disclosure. Each of these components, circuitry, or modules, may include electrical circuitry that is configured to perform some, or all of the functionality described herein. For example, processing circuitry 352 may include processing circuitry configured to perform the processes discussed with respect to processing circuitry 352.

In general, external programmer 300 includes any suitable arrangement of hardware, alone or in combination with software and/or firmware, to perform the techniques attributed to external programmer 300, and processing circuitry 352, user interface 356, and communication circuitry 358 of external programmer 300. In various examples, external programmer 300 may include one or more processors, such as one or more microprocessors, DSPs, ASICs, FPGAs, or any other equivalent integrated or discrete logic circuitry, as well as any combinations of such components. External programmer 300 also, in various examples, may include a storage device 354, such as RAM, ROM, PROM, EPROM, EEPROM, flash memory, a hard disk, a CD-ROM, including executable instructions for causing the one or more processors to perform the actions attributed to them. Moreover, although processing circuitry 352 and communication circuitry 358 are described as separate modules, in some examples, processing circuitry 352 and communication circuitry 358 are functionally integrated. In some examples, processing circuitry 352 and communication circuitry 358 correspond to individual hardware units, such as ASICs, DSPs, FPGAs, or other hardware units.

Storage device 354 (e.g., a storage device) may store instructions that, when executed by processing circuitry 352, cause processing circuitry 352 and external programmer 300 to provide the functionality ascribed to external programmer 300 throughout this disclosure. For example, storage device 354 may include instructions that cause processing circuitry 352 to obtain a parameter set from memory, select a spatial electrode movement pattern, or receive a user input and send a corresponding command to IMD 200, or instructions for any other functionality. In addition, storage device 354 may include a plurality of programs, where each program includes a parameter set that defines stimulation pulses, such as control pulses and/or informed pulses. Storage device 354 may also store data received from a medical device (e.g., IMD 110). For example, storage device 354 may store ECAP related data recorded at a sensing module of the medical device, and storage device 354 may also store data from one or more sensors of the medical device. This ECAP related data may include ECAP information transmitted from an implantable medical device, such as IMD 110.

User interface 356 may include a button or keypad, lights, a speaker for voice commands, a display, such as a liquid crystal (LCD), light-emitting diode (LED), or organic light-emitting diode (OLED). In some examples the display includes a touch screen. User interface 356 may be configured to display any information related to the delivery of electrical stimulation, identified patient behaviors, sensed patient parameter values, patient behavior criteria, or any other such information. In addition, as described herein, processing circuitry 352 may control user interface 356 to present graphical representations of ECAP information transmitted by IMD 110. User interface 356 may also receive user input via user interface 356. The input may be, for example, in the form of pressing a button on a keypad or selecting an icon from a touch screen. The input may request starting or stopping electrical stimulation, the input may request a new spatial electrode movement pattern or a change to an existing spatial electrode movement pattern, of the input may request some other change to the delivery of electrical stimulation.

Communication circuitry 358 may support wireless communication between the medical device and external programmer 300 under the control of processing circuitry 352. Communication circuitry 358 may also be configured to communicate with another computing device via wireless communication techniques, or direct communication through a wired connection. In some examples, communication circuitry 358 provides wireless communication via an RF or proximal inductive medium. In some examples, communication circuitry 358 includes an antenna, which may take on a variety of forms, such as an internal or external antenna.

Examples of local wireless communication techniques that may be employed to facilitate communication between external programmer 300 and IMD 110 include RF communication according to the 802.11 or Bluetooth® specification sets or other standard or proprietary telemetry protocols. In this manner, other external devices may be capable of communicating with external programmer 300 without needing to establish a secure wireless connection. As described herein, communication circuitry 358 may be configured to transmit a spatial electrode movement pattern or other stimulation parameter values to IMD 110 for delivery of electrical stimulation therapy.

In some examples, selection of stimulation parameters or therapy stimulation programs are transmitted to the medical device for delivery to a patient (e.g., patient 105 of FIG. 1). In other examples, the therapy may include medication, activities, or other instructions that patient 105 must perform themselves or a caregiver perform for patient 105. In some examples, external programmer 300 provides visual, audible, and/or tactile notifications that indicate there are new instructions. External programmer 300 requires receiving user input acknowledging that the instructions have been completed in some examples.

According to the techniques of the disclosure, user interface 356 of external programmer 300 may also receive user input associated with a trigger signal to be transmitted to IMD 110 for storing ECAP information in long-term memory. For example the user input may explicitly request ECAP information that is being recorded at that time. In other examples, the user input may indicate that an event has occurred, such as a patient movement (e.g., sneeze, cough, laugh, posture change, etc.) that caused an undesired stimulation sensation or loss of therapy or any other situation related to stimulation therapy (e.g., any sensation or loss of therapy that may be of interest to the patient or a clinician). In this manner, the patient may provide the user input any time the patient feels a sensation that is undesirable, "funny," or in any way may be of interest to the patient. Processing circuitry 352 may cause communication circuitry 358 to transmit the trigger signal to IMD 110. Processing circuitry 352 may then receive, via communication circuitry 358, stored ECAP information from IMD 110.

Power source 360 is configured to deliver operating power to the components of external programmer 300. Power source 360 may include a battery and a power generation circuit to produce the operating power. In some examples, the battery is rechargeable to allow extended operation. Recharging may be accomplished by electrically coupling power source 360 to a cradle or plug that is connected to an alternating current (AC) outlet. In addition, recharging may be accomplished through proximal inductive interaction between an external charger and an inductive charging coil within external programmer 300. In other examples, traditional batteries (e.g., nickel cadmium or lithium ion batteries) may be used. In addition, external programmer 300 may be directly coupled to an alternating current outlet to operate.

The architecture of external programmer 300 illustrated in FIG. 3 is shown as an example. The techniques as set forth in this disclosure may be implemented in the example external programmer 300 of FIG. 3, as well as other types of systems not described specifically herein. Nothing in this disclosure should be construed so as to limit the techniques of this disclosure to the example architecture illustrated by FIG. 3.

Figure 4:
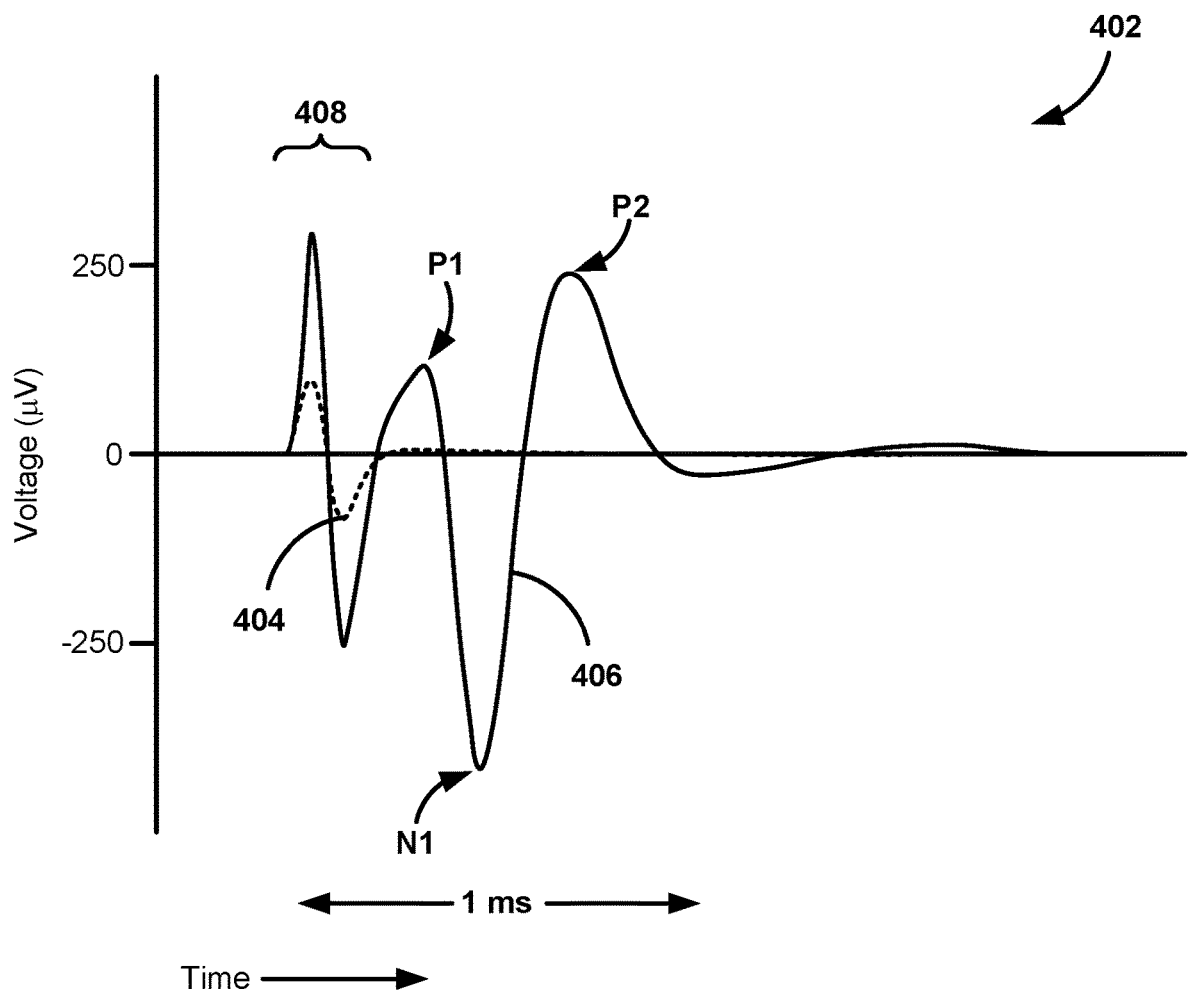
FIG. 4 is a graph of example evoked compound action potentials (ECAPs) sensed for respective stimulation pulses, in accordance with one or more techniques of this disclosure.

FIG. 4 is a graph 402 of example evoked compound action potentials (ECAPs) sensed for respective stimulation pulses, in accordance with one or more techniques of this disclosure. As shown in FIG. 4, graph 402 shows example ECAP signal 404 (dotted line) and ECAP signal 406 (solid line). In some examples, each of ECAP signals 404 and 406 are sensed from control pulses that were delivered from a guarded cathode, where the control pulses are bi-phasic pulses including an interphase interval between each positive and negative phase of the pulse. In some such examples, the guarded cathode includes stimulation electrodes located at the end of an 8-electrode lead (e.g., leads 130 of FIG. 1) while two sensing electrodes are provided at the other end of the 8-electrode lead. ECAP signal 404 illustrates the voltage amplitude sensed as a result from a sub-detection threshold stimulation pulse, or a stimulation pulse which results in no detectable ECAP. Peaks 408 of ECAP signal 404 are detected and represent the artifact of the delivered control pulse. However, no propagating signal is detected after the artifact in ECAP signal 404 because the control pulse was sub-detection stimulation threshold.

In contrast to ECAP signal 404, ECAP signal 406 (e.g., a waveform) represents the voltage amplitude detected from a supra-detection stimulation threshold control pulse. Peaks 408 of ECAP signal 406 are detected and represent the artifact of the delivered control pulse. After peaks 408, ECAP signal 406 also includes peaks P1, N1, and P2, which are three typical peaks representative of propagating action potentials from an ECAP. The example duration of the artifact and peaks P1, N1, and P2 is approximately 1 millisecond (ms). When detecting the ECAP of ECAP signal 406, different characteristics may be identified. For example, the characteristic of the ECAP may be the amplitude between N1 and P2. This N1-P2 amplitude may be easily detectable even if the artifact impinges on P1, a relatively large signal, and the N1-P2 amplitude may be minimally affected by electronic drift in the signal. In other examples, the characteristic of the ECAP used to control subsequent control pulses and/or informed pulses may be an amplitude of P1, N1, or P2 with respect to neutral or zero voltage. In some examples, the characteristic of the ECAP used to control subsequent control pulses or informed pulses is a sum of two or more of peaks P1, N1, or P2. In other examples, the characteristic of ECAP signal 406 may be the area under one or more of peaks P1, N1, and/or P2. In other examples, the characteristic of the ECAP may be a ratio of one of peaks P1, N1, or P2 to another one of the peaks. In some examples, the characteristic of the ECAP is a slope between two points in the ECAP signal, such as the slope between N1 and P2. In other examples, the characteristic of the ECAP may be the time between two points of the ECAP, such as the time between N1 and P2. The time between when the stimulation pulse is delivered and a point in the ECAP signal may be referred to as a latency of the ECAP and may indicate the types of fibers being captured by the stimulation pulse (e.g., a control pulse). ECAP signals with lower latency (i.e., smaller latency values) indicate a higher percentage of nerve fibers that have faster propagation of signals, whereas ECAP signals with higher latency (i.e., larger latency values) indicate a higher percentage of nerve fibers that have slower propagation of signals. Latency may also refer to the time between an electrical feature is detected at one electrode and then detected again at a different electrode. This time, or latency, is inversely proportional to the conduction velocity of the nerve fibers. Other characteristics of the ECAP signal may be used in other examples.

The amplitude of the ECAP signal increases with increased amplitude of the control pulse, as long as the pulse amplitude is greater than threshold such that nerves depolarize and propagate the signal. The target ECAP characteristic (e.g., the target ECAP amplitude) may be determined from the ECAP signal detected from a control pulse when informed pulses are determined to deliver effective therapy to patient 105. The ECAP signal thus is representative of the distance between the stimulation electrodes and the nerves appropriate for the stimulation parameter values of the informed pulses delivered at that time. Therefore, IMD 110 may attempt to use detected changes to the measured ECAP characteristic value to change therapy pulse parameter values and maintain the target ECAP characteristic value during therapy pulse delivery.

Figure 5A:
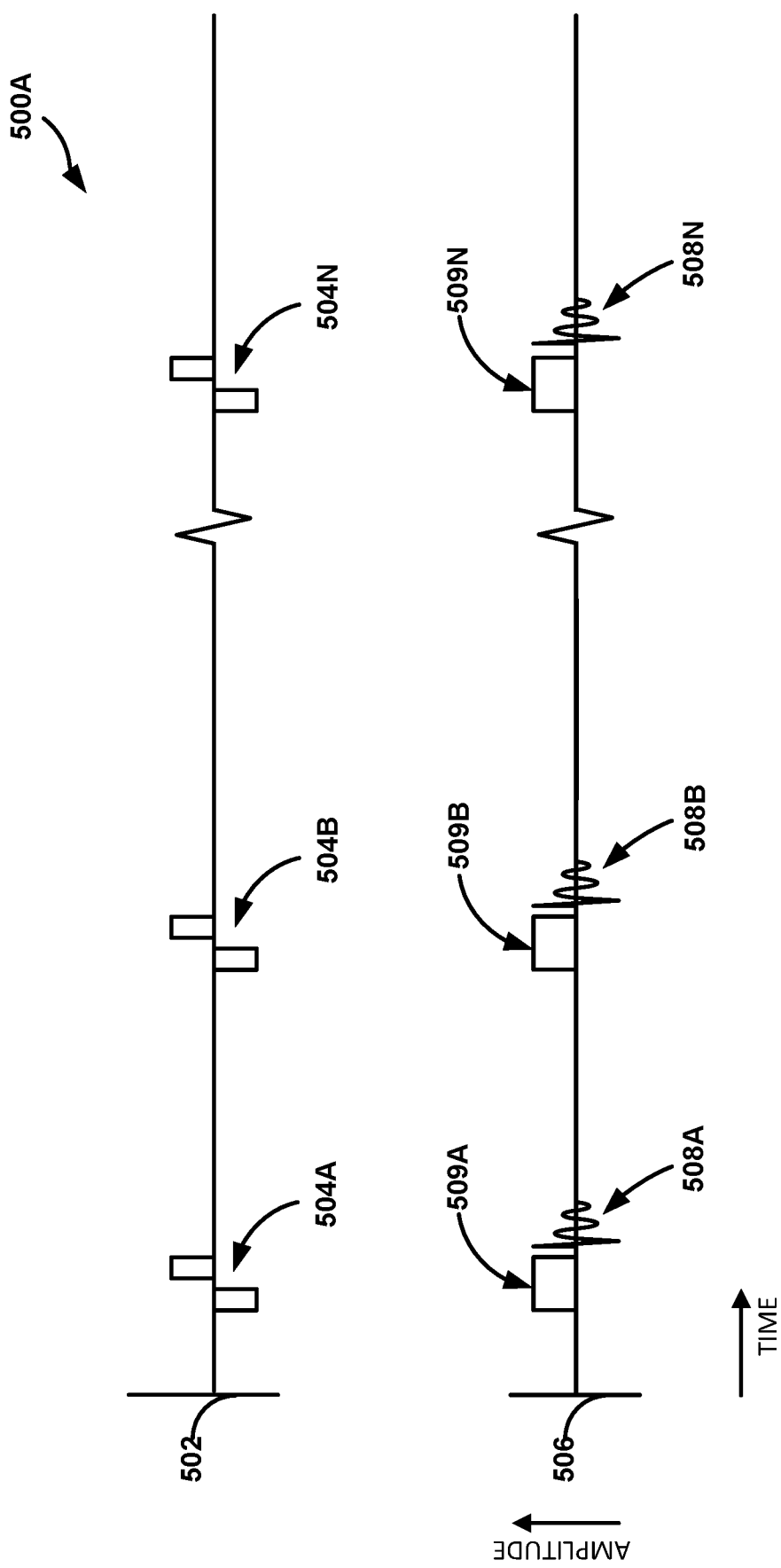
FIG. 5A is a timing diagram illustrating an example of electrical stimulation pulses, respective stimulation signals, and respective sensed ECAPs, in accordance with one or more techniques of this disclosure.

FIG. 5A is a timing diagram 500A illustrating an example of electrical stimulation pulses, respective stimulation signals, and respective sensed ECAPs, in accordance with one or more techniques of this disclosure. For convenience, FIG. 5A is described with reference to IMD 200 of FIG. 2. As illustrated, timing diagram 500A includes first channel 502, a plurality of stimulation pulses 504A-504N (collectively "stimulation pulses 504"), second channel 506, a plurality of respective ECAPs 508A-508N (collectively "ECAPs 508"), and a plurality of stimulation signals 509A-509N (collectively "stimulation signals 509"). In some examples, stimulation pulses 504 may represent control pulses which are configured to elicit ECAPs 508 that are detectible by IMD 200, but this is not required. Stimulation pulses 504 may represent any type of pulse that is deliverable by IMD 200. In the example of FIG. 5A, IMD 200 can deliver therapy with control pulses instead of, or without, informed pulses.

First channel 502 is a time/voltage (and/or current) graph indicating the voltage (or current) of at least one electrode of electrodes 232, 234. In one example, the stimulation electrodes of first channel 502 may be located on the opposite side of the lead as the sensing electrodes of second channel 506. Stimulation pulses 504 may be electrical pulses delivered to the spinal cord of the patient by at least one of electrodes 232, 234, and stimulation pulses 504 may be balanced biphasic square pulses with an interphase interval. In other words, each of stimulation pulses 504 are shown with a negative phase and a positive phase separated by an interphase interval. For example, a stimulation pulse 504 may have a negative voltage for the same amount of time and amplitude that it has a positive voltage. It is noted that the negative voltage phase may be before or after the positive voltage phase. Stimulation pulses 504 may be delivered according to test stimulation programs 216 stored in storage device 212 of IMD 200, and ECAP test stimulation programs may be updated according to user input via an external programmer and/or may be updated according to a signal from sensor(s) 222. In one example, stimulation pulses 504 may have a pulse width of less than approximately 300 microseconds (e.g., the total time of the positive phase, the negative phase, and the interphase interval is less than 300 microseconds). In another example, stimulation pulses 504 may have a pulse width of approximately 100 µs for each phase of the bi-phasic pulse. As illustrated in FIG. 5A, stimulation pulses 504 may be delivered via channel 502. Delivery of stimulation pulses 504 may be delivered by leads 230 in a guarded cathode electrode combination. For example, if leads 230 are linear 8-electrode leads, a guarded cathode combination is a central cathodic electrode with anodic electrodes immediately adjacent to the cathodic electrode.

Second channel 506 is a time/voltage (and/or current) graph indicating the voltage (or current) of at least one electrode of electrodes 232, 234. In one example, the electrodes of second channel 506 may be located on the opposite side of the lead as the electrodes of first channel 502. ECAPs 508 may be sensed at electrodes 232, 234 from the spinal cord of the patient in response to stimulation pulses 504. ECAPs 508 are electrical signals which may propagate along a nerve away from the origination of stimulation pulses 504. In one example, ECAPs 508 are sensed by different electrodes than the electrodes used to deliver stimulation pulses 504. As illustrated in FIG. 5A, ECAPs 508 may be recorded on second channel 506.

Stimulation signals 509A, 509B, and 509N may be sensed by leads 230 and sensing circuitry 206 and may be sensed during the same period of time as the delivery of stimulation pulses 504. Since the stimulation signals may have a greater amplitude and intensity than ECAPs 508, any ECAPs arriving at IMD 200 during the occurrence of stimulation signals 509 might not be adequately sensed by sensing circuitry 206 of IMD 200. However, ECAPs 508 may be sufficiently sensed by sensing circuitry 206 because each ECAP 508, or at least a portion of ECAP 508 used as feedback for stimulation pulses 504, falls after the completion of each a stimulation pulse 504. As illustrated in FIG. 5A, stimulation signals 509 and ECAPs 508 may be recorded on channel 506. In some examples, ECAPs 508 may not follow respective stimulation signals 509 when ECAPs are not elicited by stimulation pulses 504 or the amplitude of ECAPs is too low to be detected (e.g., below the detection threshold).

Figure 5B:
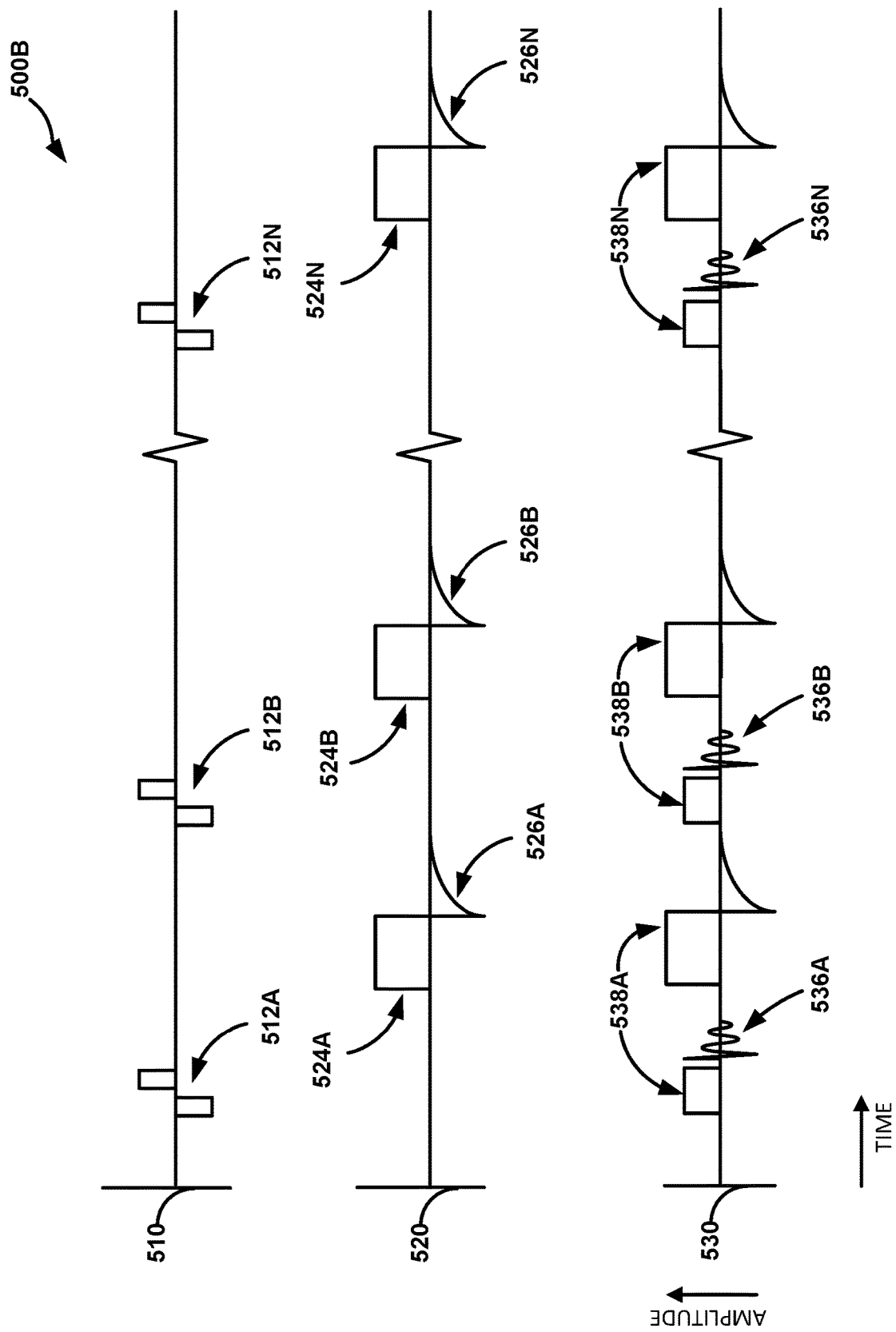
FIG. 5B is a timing diagram illustrating one example of electrical stimulation pulses, respective stimulation signals, and respective sensed ECAPs, in accordance with one or more techniques of this disclosure.

FIG. 5B is a timing diagram 500B illustrating one example of electrical stimulation pulses, respective stimulation signals, and respective sensed ECAPs, in accordance with one or more techniques of this disclosure. For convenience, FIG. 5B is described with reference to IMD 200 of FIG. 2. As illustrated, timing diagram 500B includes first channel 510, a plurality of control pulses 512A-512N (collectively "control pulses 512"), second channel 520, a plurality of informed pulses 524A-524N (collectively "informed pulses 524") including passive recharge phases 526A-526N (collectively "passive recharge phases 526"), third channel 530, a plurality of respective ECAPs 536A-536N (collectively "ECAPs 536"), and a plurality of stimulation signals 538A-538N (collectively "stimulation signals 538").

First channel 510 is a time/voltage (and/or current) graph indicating the voltage (or current) of at least one electrode of electrodes 232, 234. In one example, the stimulation electrodes of first channel 510 may be located on the opposite side of the lead as the sensing electrodes of third channel 530. Control pulses 512 may be electrical pulses delivered to the spinal cord of the patient by at least one of electrodes 232, 234, and control pulses 512 may be balanced biphasic square pulses with an interphase interval. In other words, each of control pulses 512 are shown with a negative phase and a positive phase separated by an interphase interval. For example, a control pulse 512 may have a negative voltage for the same amount of time that it has a positive voltage. It is noted that the negative voltage phase may be before or after the positive voltage phase. Control pulses 512 may be delivered according to ECAP test stimulation programs stored in storage device 212 of IMD 200, and ECAP test stimulation programs may be updated according to user input via an external programmer and/or may be updated according to a signal from sensor(s) 222. In one example, control pulses 512 may have a pulse width of 300 microseconds (e.g., the total time of the positive phase, the negative phase, and the interphase interval is 300 microseconds). In another example, control pulses 512 may have a pulse width of approximately 100 µs for each phase of the bi-phasic pulse. As illustrated in FIG. 5B, control pulses 512 may be delivered via first channel 510. Delivery of control pulses 512 may be delivered by leads 230 in a guarded cathode electrode combination. For example, if leads 230 are linear 8-electrode leads, a guarded cathode combination is a central cathodic electrode with anodic electrodes immediately adjacent to the cathodic electrode.

Second channel 520 is a time/voltage (and/or current) graph indicating the voltage (or current) of at least one electrode of electrodes 232, 234 for the informed pulses. In one example, the electrodes of second channel 520 may partially or fully share common electrodes with the electrodes of first channel 510 and third channel 530. Informed pulses 524 may also be delivered by the same leads 230 that are configured to deliver control pulses 512. Informed pulses 524 may be interleaved with control pulses 512, such that the two types of pulses are not delivered during overlapping periods of time. However, informed pulses 524 may or may not be delivered by exactly the same electrodes that deliver control pulses 512. Informed pulses 524 may be monophasic pulses with pulse widths of greater than approximately 300 µs and less than approximately 1000 µs. In fact, informed pulses 524 may be configured to have longer pulse widths than control pulses 512. As illustrated in FIG. 5B, informed pulses 524 may be delivered on second channel 520.

Informed pulses 524 may be configured for passive recharge. For example, each informed pulse 524 may be followed by a passive recharge phase 526 to equalize charge on the stimulation electrodes. Unlike a pulse configured for active recharge, where remaining charge on the tissue following a stimulation pulse is instantly removed from the tissue by an opposite applied charge, passive recharge allows tissue to naturally discharge to some reference voltage (e.g., ground or a rail voltage) following the termination of the therapy pulse. In some examples, the electrodes of the medical device may be grounded at the medical device body. In this case, following the termination of informed pulse 524, the charge on the tissue surrounding the electrodes may dissipate to the medical device, creating a rapid decay of the remaining charge at the tissue following the termination of the pulse. This rapid decay is illustrated in passive recharge phases 526. Passive recharge phase 526 may have a duration in addition to the pulse width of the preceding informed pulse 524. In other examples (not pictured in FIG. 5B), informed pulses 524 may be bi-phasic pulses having a positive and negative phase (and, in some examples, an interphase interval between each phase) which may be referred to as pulses including active recharge. An informed pulse that is a bi-phasic pulse may or may not have a following passive recharge phase.

Third channel 530 is a time/voltage (and/or current) graph indicating the voltage (or current) of at least one electrode of electrodes 232, 234. In one example, the electrodes of third channel 530 may be located on the opposite side of the lead as the electrodes of first channel 510. ECAPs 536 may be sensed at electrodes 232, 234 from the spinal cord of the patient in response to control pulses 512. ECAPs 536 are electrical signals which may propagate along a nerve away from the origination of control pulses 512. In one example, ECAPs 536 are sensed by different electrodes than the electrodes used to deliver control pulses 512. As illustrated in FIG. 5B, ECAPs 536 may be recorded on third channel 530.

Stimulation signals 538A, 538B, and 538N may be sensed by leads 230 and may be sensed during the same period of time as the delivery of control pulses 512 and informed pulses 524. Since the stimulation signals may have a greater amplitude and intensity than ECAPs 536, any ECAPs arriving at IMD 200 during the occurrence of stimulation signals 538 may not be adequately sensed by sensing circuitry 206 of IMD 200. However, ECAPs 536 may be sufficiently sensed by sensing circuitry 206 because each ECAP 536 falls after the completion of each a control pulse 512 and before the delivery of the next informed pulse 524. As illustrated in FIG. 5B, stimulation signals 538 and ECAPs 536 may be recorded on channel 530.

Figure 6A:
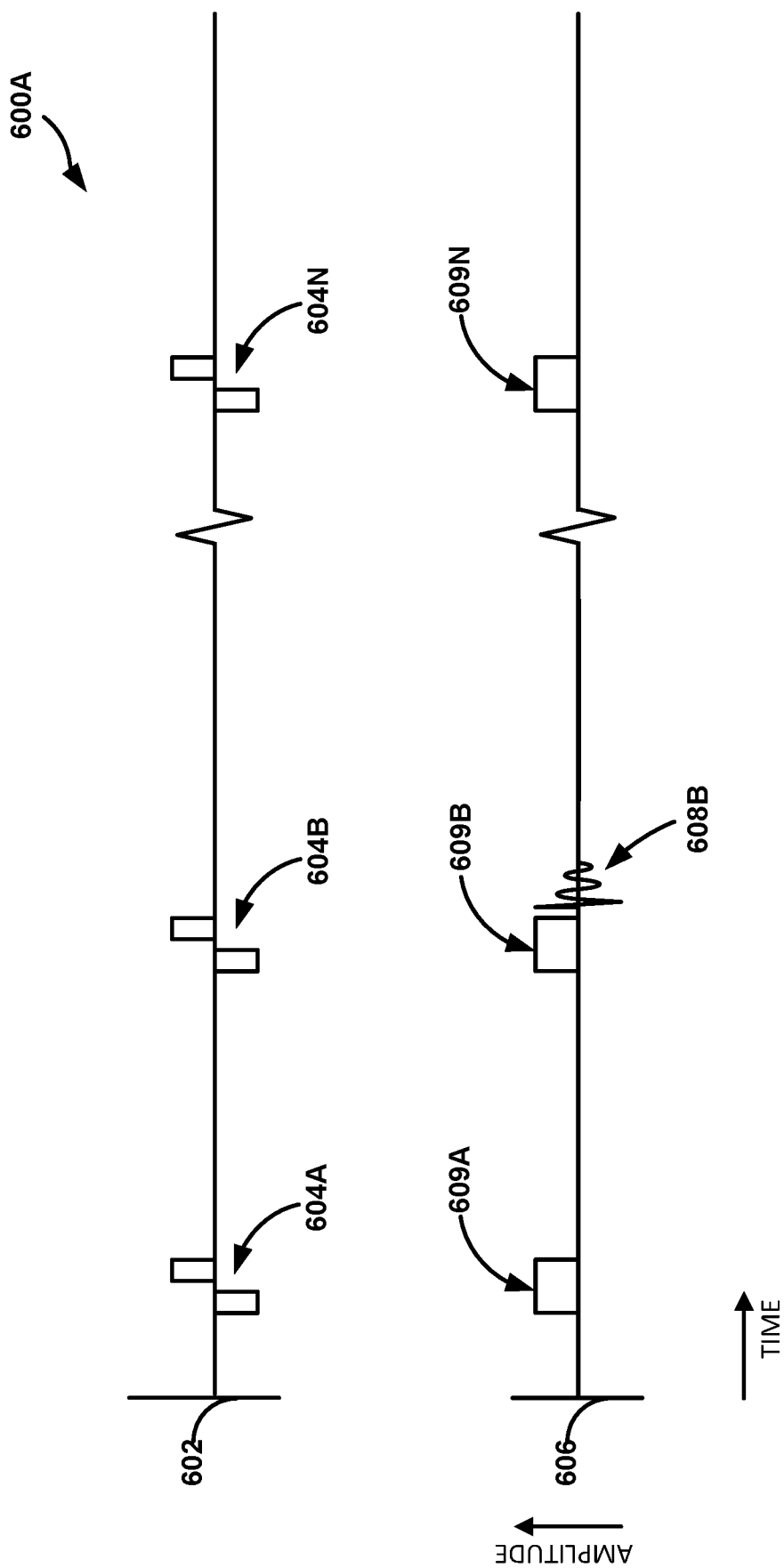
FIG. 6A is a timing diagram illustrating an example of electrical stimulation pulses, respective stimulation signals, and respective sensed ECAPs, in accordance with one or more techniques of this disclosure.

FIG. 6A is a timing diagram 600A illustrating an example of electrical stimulation pulses, respective stimulation signals, and respective sensed ECAPs, in accordance with one or more techniques of this disclosure. For convenience, FIG. 6A is described with reference to IMD 200 of FIG. 2. As illustrated, timing diagram 600A includes first channel 602, a plurality of stimulation pulses 604A-604N (collectively "stimulation pulses 604"), second channel 606, a plurality of respective ECAPs 608A-608N (collectively "ECAPs 608"), and a plurality of stimulation signals 609A-609N (collectively "stimulation signals 609"). In some examples, stimulation pulses 604 may represent control pulses which are configured to elicit ECAPs 608 that are detectible by IMD 200, but this is not required. Stimulation pulses 604 may represent any type of pulse that is deliverable by IMD 200. In the example of FIG. 6A, IMD 200 can deliver therapy with control pulses instead of, or without, informed pulses.

Timing diagram 600A of FIG. 6A may be substantially the same as timing diagram 500A FIG. 5A except that stimulation pulse 604A and stimulation pulse 604N do not evoke an ECAP that is detectible by IMD 200. Although stimulation pulse 604B emits ECAP 608B, which is detectible by IMD 200, it may be the case that IMD 200 does not sense enough detectible ECAPs for therapy determination in the example of FIG. 6A. As such, IMD 200 may determine one or more characteristics of stimulation signals 609 in order to determine one or more parameters of upcoming stimulation pulses following stimulation pulse 604N. For example, IMD 200 may determine an amplitude of at least a portion of each stimulation signal of stimulation signals 609 and determine the one or more parameters of the upcoming stimulation pulses based on the determined amplitudes. Although stimulation signals 609 are illustrated as square pulses, stimulation signals 609 may include other shapes and/or waveforms, in some examples. In some examples, each stimulation signal of stimulation signals 509 may include two or more phases. Processing circuitry 210 of IMD 200 may analyze the two or more phases of stimulation signals 509 in order to determine therapy.

Figure 6B:
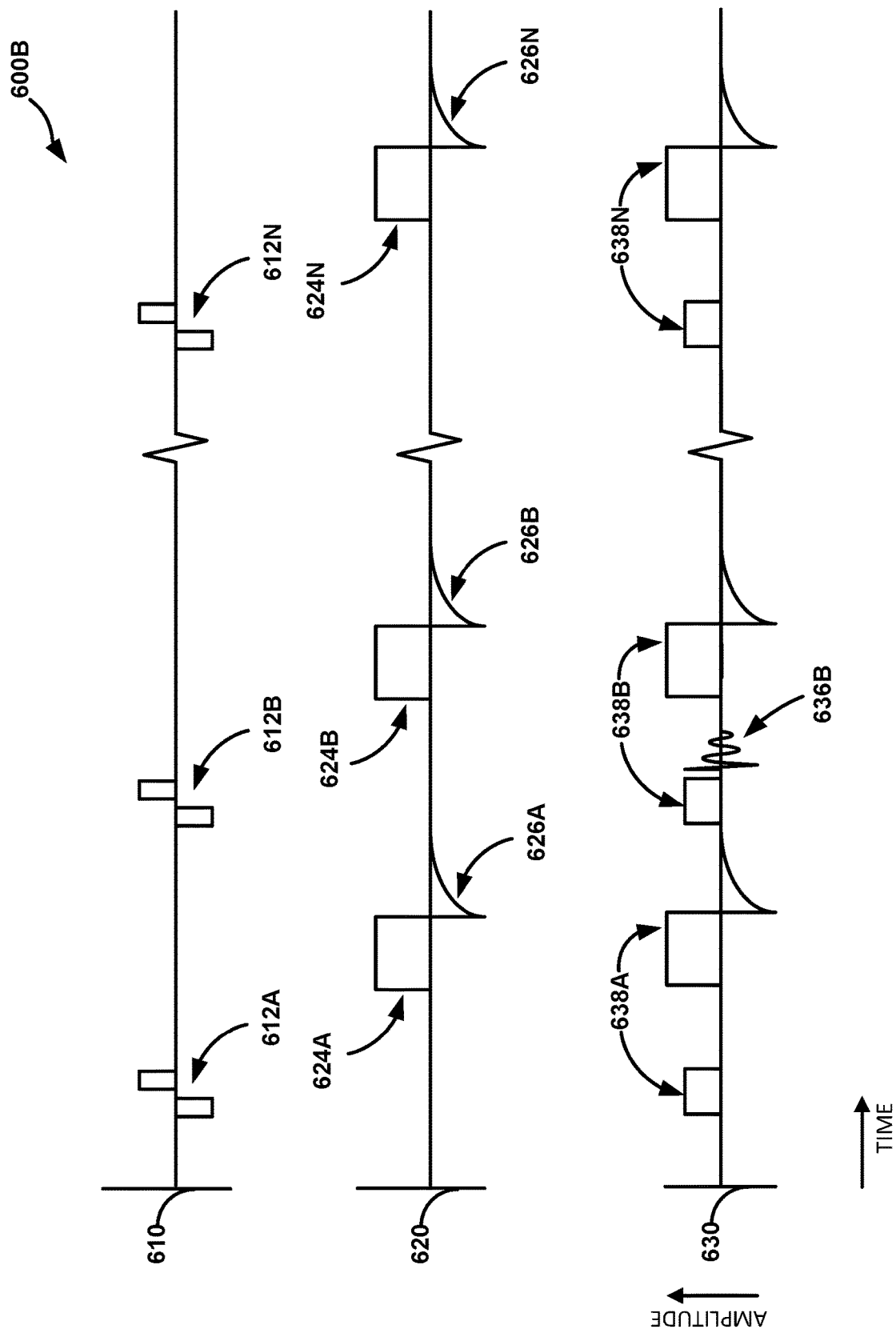
FIG. 6B is a timing diagram illustrating another example of electrical stimulation pulses, respective stimulation signals, and respective sensed ECAPs, in accordance with one or more techniques of this disclosure.

FIG. 6B is a timing diagram 600B illustrating another example of electrical stimulation pulses, respective stimulation signals, and respective sensed ECAPs, in accordance with one or more techniques of this disclosure. For convenience, FIG. 6B is described with reference to IMD 200 of FIG. 2. As illustrated, timing diagram 600B includes first channel 610, a plurality of control pulses 612A-612N (collectively "control pulses 612"), second channel 620, a plurality of informed pulses 624A-624N (collectively "informed pulses 624") including passive recharge phases 626A-626N (collectively "passive recharge phases 626"), third channel 630, a plurality of respective ECAPs 636A-636N (collectively "ECAPs 636"), and a plurality of stimulation signals 638A-638N (collectively "stimulation signals 638").

Timing diagram 600B of FIG. 6B may be substantially the same as timing diagram 500B FIG. 5B except that control pulse 612A and control pulse 612N do not evoke an ECAP that is detectible by IMD 200. Although control pulse 612B emits ECAP 636B, which is detectible by IMD 200, it may be the case that IMD 200 does not sense enough detectible ECAPs for therapy determination in the example of FIG. 6B. As such, IMD 200 may determine one or more characteristics of stimulation signals 638 in order to determine one or more parameters of upcoming stimulation pulses following control pulse 612N. For example, IMD 200 may determine an amplitude of at least a portion of each stimulation signal of stimulation signals 638 and determine the one or more parameters of the upcoming stimulation pulses based on the determined amplitudes. Although stimulation signals 638 are illustrated as square pulses, stimulation signals 639 may include other shapes and/or waveforms, in some examples. In some examples, each stimulation signal of stimulation signals 638 may include two or more phases. Processing circuitry 210 of IMD 200 may analyze the two or more phases of stimulation signals 638 in order to determine therapy.

Figure 7:
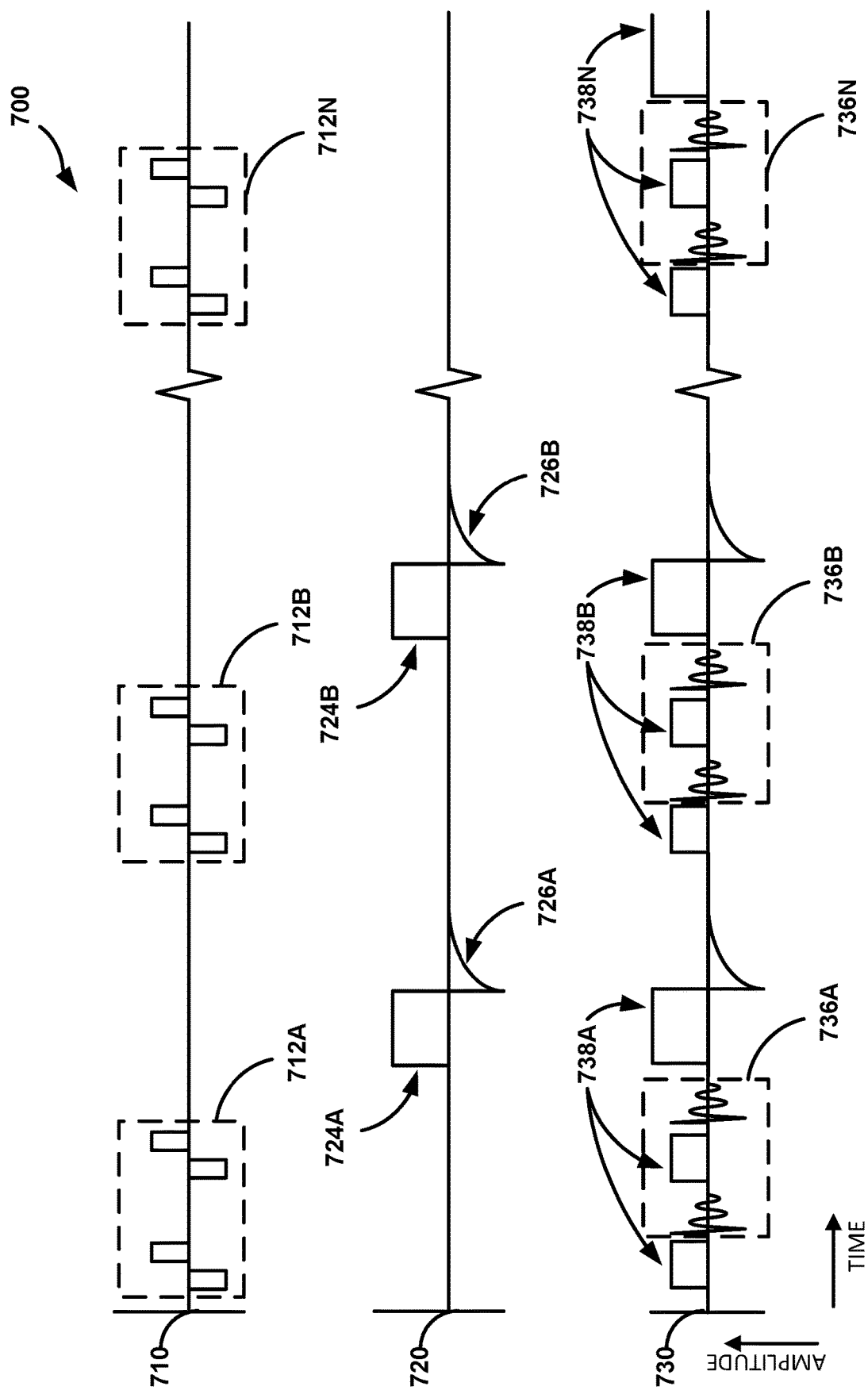
FIG. 7 is a timing diagram illustrating another example of electrical stimulation pulses, respective stimulation signals, and respective ECAPs, in accordance with one or more techniques of this disclosure.

FIG. 7 is a timing diagram 700 illustrating another example of electrical stimulation pulses, respective stimulation signals, and respective ECAPs, in accordance with one or more techniques of this disclosure. For convenience, FIG. 7 is described with reference to IMD 200 of FIG. 2. As illustrated, timing diagram 700 includes first channel 710, a plurality of control pulses 712A-712N (collectively "control pulses 712"), second channel 720, a plurality of informed pulses 724A-724B (collectively "informed pulses 724") including passive recharge phases 726A-726B (collectively "passive recharge phases 726"), third channel 730, a plurality of respective ECAPs 736A-736N (collectively "ECAPs 736"), and a plurality of stimulation interference signals 738A-738N (collectively "stimulation interference signals 738"). FIG. 7 may be substantially similar to FIG. 5B, except for the differences detailed below.

Two or more (e.g. two) control pulses 712 may be delivered during each time event (e.g., window) of a plurality of time events, and each time event represents a time between two consecutive informed pulses 724. For example, during each time event, a first control pulse may be directly followed by a first respective ECAP, and subsequent to the completion of the first respective ECAP, a second control pulse may be directly followed by a second respective ECAP. Informed pulses may commence following the second respective ECAP. In other examples not illustrated here, three or more control pulses 712 may be delivered, and respective ECAP signals sensed, during each time event of the plurality of time events.

Figure 8:
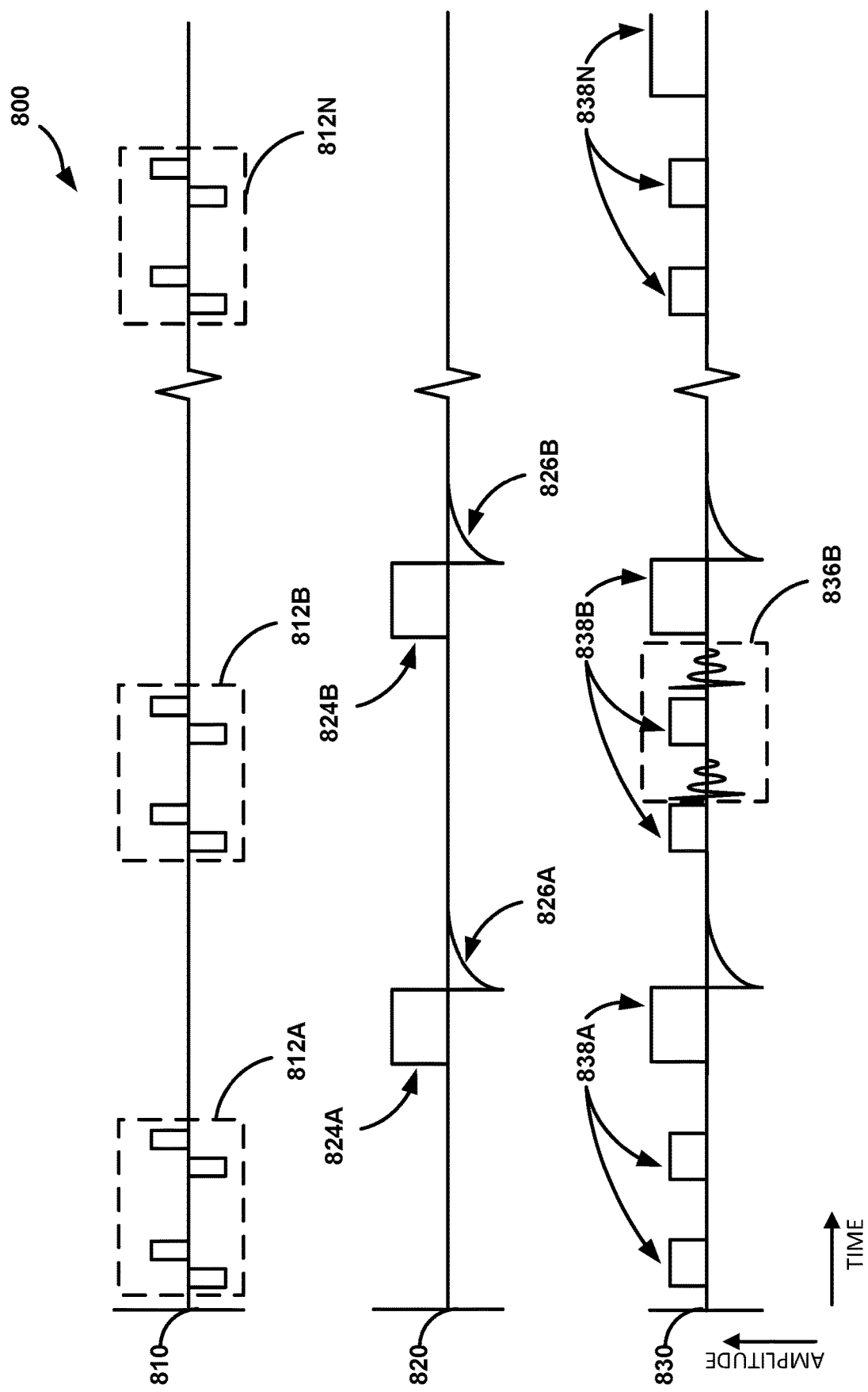
FIG. 8 is a timing diagram illustrating another example of electrical stimulation pulses, respective stimulation signals, and respective ECAPs, in accordance with one or more techniques of this disclosure.

FIG. 8 is a timing diagram 800 illustrating another example of electrical stimulation pulses, respective stimulation signals, and respective ECAPs, in accordance with one or more techniques of this disclosure. For convenience, FIG. 8 is described with reference to IMD 200 of FIG. 2. As illustrated, timing diagram 800 includes first channel 810, a plurality of control pulses 812A-812N (collectively "control pulses 812"), second channel 820, a plurality of informed pulses 824A-824B (collectively "informed pulses 824") including passive recharge phases 826A-826B (collectively "passive recharge phases 826"), third channel 830, respective ECAPs 836B (collectively "ECAPs 836"), and a plurality of stimulation interference signals 838A-838N (collectively "stimulation interference signals 838"). Timing diagram 800 of FIG. 8 may be substantially the same as timing diagram 700 FIG. 7 except that control pulses 812A and control pulses 812N do not evoke ECAPs that are detectible by IMD 200. Although control pulses 812B emit ECAPs 836B, which are detectible by IMD 200, it may be the case that IMD 200 does not sense enough detectible ECAPs for therapy determination in the example of FIG. 8. As such, IMD 200 may determine one or more characteristics of stimulation signals 838 in order to determine one or more parameters of upcoming stimulation pulses following control pulses 812N.

Figure 9:
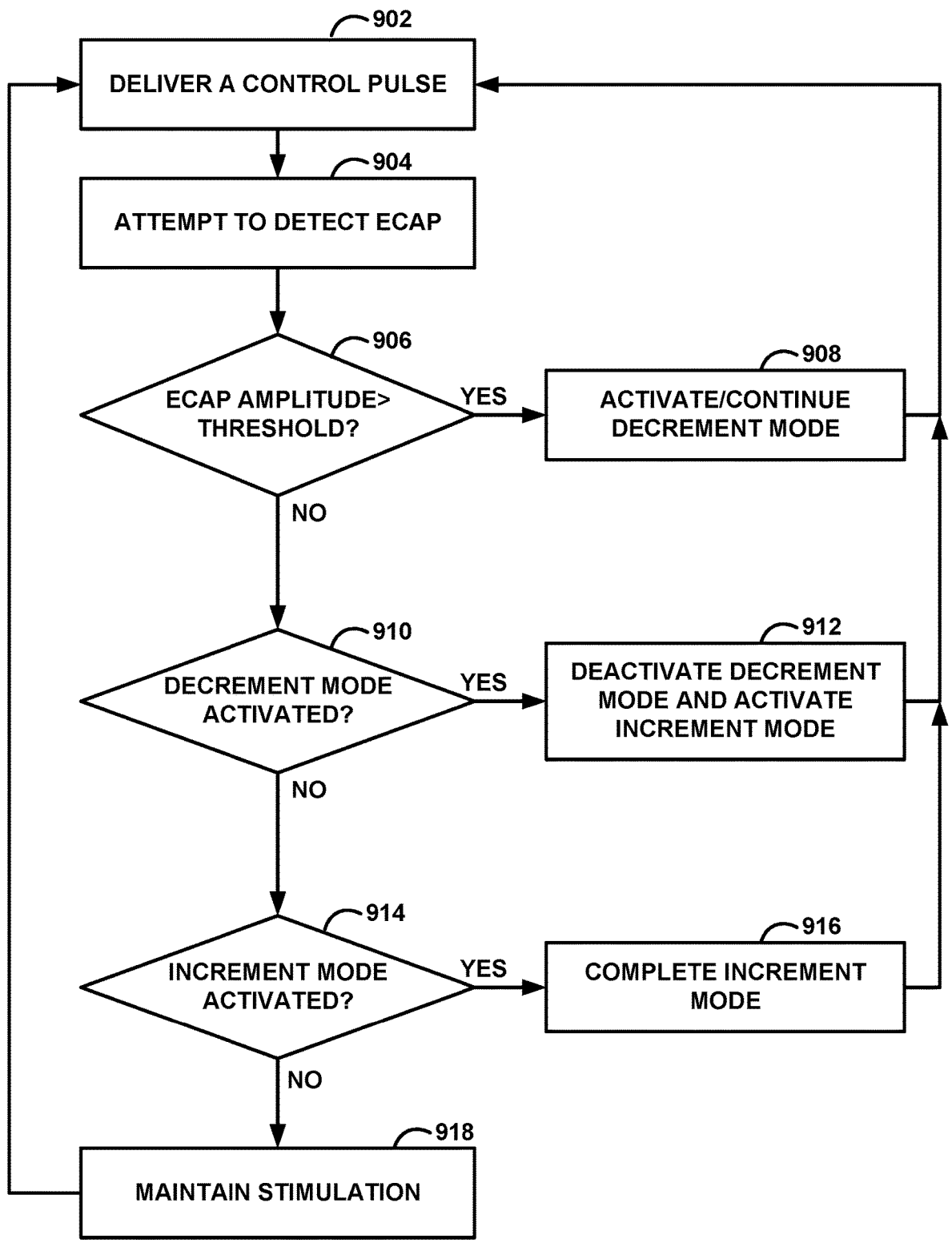
FIG. 9 is a flow diagram illustrating an example operation for controlling stimulation based on one or more sensed ECAPs, in accordance with one or more techniques of this disclosure.

FIG. 9 is a flow diagram illustrating an example operation for controlling stimulation based on one or more sensed ECAPs, in accordance with one or more techniques of this disclosure. For convenience, FIG. 9 is described with respect to IMD 200 of FIG. 2. However, the techniques of FIG. 9 may be performed by different components of IMD 200 or by additional or alternative medical devices.

Stimulation generation circuitry 202 of IMD 200 may deliver electrical stimulation therapy to a patient (e.g., patient 105). In order to control the electrical stimulation therapy, processing circuitry 210 may direct the delivery of at least some stimulation pulses according to therapy stimulation programs 214 of storage device 212, where the electrical stimulation therapy may include a plurality of control pulses and/or informed pulses. Informed pulses may, in some cases, produce ECAPs detectable by IMD 200. However, in other cases, an electrical polarization of an informed pulse may interfere with sensing of an ECAP responsive to the informed pulse. In some examples, to evoke ECAPs which are detectable by IMD 200, stimulation generation circuitry 202 delivers a plurality of control pulses, the plurality of control pulses being interleaved with at least some informed pulses of the plurality of informed pulses. Processing circuitry 210 may control the delivery of control pulses according to ECAP test stimulation programs or ECAP storage instructions 216. Since the control pulses may be interleaved with the informed pulses, sensing circuitry 206 of IMD 200 may detect a plurality of ECAPs, where sensing circuitry 206 is configured to detect each ECAP of the plurality of ECAPs after a control pulse of the plurality of control pulses and prior to a subsequent informed pulse of the plurality of informed pulses. In this way, IMD 200 may evoke the plurality of ECAPs in target tissue by delivering control pulses without the informed pulses obstructing IMD 200 from sensing the ECAPs.

As illustrated in FIG. 9, processing circuitry 210 directs stimulation generation circuitry 202 to deliver a control pulse (902). Stimulation generation circuitry 202 may deliver the control pulse to target tissue of patient 105 via any combination of electrodes 232, 234 of leads 230. In some examples, the control pulse may include a balanced, bi-phasic square pulse that employs an active recharge phase. However, in other examples, the control pulse may include a monophasic pulse followed by a passive recharge phase. In other examples, the control pulse may include an imbalanced bi-phasic portion and a passive recharge portion. Although not necessary, a bi-phasic control pulse may include an interphase interval between the positive and negative phase to promote propagation of the nerve impulse in response to the first phase of the bi-phasic pulse. The control pulse may have a pulse width of 300 µs, such as a bi-phasic pulse with each phase having a duration of approximately 100 µs.

After delivering the control pulse, IMD 200 attempts to detect an ECAP (904). For example, sensing circuitry 206 may monitor signals from any combination of electrodes 232, 234 of leads 230. In some examples, sensing circuitry 206 detects ECAPs from a particular combination of electrodes 232, 234. In some cases, the particular combination of electrodes for sensing ECAPs includes different electrodes than a set of electrodes 232, 234 used to deliver stimulation pulses. Alternatively, in other cases, the particular combination of electrodes used for sensing ECAPs includes at least one of the same electrodes as a set of electrodes used to deliver stimulation pulses to patient 105. In some examples, the particular combination of electrodes used for sensing ECAPs may be located on an opposite side of leads 230 from the particular combination of electrodes used to deliver stimulation pulses. IMD 200 may detect an ECAP responsive to the control pulse. IMD 200 may measure one or more characteristics of the responsive ECAP, such as ECAP amplitude, ECAP duration, peak-to-peak durations, or any combination thereof. For example, to measure an amplitude of the ECAP, IMD 200 may determine a voltage difference between an N1 ECAP peak and a P2 ECAP peak. Processing circuitry 210 may store the ECAP signals, characteristic value, or any other related data as ECAP information.

At block 906, processing circuitry 210 determines if the ECAP amplitude of the responsive ECAP is greater than an ECAP amplitude threshold. If the ECAP amplitude is greater than the ECAP amplitude threshold ("YES" branch of block 906), processing circuitry 210 activates/continues a decrement mode (908) in IMD 200. For example, if the decrement mode is already "turned on" in IMD 200 when processing circuitry determines that the ECAP amplitude is greater than the ECAP amplitude threshold, then processing circuitry 210 maintains IMD 200 in the decrement mode. If the decrement mode is "turned off" in IMD 200 when processing circuitry determines that the ECAP amplitude is greater than the ECAP amplitude threshold, then processing circuitry 210 activates the decrement mode. In some examples, the decrement mode may be stored in storage device 212 as a part of control policy 213. The decrement mode may be a set of instructions which causes IMD 200 to decrease one or more parameter values of each consecutive informed pulse from a respective predetermined value (e.g., a value determined by a stimulation program) and decrease one or more parameter values of each consecutive control pulse from a respective predetermined value (e.g., a value determined by a stimulation program). In other words, the parameter values may be reduced from the values that IMD 200 would use to define respective pulses in the absence of the ECAP amplitude exceeding the threshold ECAP amplitude. For example, when the decrement mode is activated, processing circuitry 210 may decrease an electric current amplitude of each consecutive informed pulse delivered by IMD 200 and decrease an electric current amplitude of each consecutive control pulse delivered by IMD 200. After processing circuitry 210 activates/continues the decrement mode, the example operation may return to block 902 and IMD 200 may deliver another control pulse.

If the ECAP amplitude is not greater than the ECAP amplitude threshold ("NO" branch of block 906), processing circuitry 210 determines whether the decrement mode is activated in IMD 200 (910). If the decrement mode is activated in IMD 200 ("YES" branch of block 910), processing circuitry 210 deactivates the decrement mode and activates an increment mode (912) in IMD 200. In some examples, the increment mode may be stored in storage device 212 as a part of control policy 213. The increment mode may be a set of instructions which causes IMD 200 to increase one or more parameter values of each consecutive informed pulse and increase one or more parameter values of each consecutive control pulse. For example, when the increment mode is activated, processing circuitry 210 may increase an electric current amplitude of each consecutive informed pulse delivered by IMD 200 and increase an electric current amplitude of each consecutive control pulse delivered by IMD 200. After processing circuitry 210 deactivates the decrement mode and activates the increment mode, the example operation may return to block 902 and IMD 200 may deliver another control pulse.

When the example operation of FIG. 9 arrives at block 910 and the decrement mode is not activated in IMD 200 ("NO" branch of block 910), processing circuitry 210 determines whether the increment mode is activated (914) in IMD 200. If the increment mode is activated in IMD 200 ("YES" branch of block 914), processing circuitry 210 may complete the increment mode (916) in IMD 200. In some examples, to complete the increment mode, processing circuitry 210 may increase the electric current amplitude of each consecutive informed pulse delivered by IMD 200 and increase the electric current amplitude of each consecutive control pulse delivered by IMD 200 until the pulse amplitude of the stimulation pulses reach an electric current amplitude (e.g., a predetermined value that may be set by the stimulation program selected for therapy) of the stimulation pulses delivered by IMD 200 prior to the activation of the decrement mode. In this manner, the process may not be referred to as a fully closed-loop system. Put another way, IMD 200 may monitor the high end (ECAP amplitude threshold) for adjusting stimulation pulses instead of monitoring any low end of the sensed ECAP amplitude. For example, IMD 200 may continue to increase the current amplitude of consecutive informed pulses without any feedback from the sensed ECAP, unless the sensed ECAP value again exceeds the ECAP amplitude threshold. After processing circuitry 210 completes the increment mode, the example operation may return to block 902 and IMD 200 may deliver another control pulse. When the example operation of FIG. 9 arrives at block 914 and the increment mode is not activated in IMD 200 ("NO" branch of block 914), processing circuitry 210 maintains stimulation (918) in IMD 200. Although FIG. 9 describes adjusting both informed pulses and control pulses, the technique of FIG. 9 may also apply when IMD 200 is delivering only control pulses (e.g., without informed pulses) to the patient for therapy.

Figure 10:
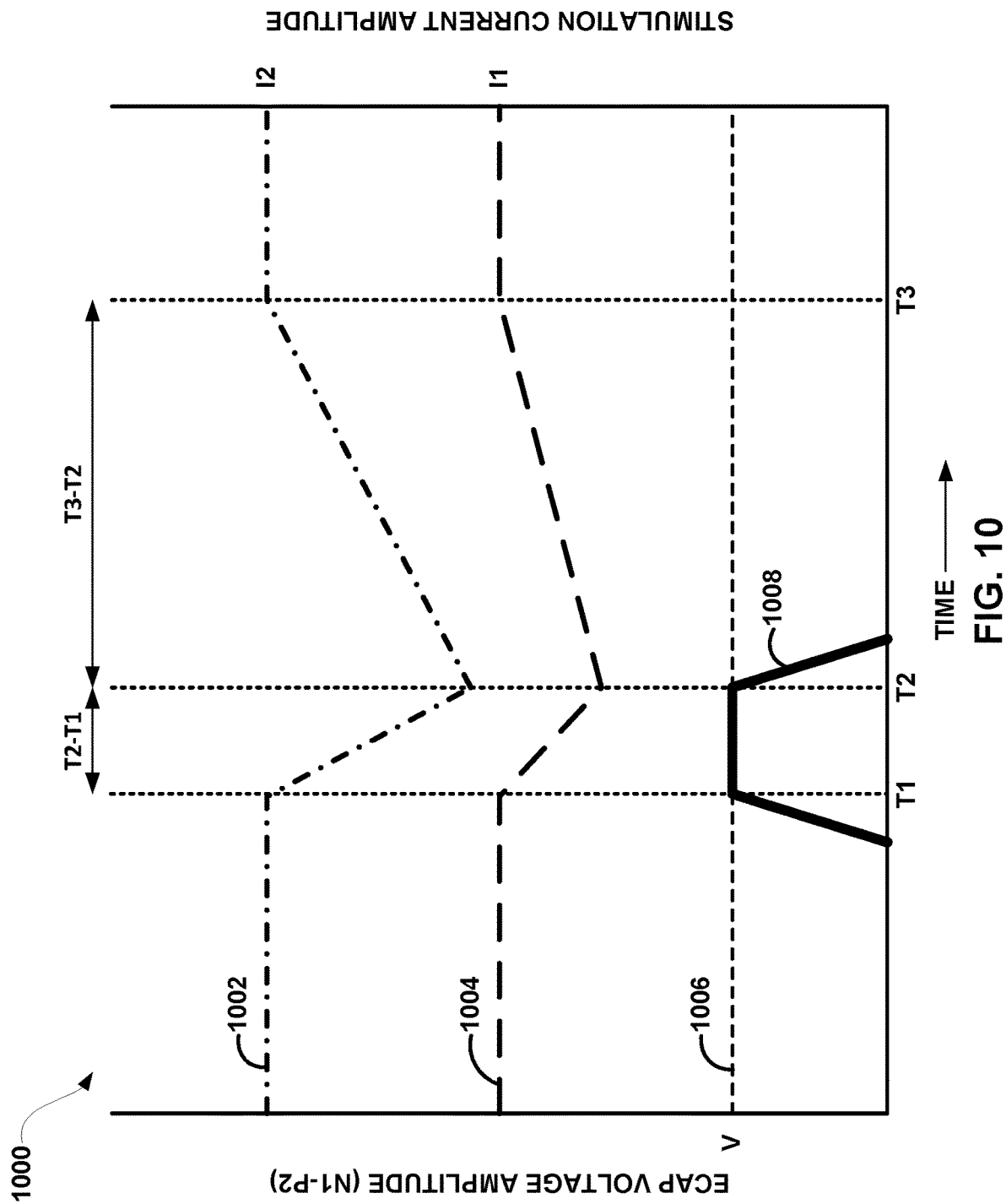
FIG. 10 illustrates a voltage/current/time graph which plots control pulse current amplitude, informed pulse current amplitude, ECAP voltage amplitude, and second ECAP voltage amplitude as a function of time, in accordance with one or more techniques of this disclosure.

FIG. 10 illustrates a voltage/current/time graph 1000 which plots control pulse current amplitude 1002, informed pulse current amplitude 1004, ECAP voltage amplitude 1008, and second ECAP voltage amplitude 1010 as a function of time, in accordance with one or more techniques of this disclosure. Additionally, FIG. 10 illustrates a threshold ECAP amplitude 1006. For convenience, FIG. 10 is described with respect to IMD 200 of FIG. 2. However, the techniques of FIG. 10 may be performed by different components of IMD 200 or by additional or alternative medical devices.

Voltage/current/time graph 1000 illustrates a relationship between sensed ECAP voltage amplitude and stimulation current amplitude. For example, control pulse current amplitude 1002 and informed pulse current amplitude 1004 are plotted alongside ECAP voltage amplitude 1008 as a function of time, thus showing how stimulation current amplitude changes relative to ECAP voltage amplitude. In some examples, IMD 200 delivers a plurality of control pulses and a plurality of informed pulses at control pulse current amplitude 1002 and informed pulse current amplitude 1004, respectively. Initially, IMD 200 may deliver a first set of control pulses, where IMD 200 delivers the first set of control pulses at current amplitude I2. Additionally, IMD 200 may deliver a first set of informed pulses, where IMD 200 delivers the first set of control pulses at current amplitude I1. I1 and I2 may be referred to as a predetermined value for the amplitude of respective control and informed pulses. This predetermined value may be a programmed value or otherwise selected value that a stimulation program has selected to at least partially define stimulation pulses to the patient in the absence of transient conditions (e.g., when the ECAP amplitude is below a threshold ECAP value). The first set of control pulses and the first set of informed pulses may be delivered prior to time T1. In some examples, I1 is 8 milliamps (mA) and I2 is 4 mA. Although control pulse current amplitude 1002 is shown as greater than informed pulse current amplitude 1004, control pulse current amplitude 1002 may be less than or the same as informed pulse current amplitude 1004 in other examples.

While delivering the first set of control pulses and the first set of informed pulses, IMD 200 may record ECAP voltage amplitude 1008. During dynamic and transient conditions which occur in patient 105 such as coughing, sneezing, laughing, Valsalva maneuvers, leg lifting, cervical motions, or deep breathing, ECAP voltage amplitude 1008 may increase if control pulse current amplitude 1002 and informed pulse current amplitude 1004 are held constant. This increase in ECAP voltage amplitude 1008 may be caused by a reduction in the distance between the electrodes and nerves. For example, as illustrated in FIG. 10, ECAP voltage amplitude 1008 may increase prior to time T1 while stimulation current amplitude is held constant. An increasing ECAP voltage amplitude 1008 may indicate that patient 105 is at risk of experiencing transient overstimulation due to the control pulses and the informed pulses delivered by IMD 200. To prevent patient 105 from experiencing transient overstimulation, IMD 200 may decrease control pulse current amplitude 1002 and informed pulse current amplitude 1004 in response to ECAP voltage amplitude 1008 exceeding the threshold ECAP amplitude 1006. For example, if IMD 200 senses an ECAP having an ECAP voltage amplitude 1008 meeting or exceeding threshold ECAP amplitude 1006, as illustrated in FIG. 10 at time T1, 1 MB 200 may enter a decrement mode where control pulse current amplitude 1002 and informed pulse current amplitude 1004 are decreased. In some examples, the threshold ECAP amplitude 1006 is selected from a range of approximately 5 microvolts (μV) to approximately 30 μV, or from a range of approximately 10 microvolts (μV) to approximately 20 μV. For example, the threshold ECAP amplitude 1006 is 15 μV. In other examples, the threshold ECAP amplitude 1006 is less than or equal to 5 μV or greater than or equal to 30 μV.

IMD 200 may respond relatively quickly to the ECAP voltage amplitude 1008 exceeding the threshold ECAP amplitude 1006. For example, IMD may be configured to detect threshold exceeding ECAP amplitudes within 20 milliseconds (ms). If IMD 200 delivers control pulses at a frequency of 50 Hz, the period of time for a single sample that includes delivering the control pulse and detecting the resulting ECAP signal may be 20 ms or less. However, since an ECAP signal may occur within one or two ms of delivery of the control pulse, IMD 200 may be configured to detect an ECAP signal exceeding the threshold ECAP amplitude in less than 10 ms. For transient conditions, such as a patient coughing or sneezing, these sampling periods would be sufficient to identify ECAP amplitudes exceeding the threshold and a responsive reduction in subsequent pulse amplitudes before the ECAP amplitude would have reached higher levels that may have been uncomfortable for the patient.

The decrement mode may, in some cases, be stored in storage device 212 of IMD 200 as a part of control policy 213. In the example illustrated in FIG. 10, the decrement mode is executed by IMD 200 over a second set of control pulses and a second set of informed pulses which occur between time T1 and time T2. In some examples, to execute the decrement mode, IMD 200 decreases the control pulse current amplitude 1002 of each control pulse of the second set of control pulses according to a first function with respect to time. In other words, 1 MB 200 decreases each consecutive control pulse of the second set of control pulses proportionally to an amount of time elapsed since a previous control pulse. Additionally, during the decrement mode, IMD 200 may decrease the informed pulse current amplitude 1004 of each informed pulse of the second set of informed pulses according to a second function with respect to time. Although linear first and second functions are shown, the first and/or second function may be non-linear, such as logarithmic (e.g., the rate of change decreases over time), exponential (e.g., the rate of change increases over time), parabolic, step-wise, multiple different functions, etc., in other examples. During a period of time in which IMD 200 is operating in the decrement mode (e.g., time interval T2-T1), ECAP voltage amplitude 1008 of ECAPs sensed by IMD 200 may be greater than or equal to threshold ECAP amplitude 1006.

In the example illustrated in FIG. 2, IMD 200 may sense an ECAP at time T2, where the ECAP has an ECAP voltage amplitude 1008 that is less than threshold ECAP amplitude 1006. The ECAP sensed at time T2 may, in some cases, be the first ECAP sensed by IMD 200 with a below-threshold amplitude since IMD 200 began the decrement mode at time T1. Based on sensing the ECAP at time T2, IMD 200 may deactivate the decrement mode and activate an increment mode. The increment mode may, in some cases, be stored in storage device 212 of IMD 200 as a part of control policy 213. IMD 200 may execute the increment mode over a third set of control pulses and a third set of informed pulses which occur between time T2 and time T3. In some examples, to execute the increment mode, IMD 200 increases the control pulse current amplitude 1002 of each control pulse of the third set of control pulses according to a third function with respect to time. In other words, IMD 200 increases each consecutive control pulse of the third set of control pulses proportionally to an amount of time elapsed since a previous control pulse. Additionally, during the increment mode, IMD 200 may increase the informed pulse current amplitude 1004 of each informed pulse of the third set of informed pulses according to a fourth function with respect to time.

As shown in FIG. 10, IMD 200 is configured to decrease amplitude at a faster rate than increasing amplitude after ECAP voltage amplitude 1008 falls below threshold ECAP amplitude 1006. In other examples, the rate of change during the decrement mode and increment mode may be similar. In other examples, IMD 200 may be configured to increase amplitude of informed and control pulses at a faster rate than when decreasing amplitude. The rate of change in amplitude of the pulses may be relatively instantaneously (e.g., a very fast rate) in other examples. For example, in response to ECAP voltage amplitude 1008 exceeding threshold ECAP amplitude 1006, IMD 200 may immediately drop the amplitude of one or both of control pulse current amplitude 1002 or informed pulse current amplitude 1004 to a predetermined or calculated value. Then, in response to ECAP voltage amplitude 1008 dropping back below threshold ECAP amplitude 1006, IMD 200 may enter increment mode as described above.

When control pulse current amplitude 1002 and informed pulse current amplitude 1004 return to current amplitude I2 and current amplitude I1, respectively, IMD 200 may deactivate the increment mode and deliver stimulation pulses at constant current amplitudes. By decreasing stimulation in response to ECAP amplitudes exceeding a threshold and subsequently increasing stimulation in response to ECAP amplitudes falling below the threshold, IMD 200 may prevent patient 105 from experiencing transient overstimulation or decrease a severity of transient overstimulation experienced by patient 105, whether the decrease is in terms of the length of the experience, the relative intensity, or both.

FIG. 10 is described in the situation in which IMD 200 delivers both control pulse and informed pulses. However, IMD 200 may apply the technique of FIG. 10 to the situation in which only control pulses are delivered to provide therapy to the patient. In this manner, IMD 200 would similarly enter a decrement mode or increment mode for control pulse current amplitude 1002 based on the detected ECAP voltage amplitude 1008 without adjusting the amplitude or other parameter of any other type of stimulation pulse.

Figure 11:
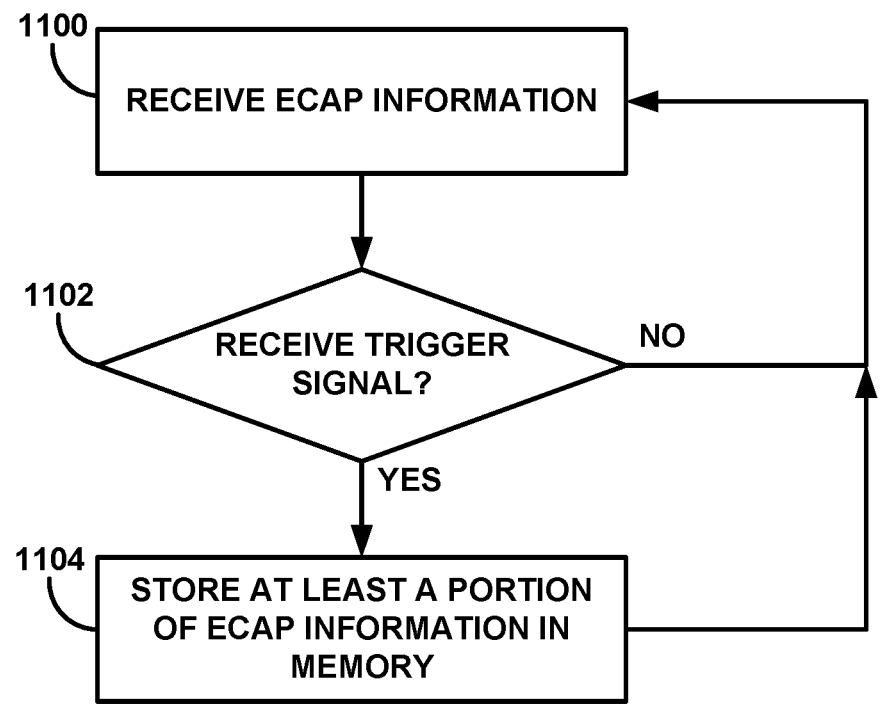
FIG. 11 is a flow diagram illustrating an example operation for controlling storage of ECAP information.

FIG. 11 is a flow diagram illustrating an example operation for controlling storage of ECAP information. FIG. 11 is described with respect to IMD 200, processing circuitry 210 and long-term memory 220 of FIG. 2. However, the techniques of FIG. 11 may be performed by different components of IMD 200, IMD 110, external programmer 150, or by additional or alternative medical devices.

As shown in the example of FIG. 11, processing circuitry 210 receives ECAP information (1100). Processing circuitry 210 may receive ECAP information from sensing circuitry 206. In some examples, processing circuitry 210 may generate some or all of the ECAP information from ECAP signals received from sensing circuitry 206. Typically, processing circuitry 210 may store the ECAP information in temporary memory 218. If processing circuitry 210 does not receive a trigger signal ("NO" branch of block 1102), processing circuitry 210 may continue to receive ECAP information and continue normal function such as adjusting stimulation parameters based on an ECAP characteristic value.

If processing circuitry 210 does receive a trigger signal ("YES" branch of block 1102), processing circuitry 210 stores at least a portion of the ECAP information in a memory (1104). For example, processing circuitry 210 may move at least a portion of ECAP information from temporary memory 218 to long-term memory 220. In some examples, processing circuitry 210 may store other information in addition to the ECAP information. For example, processing circuitry 210 may also store acceleration data (e.g., posture state and/or activity information) with the ECAP information. Processing circuitry 210 may also store time stamp or other data with the ECAP information and any other information in order to correlate the information with events that occurred at the same time, for example.

Figure 12:
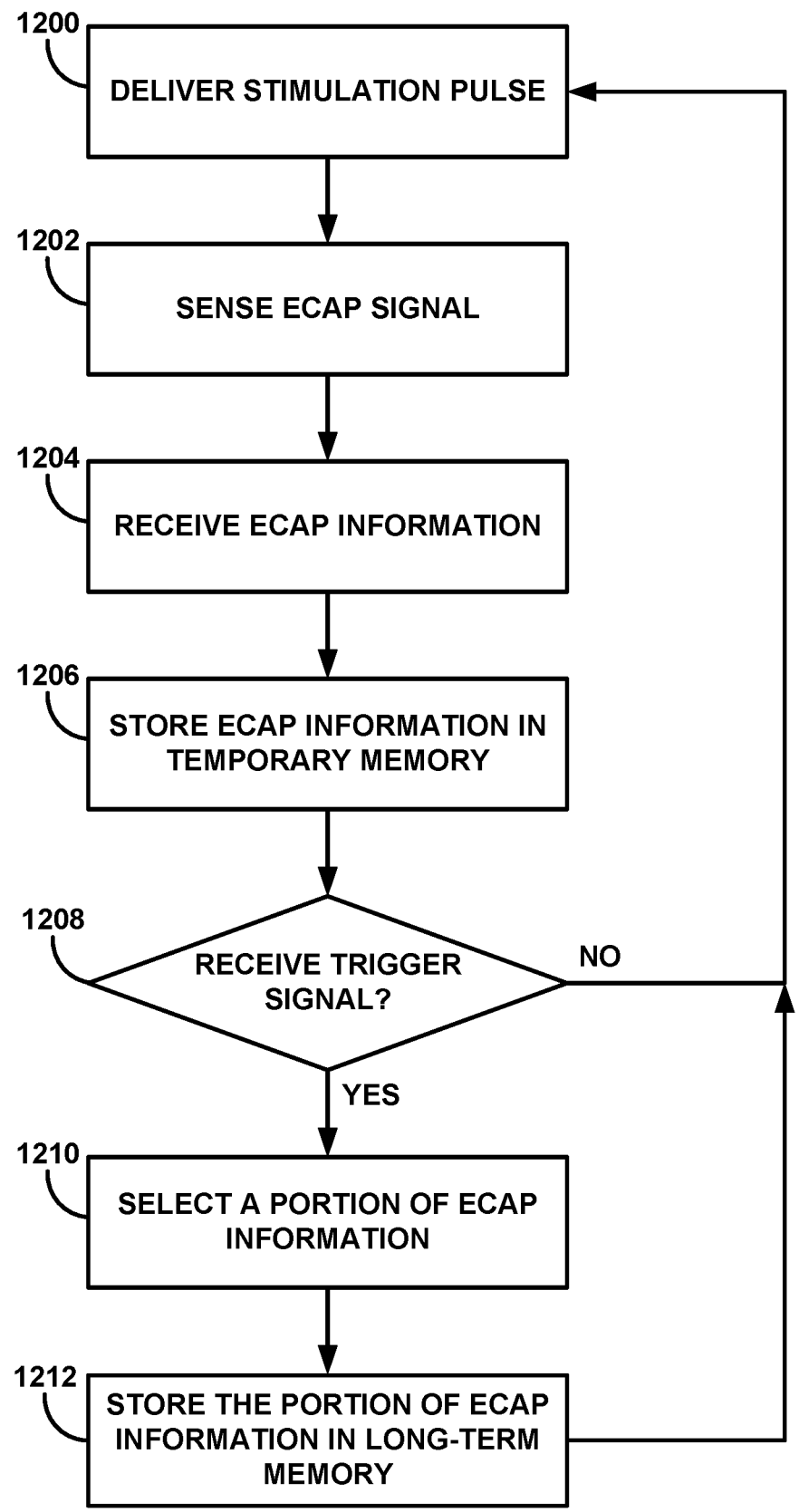
FIG. 12 is a flow diagram illustrating an example operation for sensing ECAP signals and storing ECAP information.

FIG. 12 is a flow diagram illustrating an example operation for sensing ECAP signals and storing ECAP information. FIG. 12 is described with respect to IMD 200, processing circuitry 210 and long-term memory 220 of FIG. 2. However, the techniques of FIG. 12 may be performed by different components of IMD 200, IMD 110, external programmer 150, or by additional or alternative medical devices.

As shown in the example of FIG. 12, processing circuitry 210 controls stimulation generation circuitry 202 to deliver a stimulation pulse (1200). The stimulation pulse may or may not be configured to contribute to therapy, but an ECAP signal may be detected as a result of the stimulation pulse. Sensing circuitry 206 the senses the resulting ECAP signal (1202). Processing circuitry 210 then receives ECAP information from sensing circuitry 206 (1204). The ECAP information may be a digitized waveform or include already determined ECAP characteristic values. Processing circuitry 210 then stores the received ECAP information in temporary memory 2018 (1206).

If processing circuitry 210 does not receive a trigger signal ("NO" branch of block 1208), processing circuitry 210 may continue to deliver stimulation pulses (1200) and receive ECAP information and continue normal function such as adjusting stimulation parameters based on an ECAP characteristic value. If processing circuitry 210 does receive a trigger signal ("YES" branch of block 1208), processing circuitry 210 selects a portion of the ECAP information from temporary memory 218 (1210). For example, processing circuitry 210 may select ECAP information that represents ECAP signals sensed over a predetermined period of time (e.g., seconds, minutes, or longer) or a predetermined number of ECAP signals. Processing circuitry 210 then stores the selected portion of the ECAP information in long-term memory 220 (1212). For example, processing circuitry 210 may move at least a portion of ECAP information from temporary memory 218 to long-term memory 220. In some examples, processing circuitry 210 may continue to select ECAP information received for a predetermined period of time after receiving the trigger signal and store that new ECAP information in long-term memory 220. This ECAP information before and after the trigger signal may be flagged as associated with a single event. Processing circuitry 210 may then continue to deliver another stimulation pulse (1200). In some examples, storing the selected portion of the ECAP information in long-term memory enables the system to determine and/or display data temporally close to the trigger signal that may represent conditions of the patient before and/or after the trigger signal. In some examples, processing circuitry 210 may store other information in addition to the ECAP information in the temporary memory and the long-term memory as requested. For example, processing circuitry 210 may also store acceleration data (e.g., posture state and/or activity information) with the ECAP information. Processing circuitry 210 may also store time stamp or other data with the ECAP information and any other information in order to correlate the information with events that occurred at the same time, for example.

Figure 13:
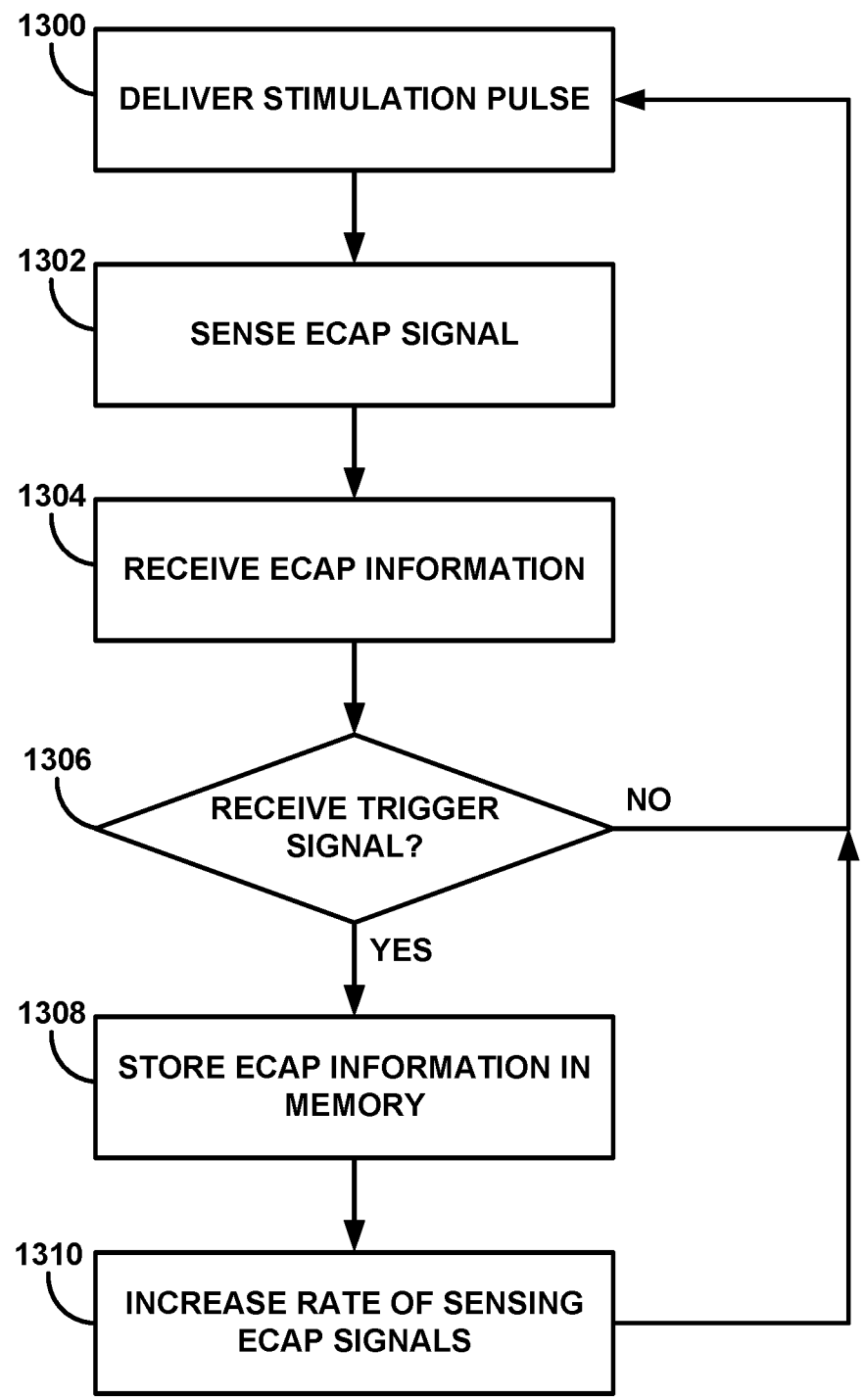
FIG. 13 is a flow diagram illustrating an example operation for adjusting a rate of sensing ECAP signals.

FIG. 13 is a flow diagram illustrating an example operation for adjusting a rate of sensing ECAP signals. FIG. 13 is described with respect to IMD 200, processing circuitry 210 and long-term memory 220 of FIG. 2. However, the techniques of FIG. 13 may be performed by different components of IMD 200, IMD 110, external programmer 150, or by additional or alternative medical devices.

As shown in the example of FIG. 12, processing circuitry 210 controls stimulation generation circuitry 202 to deliver a stimulation pulse (1300). The stimulation pulse may or may not be configured to contribute to therapy, but an ECAP signal may be detected as a result of the stimulation pulse. Sensing circuitry 206 the senses the resulting ECAP signal (1302). Processing circuitry 210 then receives ECAP information from sensing circuitry 206 (1304). The ECAP information may be a digitized waveform or include already determined ECAP characteristic values.

If processing circuitry 210 does not receive a trigger signal ("NO" branch of block 1208), processing circuitry 210 may continue to deliver stimulation pulses (1300) and receive ECAP information and continue normal function such as adjusting stimulation parameters based on an ECAP characteristic value. If processing circuitry 210 does receive a trigger signal ("YES" branch of block 1306), processing circuitry 210 stores the ECAP information in a memory, such as long-term memory 202 (1308). In addition to storing the ECAP information, processing circuitry 210 increases the rate of sensing ECAP signals (1310). This increasing the rate of sensing may include increasing the rate at which processing circuitry 210 controls stimulation generation circuitry 202 to deliver stimulation pulses and the rate at which sensing circuitry captures ECAP signals elicited from each of the delivered stimulation pulses. In this manner, processing circuitry 210 can increase the fidelity of ECAP information may increasing the frequency at which ECAP signals are captured. It is noted that some or all of the techniques described in FIGS. 11, 12, and 13 may be used together. For example, processing circuitry 210 may store ECAP information in long-term memory and increase the rate of sensing ECAP signals to achieve higher fidelity ECAP information for later analysis. In some examples, processing circuitry 210 may store other information in addition to the ECAP information in the temporary memory and the long-term memory as requested. For example, processing circuitry 210 may also store acceleration data (e.g., posture state and/or activity information) with the ECAP information. Processing circuitry 210 may also store time stamp or other data with the ECAP information and any other information in order to correlate the information with events that occurred at the same time, for example.

This application generally describes the storing of ECAP information in long-term storage in response to receiving a trigger signal. However, additional or alternative information may be stored by the system in response to receiving the trigger signal. For example, the system may store local field potential (LFP) information in addition to, or instead of, the ECAP information described herein. The system may store LFP information representative of LFP signals sensed by one or more electrode combinations. The LFP signals may be sensed by one or more electrode combinations located near the spinal cord and/or in the brain. The system may store the LFP information and the ECAP information in a temporary memory and store both LFP information and ECAP information in the long-term memory in response to the trigger signal. In some examples, the system may sample the LFP signals are a higher, lower, or the same rate as the ECAP signal. The system may store the LFP information in the frequency domain. The system may be configured to control a display to present the ECAP information and LFP information (and/or other type of sensed physiological information) together overlapping in time to illustrate correlations between the ECAP information and LFP information. In other examples, the system may correlate the ECAP information with the LFP information to identify and/or confirm that one or more patient events occurred.

The following examples are described herein. Example 1: A system includes a memory; and processing circuitry configured to: receive evoked compound action potential (ECAP) information, wherein the ECAP information comprises information from a plurality of evoked compound action potential (ECAP) signals; receive a trigger signal requesting long-term storage of at least a portion of the ECAP information in the memory; and responsive to receiving the trigger signal, store the at least portion of the ECAP information in the memory.

Example 2: The system of example 1, further includes stimulation generation circuitry configured to deliver electrical stimulation to a patient, wherein the electrical stimulation therapy comprises a plurality of stimulation pulses; and sensing circuitry configured to sense the plurality of ECAP signals, wherein the sensing circuitry is configured to sense each ECAP signal of the plurality of ECAP signals elicited by a respective stimulation pulse of the plurality of stimulation pulses, wherein the processing circuitry is configured to receive the ECAP signals from the sensing circuitry as the ECAP information.

Example 3: The system of example 2, wherein the processing circuitry is configured to: responsive to receiving the trigger signal, control the sensing circuitry to increase a rate at which the sensing circuitry senses subsequent ECAP signals; and store subsequent ECAP information comprising the subsequent ECAP signals in the memory.

Example 4: The system of any of examples 1 through 3, wherein the ECAP information comprises at least one characteristic value representing respective ECAP signals of the plurality of ECAP signals, wherein the characteristic value comprises at least one of an amplitude value, a slope value, or an area under peak value.

Example 5: The system of any of examples 1 through 4, wherein the ECAP information comprises a plurality of waveforms representing respective ECAP signals of the plurality of ECAP signals.

Example 6: The system of any of examples 1 through 5, wherein the memory comprises a long-term memory, and wherein the processing circuitry is configured to store the received ECAP information in a temporary memory, and wherein the processing circuitry is configured to delete ECAP information stored in the temporary memory in response to a predetermined period of time elapsing.

Example 7: The system of any of examples 1 through 6, further comprising communication circuitry configured to transmit the stored ECAP information to an external device.

Example 8: The system of example 7, further comprising an external device comprising a display; and an implantable medical device comprising the memory, the processing circuitry, and the communication circuitry configured to transmit the stored ECAP information to the external device, wherein the external device is configured to present, via the display, one or more representations of the stored ECAP information.

Example 9: The system of any of examples 1 through 8, wherein the trigger signal comprises a request from an external device to store the ECAP information.

Example 10: The system of any of examples 1 through 9, wherein the trigger signal comprises a housing tap from a user, and wherein the processing circuitry is configured to receive the housing tap by: receiving accelerometer data from an accelerometer within a housing of an implantable medical device; and determining that the accelerometer data indicates a user tapped the implantable medical device.

Example 11: The system of any of examples 1 through 10, wherein the trigger signal comprises an indication that a characteristic of one ECAP signal of the plurality of ECAP signals exceeds a threshold.

Example 12: The system of any of examples 1 through 11, wherein the trigger signal comprises an indication that a user changed one or more stimulation parameter values defining electrical stimulation deliverable to a patient.

Example 13: The system of any of examples 1 through 12, wherein the processing circuitry is configured to, responsive to receiving the trigger signal, select the at least portion of the ECAP information representative of one or more ECAP signals of the plurality of ECAP signals sensed between an initial time and a final time, the initial time occurring at a first period of time prior to receiving the trigger signal and the final time occurring at a second period of time after receiving the trigger signal.

Example 14: The system of any of examples 1 through 13, wherein the processing circuitry adds a marker representative of the trigger signal to the at least portion of the ECAP information stored in the memory, wherein the marker indicates a time of the trigger signal with respect to sensed ECAP signals of the ECAP information.

Example 15: The system of any of examples 1 through 14, wherein the processing circuitry is configured to, responsive to receiving the trigger signal, store acceleration data representing at least one of a posture state or an activity of a patient corresponding to a same time the ECAP signals were generated.

Example 16: The system of any of examples 1 through 15, further comprising an implantable medical device comprising the memory and the processing circuitry.

Example 17: A method includes receiving, by processing circuitry, evoked compound action potential (ECAP) information, wherein the ECAP information comprises information from a plurality of evoked compound action potential (ECAP) signals; receiving, by the processing circuitry, a trigger signal requesting long-term storage of at least a portion of the ECAP information in a memory; and responsive to receiving the trigger signal, storing, by the processing circuitry, the at least portion of the ECAP information in the memory.

Example 18: The method of example 17, further includes delivering, by stimulation generation circuitry, electrical stimulation to a patient, wherein the electrical stimulation therapy comprises a plurality of stimulation pulses; sensing, by sensing circuitry, the plurality of ECAP signals by sensing each ECAP signal of the plurality of ECAP signals elicited by a respective stimulation pulse of the plurality of stimulation pulses, and receiving, by the processing circuitry, the ECAP signals from the sensing circuitry as the ECAP information.

Example 19: The method of example 18, further includes responsive to receiving the trigger signal, controlling the sensing circuitry to increase a rate at which the sensing circuitry senses subsequent ECAP signals; and storing subsequent ECAP information comprising the subsequent ECAP signals in the memory.

Example 20: The method of any of examples 17 through 19, wherein the ECAP information comprises at least one characteristic value representing respective ECAP signals of the plurality of ECAP signals, wherein the characteristic value comprises at least one of an amplitude value, a slope value, or an area under peak value.

Example 21: The method of any of examples 17 through 20, wherein the ECAP information comprises a plurality of waveforms representing respective ECAP signals of the plurality of ECAP signals.

Example 22: The method of any of examples 17 through 21, wherein the memory comprises a long-term memory, and wherein the method further comprises: storing the received ECAP information in a temporary memory; and deleting ECAP information stored in the temporary memory in response to a predetermined period of time elapsing.

Example 23: The method of any of examples 17 through 22, further comprising transmitting, by communication circuitry, the stored ECAP information to an external device.

Example 24: The method of example 23, further comprising presenting, via a display of an external device, one or more representations of the stored ECAP information.

Example 25: The method of any of examples 17 through 24, wherein the trigger signal comprises a request from an external device to store the ECAP information.

Example 26: The system of any of examples 17 through 25, wherein the trigger signal comprises a housing tap from a user, and wherein receiving the housing tap comprises: receiving accelerometer data from an accelerometer within a housing of an implantable medical device; and determining that the accelerometer data indicates a user tapped the implantable medical device.

Example 27: The method of any of examples 17 through 26, wherein the trigger signal comprises an indication that a characteristic of one ECAP signal of the plurality of ECAP signals exceeds a threshold.

Example 28: The method of any of examples 17 through 27, wherein the trigger signal comprises an indication that a user changed one or more stimulation parameter values defining electrical stimulation deliverable to a patient.

Example 29: The method of any of examples 17 through 28, further comprising, responsive to receiving the trigger signal, selecting the at least portion of the ECAP information representative of one or more ECAP signals of the plurality of ECAP signals sensed between an initial time and a final time, the initial time occurring at a first period of time prior to receiving the trigger signal and the final time occurring at a second period of time after receiving the trigger signal.

Example 30: The method of any of examples 17 through 29, further comprising adding a marker representative of the trigger signal to the at least portion of the ECAP information stored in the memory, wherein the marker indicates a time of the trigger signal with respect to sensed ECAP signals of the ECAP information.

Example 31: A computer-readable medium including instructions that, when executed by a processor, causes the processor to receive evoked compound action potential (ECAP) information, wherein the ECAP information comprises information from a plurality of evoked compound action potential (ECAP) signals; receive a trigger signal requesting long-term storage of at least a portion of the ECAP information in a memory; and responsive to receiving the trigger signal, store the at least portion of the ECAP information in the memory.

The techniques described in this disclosure may be implemented, at least in part, in hardware, software, firmware, or any combination thereof. For example, various aspects of the techniques may be implemented within one or more microprocessors, DSPs, ASICs, FPGAs, or any other equivalent integrated or discrete logic QRS circuitry, as well as any combinations of such components, embodied in external devices, such as physician or patient programmers, stimulators, or other devices. The terms "processor" and "processing circuitry" may generally refer to any of the foregoing logic circuitry, alone or in combination with other logic circuitry, or any other equivalent circuitry, and alone or in combination with other digital or analog circuitry.

For aspects implemented in software, at least some of the functionality ascribed to the systems and devices described in this disclosure may be embodied as instructions on a computer-readable storage medium such as RAM, DRAM, SRAM, FRAM, magnetic discs, optical discs, flash memories, or forms of EPROM or EEPROM. The instructions may be executed to support one or more aspects of the functionality described in this disclosure.

In addition, in some aspects, the functionality described herein may be provided within dedicated hardware and/or software modules. Depiction of different features as modules or units is intended to highlight different functional aspects and does not necessarily imply that such modules or units must be realized by separate hardware or software components. Rather, functionality associated with one or more modules or units may be performed by separate hardware or software components or integrated within common or separate hardware or software components. Also, the techniques could be fully implemented in one or more circuits or logic elements. The techniques of this disclosure may be implemented in a wide variety of devices or apparatuses, including an IMD, an external programmer, a combination of an IMD and external programmer, an integrated circuit (IC) or a set of ICs, and/or discrete electrical circuitry, residing in an IMD and/or external programmer.

What is claimed is:

1. A system comprising:
a memory; and
processing circuitry configured to:
receive evoked compound action potential (ECAP) information, wherein the ECAP information comprises information from a plurality of evoked compound action potential (ECAP) signals;
receive a trigger signal requesting long-term storage of at least a portion of the ECAP information in the memory;
responsive to receiving the trigger signal, select the at least portion of the ECAP information representative of one or more ECAP signals of the plurality of ECAP signals sensed between a first period of time prior to receiving the trigger signal and a second period of time after receiving the trigger signal; and
store the at least portion of the ECAP information in the memory.

2. The system of claim 1, further comprising:
stimulation generation circuitry configured to deliver electrical stimulation to a patient, wherein the electrical stimulation therapy comprises a plurality of stimulation pulses; and
sensing circuitry configured to sense the plurality of ECAP signals, wherein the sensing circuitry is configured to sense each ECAP signal of the plurality of ECAP signals elicited by a respective stimulation pulse of the plurality of stimulation pulses, wherein the processing circuitry is configured to receive the ECAP signals from the sensing circuitry as the ECAP information.

3. The system of claim 2, wherein the processing circuitry is configured to:
responsive to receiving the trigger signal, control the sensing circuitry to increase a rate at which the sensing circuitry senses subsequent ECAP signals; and
store subsequent ECAP information comprising the subsequent ECAP signals in the memory.

4. The system of claim 1, wherein the ECAP information comprises at least one characteristic value representing respective ECAP signals of the plurality of ECAP signals, wherein the characteristic value comprises at least one of an amplitude value, a slope value, or an area under peak value.

5. The system of claim 1, wherein the ECAP information comprises a plurality of waveforms representing respective ECAP signals of the plurality of ECAP signals.

6. The system of claim 1, wherein the memory comprises a long-term memory, and wherein the processing circuitry is configured to store the received ECAP information in a temporary memory, and wherein the processing circuitry is configured to delete ECAP information stored in the temporary memory in response to a predetermined period of time elapsing.

7. The system of claim 1, further comprising communication circuitry configured to transmit the stored ECAP information to an external device.

8. The system of claim 7, further comprising:
an external device comprising a display; and
an implantable medical device comprising the memory, the processing circuitry, and the communication circuitry configured to transmit the stored ECAP information to the external device, wherein the external device is configured to present, via the display, one or more representations of the stored ECAP information.

9. The system of claim 1, wherein the trigger signal comprises a request from an external device to store the ECAP information.

10. The system of claim 1, wherein the trigger signal comprises a housing tap from a user, and wherein the processing circuitry is configured to receive the housing tap by:
receiving accelerometer data from an accelerometer within a housing of an implantable medical device; and
determining that the accelerometer data indicates a user tapped the implantable medical device.

11. The system of claim 1, wherein the trigger signal comprises an indication that a characteristic of one ECAP signal of the plurality of ECAP signals exceeds a threshold.

12. The system of claim 1, wherein the trigger signal comprises an indication that a user changed one or more stimulation parameter values defining electrical stimulation deliverable to a patient.

13. The system of claim 1, wherein the processing circuitry adds a marker representative of the trigger signal to the at least portion of the ECAP information stored in the memory, wherein the marker indicates a time of the trigger signal with respect to sensed ECAP signals of the ECAP information.

14. The system of claim 1, wherein the processing circuitry is configured to, responsive to receiving the trigger signal, store acceleration data representing at least one of a posture state or an activity of a patient corresponding to a same time the ECAP signals were generated.

15. The system of claim 1, further comprising an implantable medical device comprising the memory and the processing circuitry.

16. The system of claim 1, wherein at least one ECAP signal of the one or more ECAP signals was sensed after the first period of time and prior to receiving the trigger signal.

17. A method comprising:
receiving, by processing circuitry, evoked compound action potential (ECAP) information, wherein the ECAP information comprises information from a plurality of evoked compound action potential (ECAP) signals;
receiving, by the processing circuitry, a trigger signal requesting long-term storage of at least a portion of the ECAP information in a memory;
responsive to receiving the trigger signal, select the at least portion of the ECAP information representative of one or more ECAP signals of the plurality of ECAP signals sensed between a first period of time prior to receiving the trigger signal and a second period of time after receiving the trigger signal; and
storing, by the processing circuitry, the at least portion of the ECAP information in the memory.

18. The method of claim 17, further comprising:
delivering, by stimulation generation circuitry, electrical stimulation to a patient, wherein the electrical stimulation therapy comprises a plurality of stimulation pulses;
sensing, by sensing circuitry, the plurality of ECAP signals by sensing each ECAP signal of the plurality of ECAP signals elicited by a respective stimulation pulse of the plurality of stimulation pulses, and
receiving, by the processing circuitry, the ECAP signals from the sensing circuitry as the ECAP information.

19. The method of claim 18, further comprising:
responsive to receiving the trigger signal, controlling the sensing circuitry to increase a rate at which the sensing circuitry senses subsequent ECAP signals; and
storing subsequent ECAP information comprising the subsequent ECAP signals in the memory.

20. The method of claim 17, wherein the ECAP information comprises at least one characteristic value representing respective ECAP signals of the plurality of ECAP signals, wherein the characteristic value comprises at least one of an amplitude value, a slope value, or an area under peak value.

21. The method of claim 17, wherein the ECAP information comprises a plurality of waveforms representing respective ECAP signals of the plurality of ECAP signals.

22. The method of claim 17, wherein the memory comprises a long-term memory, and wherein the method further comprises:

storing the received ECAP information in a temporary memory; and deleting ECAP information stored in the temporary memory in response to a predetermined period of time elapsing.

23. The method of claim 17, further comprising transmitting, by communication circuitry, the stored ECAP information to an external device.

24. The method of claim 23, further comprising presenting, via a display of an external device, one or more representations of the stored ECAP information.

25. The method of claim 17, wherein the trigger signal comprises a request from an external device to store the ECAP information.

26. The system of claim 17, wherein the trigger signal comprises a housing tap from a user, and wherein receiving the housing tap comprises:

receiving accelerometer data from an accelerometer within a housing of an implantable medical device; and determining that the accelerometer data indicates a user tapped the implantable medical device.

27. The method of claim 17, wherein the trigger signal comprises an indication that a characteristic of one ECAP signal of the plurality of ECAP signals exceeds a threshold.

28. The method of claim 17, wherein the trigger signal comprises an indication that a user changed one or more stimulation parameter values defining electrical stimulation deliverable to a patient.

29. The method of claim 17, further comprising adding a marker representative of the trigger signal to the at least portion of the ECAP information stored in the memory, wherein the marker indicates a time of the trigger signal with respect to sensed ECAP signals of the ECAP information.

30. A non-transitory computer-readable medium comprising instructions that, when executed by a processor, causes the processor to:

receive evoked compound action potential (ECAP) information, wherein the ECAP information comprises information from a plurality of evoked compound action potential (ECAP) signals;

receive a trigger signal requesting long-term storage of at least a portion of the ECAP information in a memory;

responsive to receiving the trigger signal, select the at least portion of the ECAP information representative of one or more ECAP signals of the plurality of ECAP signals sensed between a first period of time prior to receiving the trigger signal and a second period of time after receiving the trigger signal; and store the at least portion of the ECAP information in the memory.

\* \* \* \* \*